United States Patent
Imanishi et al.

(10) Patent No.: US 10,253,360 B2
(45) Date of Patent: Apr. 9, 2019

(54) BNA CLAMP METHOD

(71) Applicant: BNA INC., Ibaraki-shi, Osaka (JP)

(72) Inventors: Takeshi Imanishi, Ibaraki (JP); Ayako Orita, Ibaraki (JP); Ikuya Ban, Ibaraki (JP)

(73) Assignee: BNA INC., Ibaraki (JP)

(*) Notice: Subject to any disclaimer, the term of this patent is extended or adjusted under 35 U.S.C. 154(b) by 712 days.

(21) Appl. No.: 14/431,380

(22) PCT Filed: Sep. 27, 2013

(86) PCT No.: PCT/JP2013/076329
§ 371 (c)(1),
(2) Date: Mar. 26, 2015

(87) PCT Pub. No.: WO2014/051076
PCT Pub. Date: Apr. 3, 2014

(65) Prior Publication Data
US 2015/0240299 A1 Aug. 27, 2015

(30) Foreign Application Priority Data

Sep. 28, 2012 (JP) .................. 2012-217657

(51) Int. Cl.
| | | |
|---|---|---|
| C12Q 1/68 | (2018.01) | |
| C12Q 1/6858 | (2018.01) | |
| C07H 19/06 | (2006.01) | |
| C07H 19/16 | (2006.01) | |
| C07H 21/02 | (2006.01) | |
| C07H 21/04 | (2006.01) | |

(52) U.S. Cl.
CPC .......... C12Q 1/6858 (2013.01); C07H 19/06 (2013.01); C07H 19/16 (2013.01); C07H 21/02 (2013.01); C07H 21/04 (2013.01)

(58) Field of Classification Search
CPC .................................. C12Q 1/6858
USPC ................................ 435/6.1, 6.11
See application file for complete search history.

(56) References Cited

U.S. PATENT DOCUMENTS

| | | | |
|---|---|---|---|
| 6,770,748 B2 | 8/2004 | Imanishi et al. | |
| 7,427,672 B2 | 9/2008 | Imanishi et al. | |
| 7,569,686 B1* | 8/2009 | Bhat ................ | C07H 19/00 536/18.1 |
| 7,615,619 B2 | 11/2009 | Imanishi et al. | |
| 7,994,145 B2 | 8/2011 | Imanishi et al. | |

FOREIGN PATENT DOCUMENTS

| | | |
|---|---|---|
| JP | 3756313 B2 | 3/2006 |
| JP | 2006-304611 A | 11/2006 |
| JP | 4151751 B2 | 9/2008 |
| JP | 4216266 B2 | 1/2009 |
| JP | 4383176 B2 | 12/2009 |
| JP | 4731324 B2 | 7/2011 |
| JP | 5030998 B2 | 9/2012 |

OTHER PUBLICATIONS

Nielsen et al. J. Chem. Soc. Perkin Trans. 1, 1997 pp. 3423-3433.*
Araki et al., *Journal of Molecular Diagnostics*, 12(1): 118-124 (2010).
Biosynthesis, "BNA PNA, LNA, DNA Comparison" (Dec. 20, 2005) [retrieved from internet at URL: http://www.biosyn.com/TEW/BNA-PNA-LNA-DNA-Comparison.aspx on Dec. 16, 2013].
Biosynthesis, "Bridged Nucleic Acid (BNA) Oligonucleotide" (Jun. 28, 2012) [retrieved from internet at URL: http://www.biosyn.com/TEW/Bridged-Nucleic-Acid-%28BNA%29-Oligonucleotide.aspx on Dec. 16, 2013].
Biosynthesis, "What is PCR Clamping?" (Aug. 28, 2008) [retrieved from internet at URL: http://www.biosyn.com/faq/What-is-PCR-Clamping.aspx on Dec. 16, 2013].
Chen et al., *Analytical Biochemistry*, 195: 51-56 (1991).
Chiou et al., *Nature Protocols*, 1(6): 2604-2612 (2006).
Imanishi, *Journal of Clinical and Experimental Medicine*, 238(5): 447-453 (2011).
Jacobson, *Oncogene*, 9(2): 553-563 (1994) [abstract].
Kobika et al., "Development of BNA (LNA) and its application to genome technology," *CSJ Current Review*, 6: 181-187 (Jul. 30, 2011).
Krypuy et al., *BMC Cancer*, 6: 295 [doi:10. 1186/1471-2407-6-295] (Dec. 21, 2006).
Newton et al., *Nucleic Acids Research*, 17(7): 2503-2516 (1989).
Nollau et al., *Clinical Chemistry*, 43(7): 1114-1128 (1997).

(Continued)

*Primary Examiner* — Jezia Riley
(74) *Attorney, Agent, or Firm* — Leydig, Voit & Mayer, Ltd.

(57) ABSTRACT

The invention provides a method of selectively amplifying a detection target nucleic acid by inhibiting amplification of a detection non-target nucleic acid (e.g., wild-type gene) in a test sample by using, in a nucleic acid amplification reaction, an oligonucleotide analog containing one or more kinds of one or more unit structures of various nucleoside analogs represented by the following formula (I):

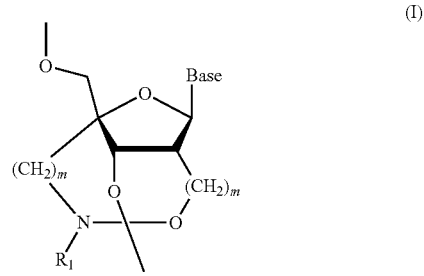

(I)

wherein the symbols are as defined in the DESCRIPTION, and the like, or a salt thereof, as a clamp nucleic acid, and detecting the amplified nucleic acid.

21 Claims, 19 Drawing Sheets
Specification includes a Sequence Listing.

(56) References Cited

OTHER PUBLICATIONS

Nordgard et al., *Diagn. Mol. Pathol.*, 21(1): 9-13 (2012).
Ogino et al., *Journal of Molecular Diagnostics*, 7(3): 413-421 (2005).
Senescau et al., *Journal of Clinical Microbiology*, 43(7): 3304-3308 (2005).
Tanaka et al., "PNA-LNA PCR claimp-ho ni yoru Smart Cycler II System o Mochiita EGFR Hen'l no Kokando Jinsoku Kenshutsu System no Kaihatsu," *Bio View*, 50: 9-13 and additional pp. 1/3-3/3 (2005) [retrieved from internet at URL: http://catalog.takara-bio.co.jp/PDFFiles/50_09-13.pdf on Dec. 16, 2013].
Wu et al., *Proc. Natl. Acad. Sci.*, 86: 2757-2760 (1989).
Japanese Patent Office, International Search Report in International Patent Application No. PCT/JP2013/076329 (dated Jan. 7, 2014).
Japanese Patent Office, Written Opinion in International Patent Application No. PCT/JP2013/076329 (dated Jan. 7, 2014).
Dominguez et al., *Oncogene*, 24: 6830-6834 (2005).
Huang et al., *Molecular and Cellular Probes*, 24: 376-380 (2010).
Marras et al., *Clinica Chimica Acta*, 363: 48-60 (2006).
Miyashita et al., *Chem. Commun.*, 3765-3767 (2007).
Oldenburg et al., *Journal of Investigative Dermatology*, 128: 398-402 (2008).
Rahman et al., *J. Am. Chem. Soc.*, 130: 4886-4896 (2008).
European Patent Office, Supplementary Partial European Search Report in European Patent Application No. 13841056 (dated Apr. 1, 2016).
Prakash et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.*, 53(4): 1636-1650 (2010).
Rahman et al., "RNA interference with 2',4'-bridged nucleic acid analogues," *Bioorg. Med. Chem.*, 18(1): 3474-3480 (2010).
Yamamoto et al., "Superior Silencing by 2',4'-BNA$^{NC}$-Based Short Antisense Oligonucleotides Compared to 2',4'-BNA/LNA-Based Apolipoprotein B Antisense Inhibitors," *J. Nucleic Acids*, 2012: 707323 (2012).
Yamamoto et al., "Cholesterol-lowering Action of BNA-based Antisense Oligonucleotides Targeting PCSK9 in Atherogenic Diet-induced Hypercholesterolemic Mice," *Mol. Ther. Nucleic Acids*, 1: e22 (2012).

* cited by examiner

| curve in Figure | —·— | — — | —··— | —— | – – | ····· |
|---|---|---|---|---|---|---|
| M/(M+W) (%) in test sample | 100 | 10 | 1 | 0.1 | 0.01 | 0 |

| curve in Figure | —·— | — — | —··— | —— | – – | ····· |
|---|---|---|---|---|---|---|
| M/(M+W) (%) in test sample | 100 | 10 | 1 | 0.1 | 0.01 | 0 |

| curve in Figure | -·-·- | ---- | -··- | —— | — — | ······ |
|---|---|---|---|---|---|---|
| M/(M+W) (%) in test sample | 100 | 10 | 1 | 0.1 | 0.01 | 0 |

| curve in Figure | ![dash-dot-dot] | ![dash-dash] | ![dash-dot] | ![solid] | ![long-dash] | ![dotted] |
|---|---|---|---|---|---|---|
| M/(M+W) (%) in test sample | 100 | 10 | 1 | 0.1 | 0.01 | 0 |

Oligo 8 (DNA)

oligo 10 (PNA)

Oligo 9 (LNA)

oligo 5 (BNA)

| curve in Figure | —··— | — — | —·· | —— | — — | ······ |
|---|---|---|---|---|---|---|
| M/(M+W) (%) in test sample | 100 | 10 | 1 | 0.1 | 0.01 | 0 |
| Ct value | 23.07 | 26.64 | 30.17 | 32.89 | 36.81 | not detected |
| ΔCt (0%-X%) | – | – | – | – | – | – | a)

| curve in Figure | ‒ ‒ ‒ | ‒ · ‒ · | ——— | ‒ ‒ | ········ |
|---|---|---|---|---|---|
| M/(M+W) (%) | 10% | 1% | 0.1% | 0.01% | 0% |
| Ct value | 23.39 | 26.80 | 29.74 | 30.22 | 30.43 |
| ΔCt value (0%-X%) | 7.04 | 3.63 | 0.70 | 0.21 | | b)

| curve in Figure | - - - | -·-·- | —— | - - | ······ |
|---|---|---|---|---|---|
| M/(M+W) (%) | 10% | 1% | 0.1% | 0.01% | 0% |
| Ct value | 24.49 | 27.92 | 30.71 | 33.80 | 34.71 |
| ΔCt value (0%-X%) | 10.22 | 6.79 | 4.00 | 0.91 | | a)

| curve in Figure | --- | -·- | — | -- | ···· |
|---|---|---|---|---|---|
| M/(M+W) (%) | 10% | 1% | 0.1% | 0.01% | 0% |
| Ct value | - | - | - | - | - |
| ΔCt value (0%-X%) | - | - | - | - | | b)

| curve in Figure | --- | -·- | — | -- | ···· |
|---|---|---|---|---|---|
| M/(M+W) (%) | 10% | 1% | 0.1% | 0.01% | 0% |
| Ct value | 29.55 | 34.10 | 46.20 | - | >55 |
| ΔCt value (0%-X%) | >25.45 | >20.90 | >8.80 | - | |

| curve in Figure | −··− | −−− | −·− | ─── | ▬▬▬ | ······ |
|---|---|---|---|---|---|---|
| M/(M+W) (%) in test sample | 100 | 10 | 1 | 0.1 | 0.01 | 0 |

BNA CLAMP METHOD

CROSS-REFERENCE TO RELATED APPLICATIONS

This patent application is the U.S. national phase of International Patent Application No. PCT/JP2013/076329, filed Sep. 27, 2013, which claims the benefit of Japanese Patent Application No. 2012-217657, filed on Sep. 28, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 19,301 bytes ASCII (Text) file named "720280Sequence-Listing.txt," created Mar. 25, 2015.

TECHNICAL FIELD

The present invention relates to a method of detecting a difference in the base sequences of nucleic acids, and a kit therefor. More specifically, the present invention relates to a method of detecting a difference in the base sequences by using a clamp nucleic acid in nucleic acid amplification techniques, and a kit therefor.

BACKGROUND ART

An acquired genetic mutation in somatic cells is sometimes highly responsible for, together with congenital genetic mutations in germ cells, susceptibility to a certain kind of disease, a therapeutic effect of a drug, strength of side effects and the like. In cancer cells, various genetic mutations occur at somatic cell level, and the mutations trigger cancer and greatly influence the response efficiency of molecular target drugs. In non-small cell lung cancer, for example, when EGFR gene is mutated, the response efficiency of gefitinib (trade name Iressa), which is one kind of molecular target drugs, becomes high and, when it is not mutated, the response efficiency becomes low. In colorectal cancer, when KRAS gene is mutated, the response efficiency of a molecular target drug cetuximab (trade name Erbitax) becomes low and, when it is not mutated, the response efficiency becomes high. Consequently, when a therapy using a molecular target drug is applied to these diseases, previous examination of the presence or absence of a mutation of the gene is increasingly required.

There are largely two kinds of methods for detecting a detection target nucleic acid (mutated gene) in somatic cells. One of them is a detection method including non-selectively amplifying a mutated gene and a detection non-target nucleic acid (wild-type gene), after which distinguishing the mutated gene from the wild-type gene. This detection method includes various methods such as a method utilizing electrophoresis, a method utilizing hybridization, and the like (see, for example, non-patent document 1). In most of the methods, however, detection of a slight amount of a mutated gene contained in a wild-type gene with sufficient sensitivity and accuracy is difficult. For example, a general detection method of mutated gene is the dideoxysequencing method. While the dideoxysequencing method permits detection of a mutated gene, present alone, with comparatively high sensitivity, when a mutated gene is contained in a trace amount in a wild-type gene, detection is possible only when the mutated gene is contained in about 10%. While the pyrosequencing method is superior to the dideoxysequencing method, the detection sensitivity thereof is reported to be about 5% (see, for example, non-patent document 2). Furthermore, a method including amplifying a mixed sample of mutated and wild-type genes by PCR, drawing a melting curve of a double stranded DNA of the amplification product thereof, and determining the ratio of the mutated gene from the difference in the melting curves of the mutated gene and the wild-type gene has been developed. Even by this method, the detection sensitivity of a mutated gene contained in a wild-type gene is about 5% (see, for example, non-patent document 3).

Another method for detecting a mutated gene in somatic cells is a method including distinguishing a wild-type gene from a mutated gene in the stage of gene amplification. Specifically, the method includes selective amplification of a mutated gene alone.

For example, it includes a method called "mutant-enriched PCR", wherein a wild-type gene alone is cleaved with a restriction enzyme, and a non-cleaved mutated gene alone is amplified (e.g., non-patent document 4). This method is considered to be able to detect 1 molecule of a mutated gene in $10^6$ molecules of a wild-type gene by repeating a reaction to amplify the mutated gene (see, for example, non-patent document 5). While this method is superior in high sensitivity as mentioned above, it cannot be applied to general diagnoses since the operation is highly complicated.

In an elongation reaction of primers in PCR and the like, a method including amplification by distinguishing a difference in a single base has been developed. This method is called "ARMS (amplification refractory mutation system)" (see, for example, non-patent document 6), "ASPCR (allele specific PCR)" (see, for example, non-patent document 7) and the like. This method is a superior method since it has comparatively high sensitivity, does not require an operation other than general PCR amplification reactions, can perform whole reactions in a closed system, is highly convenient, and is free of contamination. However, when a wild-type gene is amplified even once due to erroneous distinction of a single base, the risk of false-positivity becomes high since a wild-type gene is also amplified, like the amplification of mutated gene, in the subsequent amplification reaction. When this method is used, the reaction conditions, i.e., reaction temperature, salt concentration and the like, need to be controlled strictly, and the amount of templates needs to be precisely the same (see, for example, e.g., non-patent document 1), and therefore, the method is not suitable for clinical tests to examine an unspecified large number of samples, and diagnosis requiring high accuracy.

In the nucleic acid amplification techniques such as PCR and the like, another amplification method including distinguishing differences in the bases is a technique for inhibiting amplification of a wild-type gene by using an artificial oligonucleotide having a suitable kind and length of a structure completely complementary to a wild-type gene, or what is called a "clamp method". A material for a clamp nucleic acid is required to, in a nucleic acid amplification process, (i) strongly hybridize to a wild-type gene, (ii) not strongly hybridize to a mutated gene, and (iii) resist decomposition in a nucleic acid amplification process. Accordingly, DNA and RNA composed of a natural material are not suitable in terms of hybridization capability and decomposition resistance, and artificial nucleic acids such as peptide nucleic acid (PNA) and locked nucleic acid (LNA) are exclusively used as a material for the clamp nucleic acid for the clamp technique (see, for example, e.g., non-patent documents 8-11 and patent documents 1, 2).

PNA is an artificial nucleic acid generally utilized as a fully-modified type and has properties desirable as a clamp nucleic acid, since it shows stronger hybridization capability to a DNA strand having a complementary structure than does natural DNA, shows good difference from the hybridization capability to a DNA strand having a one-base mismatch sequence, and free of degradation by nucleases. As such, it is frequently used as a clamp nucleic acid for the analysis and detection of various mutations of various genes. On the other hand, LNA is an artificial nucleic acid utilized as a partially modified type. Since every modification of one unit strikingly enhances the hybridization capability, it can be controlled by the length and modification mode to acquire suitable hybridization capability. As such, it is possible to afford a clamp effect by using a comparatively short LNA oligonucleotide.

However, the above-mentioned clamp nucleic acids each have difficulties. Even if PNA "shows higher hybridization capability than natural DNA", the level thereof is limited and the clamp nucleic acid needs to be elongated to acquire good hybridization capability and exhibit a sufficient clamp effect. In addition, while LNA is completely free of problems relating to the hybridization capability, its chemical stability in the amplification process poses problems since resistance thereof to the nucleases is not very strong and, comprehensively, LNA is not entirely superior in clamp capacity.

The present inventors have developed, after the development of 2',4'-BNA (LNA), which is a crosslinking structure type novel artificial nucleic acid (first generation BNA) (e.g., patent document 3), BNAs of the second generation and thereafter such as 3'-amino-2',4'-BNA, 5'-amino-2',4'-BNA, 2',4'-BNA$^{coc}$, 2',4'-BNA$^{NC}$ and the like (e.g., patent documents 4-7).

DOCUMENT LIST

Patent Documents patent document 1: JP-B-4216266
patent document 2: JP-A-2006-304611
patent document 3: JP-B-3756313
patent document 4: JP-B-4731324
patent document 5: JP-B-4383178
patent document 6: JP-B-5030998
patent document 7: JP-B-4151751

Non-Patent Documents non-patent document 1: Nollau et al., Clinical Chemistry, 1997, vol. 43, pages 1114-1128
non-patent document 2: Ogino et al., The Journal of Molecular Diagnostics, 2005, vol. 7, pages 413-421
non-patent document 3: Krypuy et al., BMC Cancer, 2006, vol. 6, page 295
non-patent document 4: Chen et al., Analytical biochemistry, 1991, vol. 195, pages 51-56
non-patent document 5: Jacobson et al., Oncogene, 1994, vol. 9, pages 553-563
non-patent document 6: Newton et al., Nucleic acids research, 1989, vol. 17, pages 2503-2516
non-patent document 7: Wu et al., Proceedings of the National Academy of Sciences of the United States of America, 1989, vol. 86, pages 2757-2760
non-patent document 8: Senescau et al., Journal of Clinical Microbiology, 2005, vol. 43, pages 3304-3308
non-patent document 9: Araki et al., Journal of Molecular Diagnostics, 2010, vol. 12, pages 118-124
non-patent document 10: Chiou et al., Nature Protocol, 2007, vol. 1, pages 2604-2612
non-patent document 11: Nordgard et al., Diagnostic Molecular Pathology, 2012, vol. 21, pages 9-13

SUMMARY OF THE INVENTION

Problems to be Solved by the Invention

The present invention has been made in view of the aforementioned situation of the technical field, and aims to provide a convenient and economical test method capable of detecting the presence or absence of a mutated gene and mutation mode with high sensitivity and high accuracy, from a test sample mostly containing a wild-type gene and containing a mutated gene only in a trace amount.

Means of Solving the Problems

The present inventors have conducted intensive studies in an attempt to solve the aforementioned problem and particularly took note of a clamp method from various test methods. The present inventors further conceived use of BNAs of the second generation and thereafter as clamp nucleic acids, and conducted experiments using, as the target, model test samples containing a wild-type gene and a mutated gene at various known ratios. As a result, they have found that, by using BNAs of the second generation and thereafter as clamp nucleic acids, a mutated gene can be highly selectively amplified even in a test sample containing a mutated gene only in an extremely small amount in a large amount of a wild-type gene and, specifically, the presence of a mutated gene can be easily detected even when it is present only at about 0.1-1%. The present inventors have further found that the detection sensitivity of the mutated gene can be further enhanced (detection sensitivity of about 0.01%) by combinedly using a detection probe that selectively traps the target mutated gene amplification product. The present inventors conducted further studies based on these findings and completed the present invention.

Accordingly, the present invention provides the following.

[1] A method of detecting a target nucleic acid having a difference in a base sequence in a detection target site in the target nucleic acid in a test sample, wherein the target nucleic acid comprises at least one difference in the base sequence from a detection non-target nucleic acid, comprising a step of selectively amplifying a region containing at least a part of the detection target site of the detection target nucleic acid in the test sample by a nucleic acid amplification method using a clamp nucleic acid having a base sequence complementary to the base sequence of the detection target site in the detection non-target nucleic acid, and a step of detecting the amplified nucleic acid, wherein the clamp nucleic acid is an oligonucleotide analog containing one or more of one or more kinds of unit structures of nucleoside analogs represented by the following formula (I):

(I)

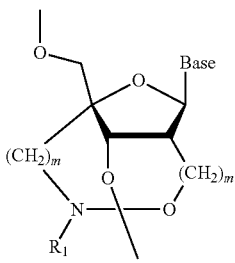

wherein

Base is a pyrimidine or purine nucleic acid base optionally having one or more substituents, $R_1$ is a hydrogen atom, an alkyl group, an alkenyl group, a cycloalkyl group, an aryl group, an aralkyl group, an acyl group, a sulfonyl group, a silyl group, or a functional molecule unit substituent, m is an integer of 0-2, and n1 is an integer of 1-3, the following formula (II):

(II)

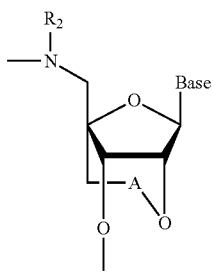

wherein

Base is as defined above,

A is a direct bond, an alkylene group having 1-4 carbon atoms, —O—(CH$_2$)$_{n2}$— (wherein the oxygen atom is bonded to the 4'-position methylene group, and n2 is an integer of 1-3), or —N(R$_3$)—(CHA$_{n3}$— (wherein the nitrogen atom is bonded to the 4'-position methylene group, and n3 is an integer of 1-3), $R_2$ and $R_3$ are the same or different and each is a hydrogen atom, a hydroxyl-protecting group for nucleic acid synthesis, an alkyl group, an alkenyl group, a cycloalkyl group, an aralkyl group, an aryl group, an acyl group, a silyl group, a phosphate group, a phosphate group protected with a protective group for nucleic acid synthesis, or —P(R$_4$)R$_5$ [where R$_4$ and R$_5$ are the same or different, and each represent a hydroxyl group, a hydroxyl group protected with a protective group for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms]), the following formula (III):

(III)

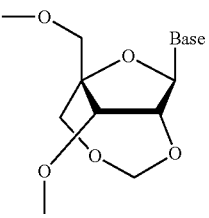

wherein Base is as defined above,
or the following formula (IV):

(IV)

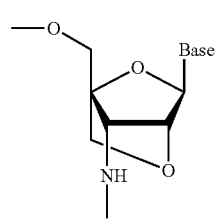

wherein Base is as defined above, provided a binding form between respective nucleoside analogs in the oligonucleotide analogs optionally contains one or more phosphorothioate bonds in addition to a phosphodiester bond and, when two or more of one or more kinds of the aforementioned unit structures are contained, Base may be the same or different between the structures, or a salt thereof.

[2] The method of the above-mentioned [1], wherein the clamp nucleic acid is an oligonucleotide analog containing one or more of one or more kinds of unit structures of nucleoside analogs of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a hydrogen atom, an alkyl group having 1 to 5 carbon atoms, a benzyl group, an acetyl group, a benzoyl group, a methanesulfonyl group, or a p-toluenesulfonyl group, m is an integer of 0-2, and n1 is an integer of 1-3, or a salt thereof.

[3] The method of the above-mentioned [1] or [2], wherein the clamp nucleic acid is an oligonucleotide analog containing one or more of one or more kinds of unit structures of nucleoside analogs of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a methyl group, m is 0, and n1 is 1, or a salt thereof.

[4] The method of any one of the above-mentioned [1] to [3], wherein the clamp nucleic acid has a length of 5-25 mer.

[5] The method of any one of the above-mentioned [1] to [4], wherein the nucleic acid amplification method is a polymerase chain reaction (PCR) method.

[6] The method of the above-mentioned [5], wherein the PCR method is a real-time PCR method.

[7] The method of the above-mentioned [6], wherein the real-time PCR method is performed using a detection probe, and the detection probe is a single strand nucleic acid having a base sequence complementary to the base sequence of the region to be detected for a difference in a base sequence in a detection target site, wherein one terminal is substituted by a fluorescence group, the other terminal is substituted by a quenching group.

[8] The method of the above-mentioned [7], wherein the detection probe is an oligonucleotide analog containing one or more of one or more kinds of unit structures of nucleoside analogs of any one of the above-mentioned formulas (I)-(IV), or a salt thereof.

[9] The method of any one of the above-mentioned [1] to [8], wherein the difference in the base sequence between the detection non-target nucleic acid and the detection target nucleic acid is caused by one or more mutations selected from the group consisting of substitution, insertion, deletion, inversion, overlap and translocation or a combination thereof.

[10] The method of any one of the above-mentioned [1] to [9], wherein the step of detecting the amplified nucleic acid comprises sequencing of an amplification product.

[11] The method of any one of the above-mentioned [1] to [10], wherein the target nucleic acid is a gene, and the difference in the base sequence of the gene to be the detection target relates to the onset and/or treatment sensitivity of a particular disease.

[12] A kit for detection of a target nucleic acid having a difference in a base sequence in a detection target site in the target nucleic acid in a test sample, wherein the target nucleic acid is a detection target nucleic acid having at least one difference in a base sequence from a detection non-target nucleic acid, the kit comprising (a) a clamp nucleic acid having a base sequence complementary to the base sequence of the detection target site of a detection non-target nucleic acid, and (b) a reagent for selectively amplifying a region containing at least a part of the detection target site of the detection target nucleic acid in the test sample, wherein the clamp nucleic acid is an oligonucleotide analog containing one or more of one or more kinds of unit structures of nucleoside analogs represented by the following formula (I):

(I)

wherein

Base is a pyrimidine or purine nucleic acid base optionally having one or more substituents, $R_1$ is a hydrogen atom, an alkyl group, an alkenyl group, a cycloalkyl group, an aryl group, an aralkyl group, an acyl group, a sulfonyl group, a silyl group, or a functional molecule unit substituent, m is an integer of 0-2, and n1 is an integer of 1-3, the following formula (II):

(II)

wherein

Base is as defined above,

A is a direct bond, an alkylene group having 1-4 carbon atoms, $-O-(CH_2)_{n2}-$ (wherein oxygen atom is bonded to the 4'-position methylene group, and n2 is an integer of 1-3), or $-N(R_3)-(CH_2)_{n3}-$ (wherein nitrogen atom is bonded to the 4'-position methylene group, and n3 is an integer of 1-3), $R_2$ and $R_3$ are the same or different and each is a hydrogen atom, a hydroxyl-protecting group for nucleic acid synthesis, an alkyl group, an alkenyl group, a cycloalkyl group, an aralkyl group, an aryl group, an acyl group, a silyl group, a phosphate group, a phosphate group protected with a protecting group for nucleic acid synthesis, or $-P(R_4)R_5$ (wherein $R_4$ and $R_5$ are the same or different and each is a hydroxyl group, a hydroxyl group protected with for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms), the following formula (III):

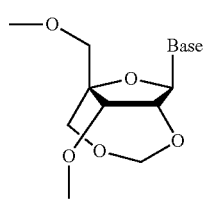

(III)

wherein Base is as defined above,
or the following formula (IV):

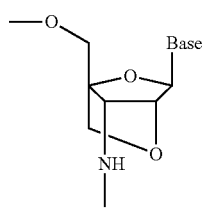

(IV)

wherein Base is as defined above,
provided a binding form between respective nucleoside analogs in the oligonucleotide analogs optionally contains one or more phosphorothioate bonds in addition to a phosphodiester bond and, when two or more of one or more kinds of the aforementioned unit structures are contained, Base may be the same or different between the structures, or a salt thereof.

[13] The kit of the above-mentioned [12], wherein the clamp nucleic acid is an oligonucleotide analog containing one or more of one or more kinds of unit structures of nucleoside analogs of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a hydrogen atom, an alkyl group having 1 to 5 carbon atoms, a benzyl group, an acetyl group, a benzoyl group, a methanesulfonyl group, or a p-toluenesulfonyl group, m is an integer of 0-2, and
n1 is an integer of 1-3,
or a salt thereof.

[14] The kit of the above-mentioned [12] or [13], wherein the clamp nucleic acid is an oligonucleotide analog containing one or more of one or more kinds of unit structures of nucleoside analogs of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a methyl group,
m is 0, and
n1 is 1,
or a salt thereof.

[15] The kit of any one of the above-mentioned [12] to [14], wherein the clamp nucleic acid has a length of 5-30 mer.

[16] The kit of any one of the above-mentioned [12] to [15], wherein the reagent of the aforementioned (b) comprises an amplification primer for polymerase chain reaction (PCR).

[17] The kit of the above-mentioned [16], wherein the reagent of the aforementioned (b) further comprises a reagent for real-time PCR.

[18] The kit of the above-mentioned [17], wherein the real-time PCR method is performed using a detection probe, and the detection probe is a single strand nucleic acid having a base sequence complementary to the base sequence of the region to be detected for a difference in a base sequence in a detection target nucleic acid, wherein one terminal is substituted by a fluorescence group, the other terminal is substituted by a quenching group.

[19] The kit of the above-mentioned [18], wherein the detection probe is an oligonucleotide analog containing one or more of one or more kinds of unit structures of nucleoside analogs of any one of the above-mentioned formulas (I)-(IV), or a salt thereof.

[20] The kit of any one of the above-mentioned [12] to [19], wherein the difference in the base sequence between the detection non-target nucleic acid and the detection target nucleic acid is caused by one or more mutations selected from the group consisting of substitution, insertion, deletion, inversion, overlap and translocation or a combination thereof.

[21] The kit of any one of the above-mentioned [12] to [20], wherein the target nucleic acid is a gene, and the difference in the base sequence of the gene to be the detection target relates to the onset and/or treatment sensitivity of a particular disease.

Effect of the Invention

The present invention permits highly sensitive and highly accurate detection of the presence or absence of a mutated gene and mutation mode, as well as convenient and accurate tests of point mutation, deletion mutation, insertion mutation and the like of various genes at a low costs, even from a test sample containing only a trace amount a mutated gene (detection target nucleic acid) in the target nucleic acid which is mostly a wild-type gene (detection non-target nucleic acid).

Figure 25:
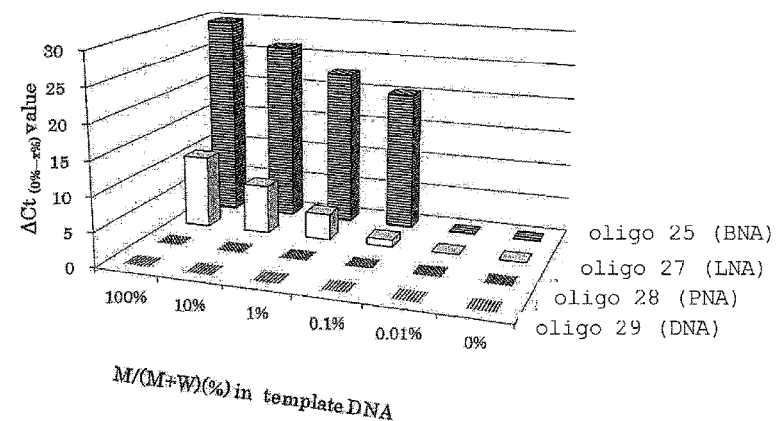

FIG. 25 shows a graph for comparison of the clamp function between BNA clamp (oligo 25) and other clamps (oligo 27-29) in real-time PCR of respective test samples (mixed sample of mutated/(mutated+wild-type)(100%-0%) genes) targeting EGFR gene E746-A750 del (Type 1) mutation in Example 6.

DESCRIPTION OF EMBODIMENTS (Detection Method)

The present invention provides a method of detecting a target nucleic acid having a difference in a base sequence in a detection target site in the target nucleic acid in a test sample (hereinafter to be also referred to as the method of the present invention). As used herein, the target nucleic acid is a detection target nucleic acid having at least one difference in a base sequence from a detection non-target nucleic acid. The method of the present invention includes (1) a step of selectively amplifying a region containing at least a part of the detection target site of the detection target nucleic acid in the test sample by a nucleic acid amplification method using a clamp nucleic acid having a base sequence complementary to the base sequence of the detection target site of a detection non-target nucleic acid and (2) a step of detecting the amplified nucleic acid.

A test sample to be the target of the method of the present invention is not particularly limited as long as it is assumed to contain a nucleic acid for which detection of mutation is desired. The test sample is typically collectable from mammals, preferably human, and includes liquid samples such as blood, pleural fluid, bronchus washing, bone marrow fluid, lymph fluid and the like, and solid samples such as lymph node, blood vessel, bone marrow, brain, spleen, skin and the like. Since the method of the present invention can detect mutation of a nucleic acid with very high sensitivity, a liquid sample containing only a trace amount of a test target sample such as blood and the like can be used without directly collecting a sample from, for example, a lesion such as cancer and the like. Therefore, preferable test samples are liquid samples such as blood and the like.

The "target nucleic acid" in the method of the present invention is a nucleic acid to be the target of the detection of a difference in a base sequence, and refers to a detection target nucleic acid having at least one difference in a base sequence from a detection target nucleic acid (e.g., mutated gene) and detection non-target nucleic acid (e.g., wild-type gene) in the detection target site. While nucleic acid may be DNA or RNA, it is preferably a DNA, specifically a gene. A preferable gene is a gene known to have a difference in the base sequence thereof, i.e., mutation (preferably, acquired mutation), relating to the onset and/or treatment sensitivity of a particular disease. The "onset" here includes not only actual onset of disease but also onset risk and the like, and the "treatment sensitivity" not only the response efficiency of treatment with drugs and the like but also strength and weakness and the like of side effects. The above-mentioned diseases are not limited to the following, and examples thereof include cancer, myelodysplastic syndrome, HIV-1 infections, thrombosis, embolism, rejection in transplantation, attention deficit/hyperactivity disorder and the like, preferably cancer.

Examples of the gene, the mutation of which is known to relate to the onset of cancer and/or treatment sensitivity, include the following (type of cancer is jointly indicated), and these genes are preferable target examples:

ABL/BCR fusion gene (chronic myeloid leukemia), HER2 gene (breast cancer), EGFR gene (non-small cell lung cancer), c-KIT gene (gastrointestinal stromal tumor), KRAS gene (colorectal cancer, pancreatic cancer), BRAF gene (melanoma, colorectal cancer), PI3KCA gene (lung cancer, colorectal cancer), FLT3gene (acute myeloid leukemia), MYC gene (various carcinomas), MYCN gene (neuroblastoma), MET gene (lung cancer, gastric cancer, melanoma), BCL2 gene (follicular B lymphoma), EML4/AIK fusion gene (lung cancer).

Of the above-mentioned genes, KRAS, EGER and BRAF genes are particularly preferable targets, since there are many patients to be the mutation detection targets, and their causal relationship with cancer is comparatively well-known.

Figure 1:
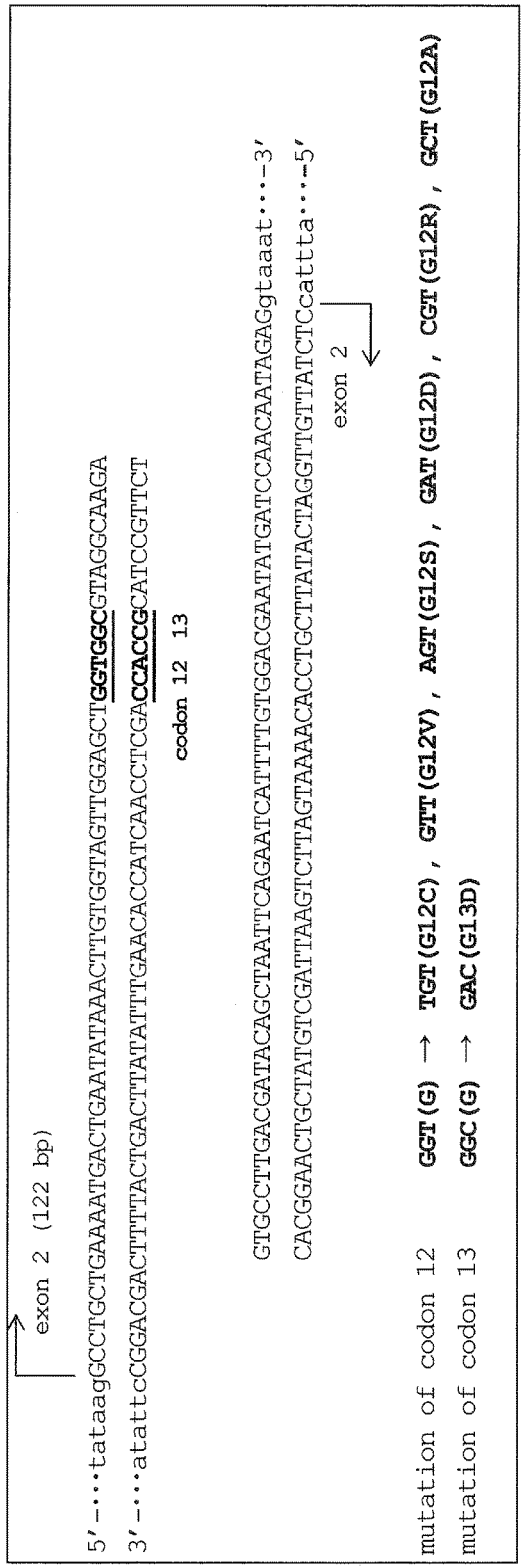
FIG. 1 shows the base sequence and main mutations of the second exon of KRAS gene.

The "difference in a base sequence" to be a detection target in the method of the present invention is any difference from the standard base sequence (i.e., base sequence of detection non-target nucleic acid). The difference in a base sequence may be caused by, for example, one or more mutations by substitution, insertion, deletion, inversion, overlap and translocation and the like or a combination thereof. Preferably, the difference in a base sequence is a mutation of a gene known to be related to the onset and/or treatment sensitivity of a particular disease. To be specific, for example, a mutation of the 12th codon or 13th codon of the second exon KRAS gene is known to be related to the response efficiency of a molecule target drug cetuximab, and the mutation includes, for example, the following (the base sequence of the second exon of KRAS gene (second exon corresponds to the 7- to 128-position of the base sequence shown in SEQ ID NO: 1) is shown in FIG. 1. SEQ ID NO: 2 shows the amino acid sequence encoded by the second exon).

mutation of 12th codon:
GGT(G)→TGT(C), GTT(V), AGT(S) GAT(D), CGT(R), GCT(A)

mutation of 13th codon:
GGC (G)→GAC (D)

In EGFR gene, plural mutations occur in the 18th exon to 21st exon, which are known to correlate with the response efficiency of molecule target drug gefitinib (see, for example, JP-A-2006-288353). As such mutation, for example, the following can be mentioned.

mutation of 18th exon:
G719C, G719S, G719A mutation of 19th exon:
E746-A750del (nt 2235-2249del),
E746-A750del (nt 2236-2250del),
L747-A750del T751S,
L747-S752del P753S,
L747-E749del A750P,
L747-S752del E746V,
S752-1759del mutation of 20th exon:
T790M, S768I mutation of 21st exon:
L858R, L861Q In BRAF gene, the mutation of the 600th codon of the 15th exon is known to correlate with the response efficiency of the molecule target drugs cetuximab and panitumumab. As such mutation, for example, the following can be mentioned.

mutation of 600th codon:
GTG(V)→GAG(E)

Each step is explained below.

(1) a step of selectively amplifying a region containing at least a part of the detection target site of the detection target nucleic acid in the test sample by a nucleic acid amplification method using a clamp nucleic acid having a base sequence complementary to the base sequence of the detection target site of a detection non-target nucleic acid In the present specification, the "detection target site" refers to a region in the target nucleic acid to be the detection target for a difference in a base sequence. For example, when the difference to be detected for is a difference in a single base (e.g., single base mutation), the detection target site may be the single base region or a vicinity of the single base region.

In the present specification, the "detection target nucleic acid" is a nucleic acid having a difference in a base sequence of the detection target site in the target nucleic acid, and generally means a nucleic acid having a base sequence different from a wild-type gene wherein the wild-type gene is the standard. A particular base sequence may be selected according to the test object, and the detection target nucleic acid may be a nucleic acid having the particular base sequence.

In the present specification, the "detection non-target nucleic acid" is a nucleic acid free of a difference in a base sequence of the detection target site in the target nucleic acid, and generally means a nucleic acid having the same base sequence as in the wild-type gene. A base sequence to be the standard may be selected according to the test object, and the detection non-target nucleic acid may be a nucleic acid having the standard base sequence.

In the present specification, the "clamp nucleic acid" is a nucleic acid that can hybridize to the detection target site of a detection non-target nucleic acid. Therefore, the clamp nucleic acid has a base sequence complementary to the base sequence of a detection target site in a detection non-target nucleic acid. In the method of the present invention, an oligonucleotide analog containing one or more kinds of one or more unit structures of a nucleoside analog represented by the following formula (I):

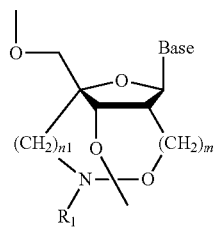

wherein

Base is a pyrimidine or purine nucleic acid base optionally having one or more substituents, $R_1$ is a hydrogen atom, an alkyl group, an alkenyl group, a cycloalkyl group, an aryl group, an aralkyl group, an acyl group, a sulfonyl group, a silyl group, or a functional molecule unit substituent, m is an integer of 0-2, and n1 is an integer of 1-3, the following formula (II):

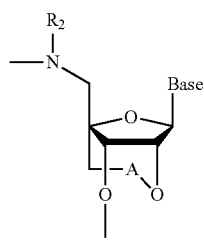

wherein

Base is as defined above,

A is a direct bond, an alkylene group having 1-4 carbon atoms, —O—$(CH_2)_{n2}$— (wherein the oxygen atom is bonded to the 4'-position methylene group, and n2 is an integer of 1-3), or —$N(R_3)$—$(CH_2)_{n3}$— (wherein the nitrogen atom is bonded to the 4'-position methylene group, and n3 is an integer of 1-3), $R_2$ and $R_3$ are the same or different and each is a hydrogen atom, a hydroxyl-protecting group for nucleic acid synthesis, an alkyl group, an alkenyl group, a cycloalkyl group, an aralkyl group, an aryl group, an acyl group, a silyl group, a phosphate group, a phosphate group protected with a protective group for nucleic acid synthesis, or —$P(R_4)R_5$ [where $R_4$ and $R_5$ are the same or different, and each is a hydroxyl group, a hydroxyl group protected with a protective group for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alky group having 1 to 5 carbon atoms], the following formula (III):

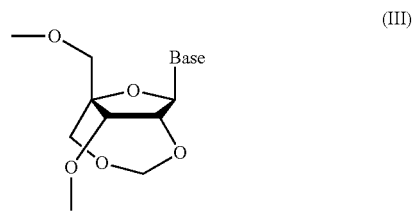

wherein Base is as defined above,
or the following formula (IV):

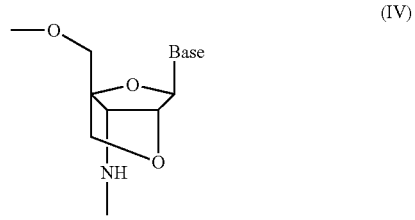

wherein Base is as defined above, (provided a binding form between respective nucleoside analogs in the oligonucleotide analogs optionally contains one or more phosphorothioate bonds in addition to a phosphodiester bond and, when two or more of one or more kinds of the aforementioned unit structures are contained, Base may be the same or different between the structures) or a salt thereof is used as the clamp nucleic acid. In the context of the explanation of the present invention, such oligonucleotide analog or a salt thereof is referred to as "BNA after the second generation" or simply "BNA".

In the formulas (I)-(IV), the pyrimidine or purine nucleic acid of Bases includes bases to be generally known as constituent elements of nucleic acids (for example, guanine, adenine, cytosine, thymine, uracil), and all other chemical structures which are similar thereto and which can act as, or can be used instead of, the bases constituting nucleic acids. Preferred examples are pyrimidine or purine nucleic acid bases, and pyrimidine or purine nucleic acid bases optionally having one or more substituents selected from the α group to be described below. Concretely, a purin-9-yl group, a 2-oxopyrimidin-1-yl group, or a purin-9-yl group or a 2-oxopyrimidin-1-yl group having a substituent selected from the following α group is preferred.

α group: a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom.

A group preferred as "the purine nucleic acid base optionally having the substituent" is a 6-aminopurin-9-yl (i.e. adeninyl) group, a 6-aminopurin-9-yl group having the amino group protected with a protective group for nucleic acid synthesis, a 2,6-diaminopurin-9-yl group, a 2-amino-6-chloropurin-9-yl group, a 2-amino-6-chloropurin-9-yl group having the amino group protected with a protective group for nucleic acid synthesis, a 2-amino-6-fluoropurin-9-yl group, a 2-amino-6-fluoropurin-9-yl group having the amino group protected with a protective group for nucleic acid synthesis, a 2-amino-6-bromopurin-9-yl group, a 2-amino-6-bromopurin-9-yl group having the amino group protected with a protective group for nucleic acid synthesis, a 2-amino-6-hydroxypurin-9-yl (i.e., guaninyl) group, a 2-amino-6-hydroxypurin-9-yl group having the amino group protected with a protective group for nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloroprolin-2-yl group, or a 6-mercaptopurin-9-yl group. More preferred is a 6-benzoylaminopurin-9-yl group, an adeninyl group, a 2-isobutyrylamino-6-hydroxypurin-9-yl group, or a guaninyl group.

A group preferred as "the pyrimidine nucleic acid base optionally having the substituent" is a 2-oxo-4-amino-1,2-dihydropyrimidin-1-yl (i.e., cytosinyl) group, a 2-oxo-4-amino-1,2-dihydropyrimidin-1-yl group having the amino group protected with a protective group for nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group having the amino group protected with a protective group for nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e., uracinyl) group, a 2-oxo-4-hydroxy-5-methyl-1,2-dihydropyrimidin-1-yl (i.e., thyminyl) group, or a 4-amino-5-methyl-2-oxo-1,2-dihydropyrimidin-1-yl (i.e., 5-methylcytosinyl) group. More preferred is a 2-oxo-4-benzoylamino-1,2-dihydropyrimidin-1-yl group, a cytosinyl group, a thyminyl group, a uracinyl group, a 2-oxo-4-benzoylamino-5-methyl-1,2-dihydropyrimidin-1-yl group, or a 5-methylcytosinyl group.

More preferred among "the purine or pyrimidine nucleic acid bases optionally having the substituent" is 6 aminopurin-9-yl (i.e. adeninyl), 6-aminopurin-9-yl having the amino group protected with a protective group for nucleic acid synthesis, 2,6-diaminopurin-9-yl group, 2 amino-6-chloropurin-9-yl, 2-amino-6-chloropurin-9-yl having the amino group protected with a protective group for nucleic acid synthesis, 2-amino-6-fluoropurin-9-yl, 2 amino-6-fluoropurin-9-yl having the amino group protected with a protective group for nucleic acid synthesis, 2 amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-2-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo-1,2-dihydropyrimidin-1-yl having the amino group protected with a protective group for nucleic acid synthesis.

The "protective group for a hydroxyl group for nucleic acid synthesis" as $R_2$ and $R_3$, and the "protective group in the "hydroxyl group protected with a protective group for nucleic acid synthesis" as $R_4$ and $R_5$ and in the α group are not limited, as long as they can protect the hydroxyl group stably during nucleic acid synthesis. Concretely, they refer to protective groups which are stable under acidic or neutral conditions, and which can be cleaved by a chemical method such as hydrogenolysis, hydrolysis, electrolysis, or photolysis. Examples of such protective groups are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, and unsaturated alkylcarbonyl groups such as (E)-2-methyl-2-butenoyl; "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl;

"lower alkenyl groups" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl; "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-4-yl, and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups", for example, lower trialkylsilyl groups such as trimethylsilyl, triethylsilyl, isopropyldimethylsilyl, t-butyldimethylsilyl, methyldiisopropylsilyl, methyldi-t-butylsilyl, and triisopropylsilyl, lower alkylsilyl groups substituted by one or two aryl groups, such as diphenylmethylsilyl, diphenylbutylsilyl, diphenylisopropylsilyl, and phenyldiisopropylsilyl; "lower alkoxymethyl groups" such as methoxymethyl, 1,1-dimethyl-1-methoxymethyl, ethoxymethyl, propoxymethyl, isopropoxymethyl, butoxymethyl, and tert-butoxymethyl; "lower alkoxylated lower alkoxymethyl groups" such as 2-methoxyethoxymethyl; "halogeno lower alkoxymethyl groups" such as 2,2,2-trichloroethoxymethyl and bis(2-chloroethoxy)methyl; "lower alkoxylated ethyl groups" such as 1-ethoxyethyl and 1-(isopropoxy)ethyl; "halogenated ethyl groups" such as 2,2,2-trichloroethyl; "methyl groups substituted by one to three aryl groups" such as benzyl, α-naphthylmethyl, β-naphthylmethyl, diphenylmethyl, triphenylmethyl, α-naphthyldiphenylmethyl, and 9-anthrylmethyl; "methyl groups substituted by one to three aryl groups having an aryl ring substituted by a lower alkyl, lower alkoxy, halogen, or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; "lower alkoxycarbonyl groups" such as methoxycarbonyl, ethoxycarbonyl, t-butoxycarbonyl, and isobutoxycarbonyl; "aryl groups substituted by a halogen atom, a lower alkoxy group, or a nitro group", such as 4-chlorophenyl, 2-fluorophenyl, 4-methoxyphenyl, 4-nitrophenyl, and 2,4-dinitrophenyl; "lower alkoxycarbonyl groups substituted by halogen or a lower trialkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by one or two lower alkoxy or nitro groups", such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl.

The "protective group for a hydroxyl group for nucleic acid synthesis", as $R_2$ and $R_3$, is preferably the "aliphatic acyl group", the "aromatic acyl group", the "methyl group substituted by one to three aryl groups", the "methyl group substituted by one to three aryl groups having an aryl ring substituted by a lower alkyl, lower alkoxy, halogen, or cyano group", or the "silyl group", more preferably an acetyl group, a benzoyl group, a benzyl group, a p-methoxybenzoyl group, a dimethoxytrityl group, a monomethoxytrityl group, or a tert-butyldiphenylsilyl group. The protective group in the "hydroxyl group protected with a protective group for nucleic acid synthesis", as $R_4$ and $R_5$ and in the α group, is preferably the "aliphatic acyl group", the "aromatic acyl group", the "methyl group substituted by one to three aryl groups", the "aryl group substituted by a halogen atom, a lower alkoxy group, or a nitro group", the "lower alkyl group", or the "lower alkenyl group", more preferably a benzoyl group, a benzyl group, a 2-chlorophenyl group, a 4-chlorophenyl group, or a 2-propenyl group.

The "alkyl group", as $R_1$, $R_2$ and $R_3$, refers to a straight chain or branched chain alkyl group having 1 to 20 carbon atoms, and includes a straight chain or branched chain alkyl group having 1 to 6 carbon atoms (such an alkyl group may herein be referred to as a lower alkyl group), such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl. The alkyl group also includes a straight chain or branched chain alkyl group having 7 to 20 carbon atoms, such as heptyl, octyl, is nonyl or decyl. Preferred is the above-mentioned straight chain or branched chain alkyl group having 1 to 6 carbon atoms.

Examples of the "alkylene group having 1-4 carbon atoms" for A include methylene, ethylene, trimethylene and tetramethylene groups. Preferred is a methylene group.

The "alkenyl group", as $R_1$, $R_2$ and $R_3$, refers to a straight chain or branched chain alkenyl group having 2 to 20 carbon atoms, and includes a straight chain or branched chain alkenyl group having 2 to 6 carbon atoms (such an alkenyl group may herein be referred to as a lower alkenyl group), such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl. The alkeyl group also includes geranyl and farnesyl, and is preferably the above-mentioned straight chain or branched chain alkenyl group having 2 to 6 carbon atoms.

The "cycloalkyl group", as $R_1$, $R_2$ and $R_3$, refers to a cycloalkyl group having 3 to 10 carbon atoms, and includes, for example, cyclopropyl, cyclobutyl, cyclopentyl, cyclohexyl, cycloheptyl, cyclooctyl, norbornyl, and adamantyl. Preferred is a cycloalkyl group having 3 to 8 carbon atoms, such as cyclopropyl, cyclobutyl, cyclopentyl, cyclohexyl, cycloheptyl, or cyclooctyl. The "cycloalkyl group" also includes a heterocyclic group in which one or more methylene groups on the ring of the cycloalkyl group have been substituted by oxygen atoms or sulfur atoms, or nitrogen atoms substituted by an alkyl group. An example of the heterocyclic group is a tetrahydropyranyl group.

The "aryl group", as $R_1$, $R_2$ and $R_3$, refers to a monovalent substituent having 6 to 14 carbon atoms which remains after removing one hydrogen atom from an aromatic hydrocarbon group, and includes, for example, phenyl, indenyl, naphthyl, phenanthrenyl, and anthracenyl. The aryl group may be substituted by one or more groups, such as a halogen atom, a lower alkyl group, a hydroxyl group, an alkoxy group, an aryloxy group, an amino group, a nitro group, trifluoromethyl, and a phenyl group. Examples of the optionally substituted aryl group are 2-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl, and biphenyl.

Preferred examples are a phenyl group, and a phenyl group substituted by a halogen atom, a lower alkoxy group, or a nitro group.

The "aralkyl group", as $R_1$, $R_2$ and $R_3$, refers to an alkyl group having 1 to 6 carbon atoms which has been substituted by an aryl group. Examples of the aralkyl group are "methyl groups substituted by one to three aryl groups", such as benzyl, α-naphthylmethyl, β-naphthylmethyl, indenylmethyl, phenanthrenylmethyl, anthracenylmethyl, diphenylmethyl, triphenylmethyl, α-naphthyldiphenylmethyl, and 9-anthrylmethyl, and "methyl groups substituted by one to three aryl groups having an aryl ring substituted by a lower alkyl, lower alkoxy, halogen, or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl. Other examples include "alkyl groups having 3 to 6 carbon atoms substituted by an aryl group", such as 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl. Preferred examples are the "methyl groups substituted by one to three aryl groups", and the "methyl groups substituted by one to three aryl groups having an aryl ring substituted by a lower alkyl, lower alkoxy, halogen, or cyano group". More preferred examples are 4-methoxyphenyldiphenylmethyl, and 4,4'-dimethoxytriphenylmethyl.

Examples of the "acryl group", as $R_1$, $R_2$ and $R_3$, are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, aryloxy lower alkylcarbonyl groups such as a phenoxyacetyl group, and unsaturated alkylcarbonyl groups such as (E)-2-methyl-2-butenoyl; and "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl. Preferred examples are formyl, acetyl, propionyl, butyryl, isobutyryl, pentanoyl, pivaloyl, benzoyl, and phenoxyacetyl groups.

As the "sulfonyl group", as $R_1$, there can be named "aliphatic sulfonyl groups", for example, sulfonyl groups substituted by a straight chain or branched chain alkyl group having 1 to 6 carbon atoms, such as methanesulfonyl and ethanesulfonyl, and "aromatic sulfonyl groups", for example, sulfonyl groups substituted by various aryl groups, such as benzenesulfonyl and p-toluenesulfonyl. Preferred examples are methanesulfonyl and p-toluenesulfonyl.

As the "silyl group", as $R_1$, $R_2$ and $R_3$, there can be named "lower trialkylsilyl groups" such as trimethylsilyl, triethylsilyl, isopropyldimethylsilyl, tert-butyldimethylsilyl, methyldiisopropylsilyl, methyldi-tert-butylsilyl, and triisopropylsilyl, "lower alkylsilyl groups substituted by one or two aryl groups", such as diphenylmethylsilyl, butyldiphenylbutylsilyl, diphenylisopropylsilyl, and phenyldiisopropylsilyl. Preferred examples are trimethylsilyl, triethylsilyl, triisopropylsilyl, t-butyldimethylsilyl, t-butyldiphenylsilyl. A more preferred example is trimethylsilyl.

The "protective group" in the "phosphate group protected with a protective group for nucleic acid synthesis" as $R_2$ and $R_3$ is not limited, as long as it can protect the phosphate group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "cyanated lower alkyl groups" such as 2-cyanoethyl, and 2-cyano-1,1-dimethylethyl; "ethyl groups substituted by a silyl group", such as 2-methyldiphenylsilylethyl, 2-trimethylsilylethyl, and 2-triphenylsilylethyl; "halogenated lower alkyl groups", such as 2,2,2-trichloroethyl, 2,2,2-tribromoethyl, 2,2,2-trifluoroethyl, and 2,2,2-trichloro-1,1-diemthylethyl; "lower alkenyl groups", such as ethenyl, 1-propenyl, 2-propenyl, 1-methyl-2-propenyl, 1-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl; "cycloalkyl groups", such as cyclopropyl, cyclobutyl, cyclopentyl, cyclohexyl, cycloheptyl, norbornyl, and adamantyl; "cyanated lower alkenyl groups" such as 2-cyanobutenyl; "aralkyl groups", such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl; "aralkyl groups having an aryl ring substituted by a nitro group or a halogen atom", such as 4-chlorobenzyl, 2-(4-nitrophenyl)ethyl, o-nitrobenzyl, 4-nitrobenzyl, 2,4-dinitrobenzyl, and 4-chloro-2-nitrobenzyl; "aryl groups", such as phenyl, indenyl, naphthyl, phenanthrenyl, and anthracenyl; and "aryl groups substituted by a lower alkyl group, a halogen atom, or a nitro group", such as 2-methylphenyl, 2,6-dimethylphenyl, 2-chlorophenyl, 4-chlorophenyl, 2,4-dichlorophenl, 2,5-dichiorophenyl, 2-bromophenyl, 4-nitrophenyl, and 4-chloro-2-nitrophenyl. Preferred examples are the "lower alkyl groups", "lower alkyl groups substituted by a cyano group", "aralkyl groups", "aralkyl groups having an aryl ring substituted by a nitro group or a halogen atom", or "aryl groups substituted by a lower alkyl group, a halogen atom, or a nitro group". A more preferred example is a 2-cyanoethyl group, a 2,2,2-trichloroethyl group, a benzyl group, a 2-chlorophenyl group, or a 4-chlorophenyl group.

The "functional molecule unit substituent" as $R_1$ includes labeling molecules (for example, molecular species including fluorescent molecule, chemiluminescent molecule and radioactive isotope).

The protective group in "the mercapto group protected with a protective group for nucleic acid synthesis" as $R_4$ and $R_5$ and in the α group is not limited, as long as it can protect the mercapto group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are those named above as the protective group for the hydroxyl group, as well as "disulfide-forming groups", for example, alkylthio groups such as methylthio, ethylthio, and tert-butylthio, and arylthio groups such as benzylthio. Preferred examples are "aliphatic acyl groups" or "aromatic acyl groups". More preferred examples are a benzoyl group and a benzyl group.

Examples of "the alkoxy group having 1 to 5 carbon atoms" as $R_4$ and $R_5$ and in the α group in the general formula (I) or (II) are methoxy, ethoxy, n-propoxy, isopropoxy, n-butoxy, isobutoxy, s-butoxy, tert-butoxy, and n-pentoxy. A preferred example is a methoxy or ethoxy group.

Examples of "the alkylthio group having 1 to 5 carbon atoms" as $R_4$ and $R_5$ and in the α group are methylthio, ethylthio, propylthio, isopropylthio, butylthio, isobutylthio, s-butylthio, tert-butylthio, and n-pentylthio. A preferred example is a methylthio or ethylthio group.

Examples of "the cyanoalkoxy group having 1 to 6 carbon atoms" as $R_4$ and $R_5$ are the above "alkoxy groups having 1 to 5 carbon atoms" which have been substituted by a cyano group. Such groups are, for example, cyanomethoxy, 2-cyanoethoxy, 3-cyanopropoxy, 4-cyanobutoxy, 3-cyano-2-methylpropoxy, and 1-cyanomethyl-1,1-dimethylmethoxy. A preferred example is a 2-cyanoethoxy group.

Examples of "the amino group substituted by an alkyl group having 1 to 5 carbon atoms", as $R_4$ and $R_5$ and in the α group, are methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino, and di(tert-butyl)amino. A preferred example is methylamino, ethylamino, dimethylamino, diethylamino, or diisopropylamino group.

As the "alkyl group having 1 to 5 carbon atoms" in the α group, there can be named, for example, methyl, ethyl, propyl, isopropyl, isopropyl, butyl, isobutyl, s-butyl, tert-butyl, and n-pentyl. A preferred example is a methyl or ethyl group.

As the "halogen atom" in the α group, there can be named, for example, a fluorine atom, a chlorine atom, a bromine atom, and an iodine atom. A preferred example is a fluorine atom or a chlorine atom.

The protective group in the "amino group protected with a protective group for nucleic acid synthesis" in the α group is not limited, as long as it can protect the amino group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, and unsaturated alkylcarbonyl groups such as (E)-2-methyl-2-butenoyl; "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "lower alkoxycarbonyl groups" such as methoxycarbonyl, ethoxycarbonyl, t-butoxycarbonyl, and isobutoxycarbonyl; "lower alkoxycarbonyl groups substituted by halogen or a lower trialkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by one or two lower alkoxy or nitro groups", such as benzyloxycarbonyl, 4-methoxybenzyloxycarbonyl, 2-nitrobenzyloxycarbonyl, and 4-nitrobenzyloxycarbonyl. A preferred example is the "aliphatic acyl group" or "aromatic acyl group", and a more preferred example is a benzoyl group.

The "nucleoside analogue" refers to a nonnatural type of "nucleoside" consisting of a purine or pyrimidine base and a sugar linked together, or a product consisting of an aromatic heterocyclic ring or an aromatic hydrocarbon ring, which is other than purine and pyrimidine and which can be used instead of the purine or pyrimidine base, and a sugar linked together.

The "oligonucleotide analogue" refers to a nonnatural type derivative of "oligonucleotide" comprising 2 to 50 identical or different "nucleosides" or "nucleoside analogues" linked together by phosphodiester bonds, or one or more phosphorothioate bonds possibly. Preferred examples of such an analogue are sugar derivatives with the sugar portion modified; thioate derivatives formed upon thioation of the phosphodiester portion; esters formed upon esterification of the terminal phosphoric acid portion; and amides formed upon amidation of the amino group on the purine base. More preferred examples are sugar derivatives with the sugar portion modified.

The "salt thereof" refers to a salt of the above-mentioned oligonucleotide analogue, because the oligonucleotide can be converted into the salt. Preferred examples of the salt are metal salts, for example, alkali metal salts such as sodium salt, potassium salt, and lithium salt, alkaline earth metal salts such as calcium salt and magnesium salt, aluminum salt, iron salt, zinc salt, copper salt, nickel salt, and cobalt salt; amine salts, for example, inorganic salts such as ammonium salt, and organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, and tris(hydroxymethyl)aminomethane salt; inorganic acid salts, for example, halogenated hydroacid salts such as hydrofluoride, hydrochloride, hydrobromide, and hydriodide, nitrate, perchlorate, sulfate, and phosphate; organic acid salts, for example, lower alkanesulfonates such as methanesulfonate, trifluoromethanesulfonate, and ethanesulfonate, arylsulfonates such as benzenesulfonate and p-toluenesulfonate, acetate, malate, fumarate, succinate, citrate, tartrate, oxalate, and maleate; and amino acid salts such as glycine salt, lysine salt, arginine salt, ornithine salt, glutamate, and aspartate.

Of the oligonucleotide analogs containing one or more unit structures of the nucleoside analogs represented by any of the formulas (I)-(IV), and a salt thereof, which are used as clamp nucleic acids, preferred includes an oligonucleotide analog containing one or more unit structures of nucleoside analogs represented by the formula (I) and a salt thereof, and an oligonucleotide analog containing one or more unit structures of nucleoside analogs represented by the formula (II) and a salt thereof. More preferred is an oligonucleotide analog containing one or more unit structures of nucleoside analogs represented by the formula (I) or a salt thereof.

Of the nucleoside analogs represented by the formula (I), preferred is one wherein Base is a pyrimidine or purine nucleic acid base optionally having one or more substituents selected from the above-mentioned α group, and $R_1$ is a hydrogen atom, an alkyl group having 1 to 5 carbon atoms, an aralkyl group such as a benzyl group and the like, a lower aliphatic or aromatic acyl group such as an acetyl group, a benzoyl group and the like, or an aliphatic or aromatic sulfonyl group such as a methanesulfonyl group, a p-toluenesulfonyl group and the like. In the nucleoside analog, Base is preferably selected from the following β group and γ group, and more preferably selected from γ group.

β group: a 6-aminopurin-9-yl (i.e. adeninyl) group, a 6-aminopurin-9-yl group having the amino group protected with a protective group for nucleic acid synthesis, a 2,6-diaminopurin-9-yl group, a 2-amino-6-chloropurin-9-yl group, a 2-amino-6-chloropurin-9-yl group having the amino group protected with a protective group for nucleic acid synthesis, a 2-amino-6-fluoropurin-9-yl group, a 2-amino-6-fluoropurin-9-yl group having the amino group protected with a protective group for nucleic acid synthesis, a 2-amino-6-bromopurin-9-yl group, a 2-amino-6-bromopurin-9-yl group having the amino group protected with a protective group for nucleic acid synthesis, a 2-amino-6-hydroxypurin-9-yl (i.e., guaninyl) group, a 2-amino-6-hydroxypurin-9-yl group having the amino group protected with a protective group for nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e., cytosinyl) group, a 2-oxo-4-amino-1,2-dihydropyrimidin-1-yl group having the amino group protected with a protective group for nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group having the amino group protected with a protective group for nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e., uracinyl) group, a 2-oxo-4-hydroxy-5-methyl-1,2-dihydropyrimidin-1-yl (i.e., thyminyl) group, a 4-amino-5-methyl-2-oxo-1,2-dihydropyrimidin-1-yl (i.e., 5-methylcytosinyl) group, or 4-amino-5-methyl-2-oxo-1,2-dihydropyrimidin-1-yl having the amino group protected with a protective group for nucleic acid synthesis;

γ group: a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl, or thyminyl group.

Of the nucleoside analogs represented by the formula (I), particularly preferred is one wherein Base is a pyrimidine or purine nucleic acid base optionally having one or more substituents selected from the above-mentioned α group, $R_1$ is a methyl group, m is 0, and n1 is 1. In the nucleoside analogs, Base is preferably selected from the above-mentioned β group and γ group, and more preferably selected from γ group.

Of the nucleoside analogs represented by the formula (II), preferred is one wherein Base is a pyrimidine or purine nucleic acid base optionally having one or more substituents selected from the above-mentioned α group, A is a direct bond or —O—$CH_2$— (wherein the oxygen atom is bonded to the 4'-position methylene group), and $R_1$ is a hydrogen atom, an aliphaticacyl group, an aromatic acyl group, a methyl group substituted by 1 to 3 aryl groups, a methyl group substituted by 1 to 3 aryl groups wherein the aryl ring is substituted by lower alkyl, lower alkoxy, halogen or a cyano group, or a silyl group. More preferred is one wherein Base is a pyrimidine or purine nucleic acid base optionally having one or more substituents selected from the above-mentioned α group, A is a direct bond or —O—CH$_2$— (wherein the oxygen atom is bonded to the 4'-position methylene group), and R$_1$ is a hydrogen atom, an acetyl group, a benzoyl group, a benzyl group, a p-methoxybenzyl group, a dimethoxytrityl group, a monomethoxytrityl group or a Cert-butyldiphenylsilyl group. In these nucleoside analogs, Base is preferably selected from the above-mentioned β group and γ group, and more preferably selected from γ group.

Of the nucleoside analogs represented by the formula (II), particularly preferred is one wherein Base is a pyrimidine or purine nucleic acid base optionally having one or more substituents selected from the above-mentioned α group, A is a direct bond or —O—CH$_2$— (wherein the oxygen atom is bonded to the 4'-position methylene group), and R$_1$ is a hydrogen atom. In these nucleoside analogs, Base is preferably selected from the above-mentioned β group and γ group, and more preferably selected from γ group.

Of the nucleoside analogs represented by the formula (III), preferred is one wherein Base is a pyrimidine or purine nucleic acid base optionally having one or more substituents selected from the above-mentioned α group. In these nucleoside analogs, Base is preferably selected from the above-mentioned β group and γ group, and more preferably selected from γ group.

Of the nucleoside analogs represented by the formula (IV), preferred is one wherein Base is a pyrimidine or purine nucleic acid base optionally having one or more substituents selected from the above-mentioned α group. In these nucleoside analogs, Base is preferably selected from the above-mentioned β group and γ group, and more preferably selected from γ group.

The length of the oligonucleotide analogs of the clamp nucleic acid is generally 5-30 mer, preferably 5-25 mer, more preferably 10-18 mer. Generally, when the length of the clamp nucleic acid is elongated, the binding ability to a wild-type base sequence becomes stronger; however, the base recognition ability (i.e., difference between binding ability to a wild-type base sequence and binding ability to a one-base mismatch sequence) tends to be weak. To achieve detection with high sensitivity and accuracy, it is important to appropriately determine the length of the clamp nucleic acid.

While the number of the nucleoside analogs in the oligonucleotide analogs is not particularly limited as long as it is not less than one, it is preferably set to the highest possible number since the binding ability to a wild-type base sequence and base recognition ability can be potentiated by the introduction of nucleoside analogs. It is particularly preferable to have a nucleoside analog at the site on the clamp nucleic acid, which corresponds to the difference to be detected. As the nucleoside other than the nucleoside analogs in the clamp nucleic acid, a natural nucleoside is used. The natural nucleoside includes adenosine, deoxyadenosine, guanosine, deoxyguanosine, 5-methyluridine, thymidine, cytidine, deoxycytidine, uridine, deoxyuridine and the like. When the clamp nucleic acid is 13 mer, a preferable number of nucleoside analogs is, for example, 5-10, more preferably 7-9, though the number is not limited thereto.

The binding form between respective nucleosides and/or nucleoside analogs in the oligonucleotide analogs may be a phosphodiester bond, and may contain one or more phosphorothioate bonds to impart a nuclease resistance effect.

The terminals may be appropriately modified, for example, the 5'-terminal of the clamp nucleic acid is modified by substituting with 2'-OMe-RNA or the above-mentioned nucleoside analogs, and/or the 3'-terminal is monophosphorylated, and the like. In addition, to prevent elongation reaction by PCR, 3 mismatched bases (e.g., GGG) may be added to the 3'-terminal.

The sequence and length of the clamp nucleic acid, and the number of the nucleoside analogs are factors that determine a binding ability to a detection target site of the clamp nucleic acid, namely, Tm value. To achieve a sufficient clamp effect in the nucleic acid amplification reaction in this step, it is also important to appropriately determine the Tm value of the clamp nucleic acid in consideration of the properties of the reagents to be used for the nucleic acid amplification and the like.

The clamp nucleic acid can be synthesized based on documents such as JP-A-2001-89496, WO 2003/068795, WO 2005/021570 and the like. Alternatively, synthesis of the clamp nucleic acid may be committed to a trader entrusted with synthesis of RNA oligonucleotide.

In this step, the aforementioned clamp nucleic acid and a nucleic acid in a test sample are co-present in a reaction mixture for nucleic acid amplification, and a nucleic acid amplification reaction is performed.

The nucleic acid amplification method to be used in this step is not limited as long as it can amplify a detection target site and can selectively inhibit the amplification by the binding of a clamp nucleic acid. For example, PCR method [not only PCR method based on the most basic principles, but also various variations developed based thereon such as quantitative PCR methods such as hot start PCR method, multiplex PCR method, nested PCR method, RT-PCR method, real-time PCR method, digital PCR method and the like, and the like], NASBA (Nucleic Acid Sequence-Based Amplification) method/JP-B-2650159, TMA (Transcription-Mediated Amplification) method/JP-B-3241717, TRC (Transcription Reverse Transcription Concerted Reaction) method/JP-A-2000-14400, LAMP (Loop-mediated Isothermal Amplification) method/WO00/28082, ICAN method (Isothermal and Chimeric primer-initiated Amplification of Nucleic acids) method/JP-B-3433929, LCR (Ligase Chain Reaction) method/EP application No. 320328, SDA (Strand Displacement Amplification) method/JP-B-7-114718, and the like can be used. Since PCR method is a nucleic acid amplification method used most widely, various reagents and instruments optimized for the method are easily available, as well as methods with many variations are available as mentioned above, and utility is extremely high. Therefore, it can be mentioned as a preferable method for this step. The conditions, operation and the like of nucleic acid amplification reaction including PCR may be those of conventional methods generally performed in this field.

The above-mentioned reaction mixture for nucleic acid amplification is a solution containing reagents and the like necessary for performing the aforementioned nucleic acid amplification reaction. While the composition of the reaction mixture for the nucleic acid amplification varies somewhat depending on the nucleic acid amplification method to be used, generally, 4 kinds of deoxynucleoside triphosphates as substrates (dATP, dTTP, dCTP, dGTP: hereinafter collectively dNTP), DNA polymerase as an enzyme, magnesium ion as a cofactor of the aforementioned enzyme, and an amplification primer as a primer for elongation are basically contained in a buffer. While the detail is mentioned below, a method such as real-time PCR method and the like capable of performing this step and a step of detecting the amplified nucleic acid altogether is used as a nucleic acid amplification method, a suitable detection reagent such as intercalator, fluorescence labeling probe, cycling probe and the like is also co-present in the reaction mixture for nucleic acid amplification. As the concentration of dNTP, an optimal final concentration of each of the 4 kinds should fall within the range of 100-400 μm. A DNA polymerase having properties suitable for the nucleic acid amplification method to be used is used. For PCR method, for example, heat-resistant DNA polymerases such as Taq DNA polymerase, Pfu DNA polymerase, those developed by companies relating to biosciences and the like are preferably used. As the concentration of the magnesium ion, an optimal final concentration should fall within the range of 1-6 mM.

The above-mentioned amplification primer is a primer used for amplifying a detection region by the aforementioned nucleic acid amplification method. An amplification primer is composed of nucleic acids such as DNA, RNA and the like, or modified nucleic acids such as LNA, BNA and the like, or a combination thereof. As the concentration of the amplification primer, an optimal final concentration should fall within the range of 20 nM to 2 μM. The number of the amplification primer is not particularly limited as long as the detection region can be amplified by the aforementioned nucleic acid amplification method. The base number of the amplification primer is generally within the range of 5-40 bases, preferably 15-30 bases, more preferably 18-25 base. The distance between amplification primers, i.e., detection region, is generally within the range of 50-5000 bases, preferably 100-2000 bases. The sequence of the amplification primer is not particularly limited as long as it can amplify a detection region containing at least a part of the detection target site, preferably a particular site where a difference in the base sequence is to be detected, by the aforementioned nucleic acid amplification method, and the Tm value is generally within the range of 50° C. to 65° C., preferably 55° C. to 60° C. A detection target site may be contained in the sequence of the primer. The sequence of the amplification primer may be designed manually, or a suitable software for primer design may be used. For example, Primer3 software (http://frodo.wi.mit.edu) and the like may be used.

The above-mentioned buffer has an optimal pH and an optimal salt concentration that afford the aforementioned activity of the DNA polymerase. It may further contain ribonuclease H (RNaseH), reverse transcriptase (RT) and the like depending on the nucleic acid amplification method to be used. While various types of the reaction mixture for the nucleic acid amplification are commercially available for the reactions of respective nucleic acid amplification methods, such commercially available one attached to a kit may also be used. When Taq DNA polymerase is used as an enzyme, one exemplary basic composition of the reaction mixture for the gene amplification is 10 mM Tris-HCl (pH 8.3)/50 mM KCl/2 mM MgCl$_2$/2.5U Taq DNA polymerase. It is needless to say that the conditions are not limited thereto.

As the amount of the nucleic acid to be the template in the reaction mixture, any amount is sufficient as long as it corresponds to generally $10^2$-$10^6$ molecules; for example, it is about 0.3 ng-3 μg for human gene. When the amount of the template is too high, the frequency of non-specific amplification increases. Therefore, the amount of the nucleic acid to be added to the reaction mixture is preferably suppressed to 0.5 μg or below per 100 μg.

As the amount of the clamp nucleic acid of the reaction mixture, since wild-type nucleic acid is generally in a large majority relative to mutated nucleic acid in a test sample, it is preferably added in a slight excess.

The aforementioned nucleic acid amplification reaction is performed in the aforementioned reaction mixture containing nucleic acid in a test sample and clamp nucleic acid. The clamp nucleic acid strongly binds to a complementary sequence present in a detection non-target nucleic acid, and inhibits annealing of primer and/or elongation of primer during the amplification reaction. On the other hand, the clamp nucleic acid used in the present invention shows high base recognition ability, and the presence of mismatch in even a single base drastically decreases the binding ability to the template, which allows for amplification of the detection target nucleic acid according to conventional amplification reaction. As a result, a detection region containing at least a part of the detection target site in the detection target nucleic acid is selectively amplified.

(2) Step of Detecting the Amplified Nucleic Acid

In this step, the detection region of the nucleic acid amplified in the aforementioned step (1) is detected. For detection, any method can be used as long as it can confirm amplification of the detection region of the detection target nucleic acid. The detection method is largely divided into a method of detecting the final product of an amplification reaction, and a method of confirming amplification over time during the amplification reaction. For both groups, results with higher reliability can be obtained by comparison with the results of each suitable control. In addition, more accurate results can be obtained by confirming the base sequence of the detection target site in the amplification product by a direct sequence method and the like.

Examples of the method for detecting the final product of the amplification reaction include a method including a deproteinization treatment of the solution after amplification reaction with a phenol-chloroform (1:1) solution, purification of the aqueous layer directly or using ethanol precipitation or a suitable purification kit, and measurement of the absorbance at wavelength 260 nm by an absorption spectrophotometer; a method including development of the amplification product on an agarose gel or polyacrylamide gel by electrophoresis, and detection by the southern hybridization method using a suitable probe; a method including detection by the chromatohybridization method using gold nanoparticles; a method including measurement of turbidity of a solution of the amplified nucleic acid; a method including fluorescence labeling of the 5'-terminal of the amplification primer in advance, electrophoresis using agarose gel or polyacrylamide gel after the amplification reaction, capture of fluorescence luminescence on an imaging plate, and detection using a suitable detection apparatus and the like.

As a method for confirming amplification over time during the amplification reaction, a method including detecting, over time, an increase in the fluorescence intensity reflecting an increase in the amplification product can be mentioned. To be specific, for example, real-time PCR method such as the intercalator method (Higuchi et al., BioTechnology 10, 413-417 (1992)), the TaqMan™ probe method (U.S. Pat. Nos. 5,210,015, 5,538,848), the cycling probe method (Bekkaoui et al., Biotechniques 20, 240-248 (1996)) and the like can be mentioned, and the TaqMan™ probe method and the cycling probe method are preferable since they are superior in the detection sensitivity and accuracy. For the real-time PCR method, an exclusive apparatus integrating a thermal cycler and a spectrofluorophotometer is necessary. As such apparatus, for example, StepOnePlus (ABI), LightCyclerNano (Roche) and the like can be mentioned.

As the detection method preferably used in this step, a method using a detection probe which is a single strand nucleic acid having a base sequence completely complementary to the base sequence of a region containing a particular site in which a difference in the base sequence is to be detected in the detection target nucleic acid can be mentioned. To be specific, for example, it is a method using a probe designed to have such base sequence in the southern hybridization method, TaqMan™ probe method, cycling probe method and the like.

Intercalator is a reagent that specifically binds between base pairs of double stranded nucleic acid and emits fluorescence, and emits fluorescence when excitation light is irradiated. The amount of the primer elongation product can be known based on the detection of fluorescence intensity derived from the intercalator. In the present invention, any intercalator generally used in the field can be used, for example, SYBR™ Green I (Molecular Probe), ethidium bromide, fluorene and the like.

The TaqMan™ probe method is a method for highly sensitively and quantitatively detecting the object trace nucleic acid by real-time PCR method using an oligonucleotide probe that hybridizes to a particular region of the target nucleic acid, wherein one terminal (generally, 5'-terminal) is labeled with a fluorescence group (reporter) and the other terminal (generally, 3'-terminal) is labeled with a quenching group. In the probe in a normal state, the fluorescence of the reporter is suppressed by a quenching group. While completely hybridizing this fluorescence probe to the detection region, PCR is performed from the outside thereof by using a DNA polymerase. When an elongation reaction by DNA polymerase proceeds, the exonuclease activity thereof causes hydrolysis of the fluorescence probe to liberate a reporter dye, whereby fluorescence is emitted. The initial level of the nucleic acid to be the template can be accurately quantified by real-time monitoring of the fluorescence intensity.

A probe to be used in the present invention is a fluorescence labeling probe containing a base sequence of a primer elongation product predicted to be amplified when real-time PCR is performed. In general, when the length of a probe is elongated, the binding ability to a complementary sequence becomes stronger, and therefore, a certain level of length is necessary. However, when the probe becomes long, the base specificity tends to become low, and therefore, the length should not be too long. The length of the specific probe is generally 5-40 mer, preferably 8-35 mer, more preferably 10-25 mer. The probe is constituted of nucleic acids such as DNA, RNA and the like, or modified nucleic acids such as LNA, BNA and the like, or a combination thereof. As mentioned above, since BNA is superior to DNA, RNA and the like in the binding ability to a complementary sequence, base recognition ability, and resistance to degrading enzymes, the probe preferably contains the unit structure of BNA. As a preferable unit structure (i.e., nucleoside analog) when the probe contains the unit structure of BNA, those mentioned above for clamp nucleic acid can be applied. When a probe having a base sequence completely complementary to a region containing a particular site in which a difference in the base sequence is to be detected in the detection target nucleic acid is used, a region in a probe corresponding to the region is preferably the unit structure of BNA.

Examples of the above-mentioned reporter fluorescent substance include carboxyfluorescein (FAM), hexachlorofluorescein (HEX), tetrachlorofluorescein (TET), Cy5 (Amersham Biosciences, Inc.) and the like. Of these, FAM is preferable. Examples of the quencher dye include fluorescent substances such as carboxytetramethylrhodamine (TAMRA) and the like, non-fluorescent substances such as Black Hole Quencher dye (e.g., BHQ2), 4-((4-(dimethylamino)phenyl)azo)benzoic acid (DABCYL) and the like. Of these, TAMRA is preferable.

The probe can be prepared based on the above-mentioned U.S. Pat. Nos. 5,210,015 and 5,538,848, or the above-mentioned documents regarding the synthesis of clamp nucleic acid and the like. Alternatively, synthesis committed to a suitable trader may be utilized.

The cycling probe method is a highly sensitive detection method by a combination of a chimera probe composed of RNA and DNA and RNase H. One side of the probe across the RNA region is labeled with a fluorescent substance (reporter) and the other is labeled with a substance that quenches fluorescence (quencher). While the probe in an intact state does not emit fluorescence on quenching, when RNA region is cleaved by RNase H after forming a hybrid of the sequence with a complementary amplification product, a strong fluorescence is emitted. The level of the amplification product can be monitored by measuring the fluorescence intensity. When a mismatch exists near RNA of cycling probe, cleavage by RNase H does not occur. Therefore, very highly specific detection capable or recognizing a difference even in a single base is possible.

A cycling probe can be obtained by committing design and synthesis thereof to a suitable trader.

(Kit for Mutation Detection)

The present invention also provides a kit that can be used for practicing the method of the present invention (hereinafter to be also referred to as the kit of the present invention). The kit of the present invention contains (a) a clamp nucleic acid having a base sequence complementary to the base sequence of the detection target site of a detection non-target nucleic acid, and (b) a reagent for selectively amplifying a region containing at least a part of the detection target site of the detection target nucleic acid in the test sample.

Preferable embodiments and specific examples of the clamp nucleic acid of the above-mentioned (a) are as explained for the method of the present invention.

While the reagent of the above-mentioned (b) is a reagent for performing the nucleic acid amplification method, as explained for the method of the present invention, the kit of the present invention may not necessarily contain all reagents essential for performing the amplification method.

The kit of the present invention preferably contains the aforementioned amplification primer as the reagent of (b). The amplification primer is typically an amplification primer for PCR.

The kit of the present invention can further contain one or more of nucleoside triphosphate, nucleic acid synthase, and buffer for amplification reaction. The nucleoside triphosphate is a substrate according to nucleic acid synthase (dNTP, rNTP etc.). The nucleic acid synthase is an enzyme according to a nucleic acid amplification method for which the kit is used, and includes suitable DNA polymerase, RNA polymerase, reverse transcriptase and the like. Examples of the buffer for amplification reaction include buffers used for performing general nucleic acid amplification reaction and hybridization reaction such as tris buffer, phosphate buffer, veronal buffer, borate buffer, Good's buffer and the like. While the pH is not particularly limited, it is generally preferably within the range of 5-9.

The kit of the present invention can also contain a reagent for performing a detection method such as those explained for the method of the present invention. Preferable examples of the reagent include intercalator, fluorescence labeling probe, cycling probe and the like, which are used for the above-mentioned real-time PCR. In addition, reagents that do not inhibit the stability of the co-existing reagents and the like, and do not inhibit nucleic acid amplification reaction and hybridization reaction may also be contained, such as stabilizer, preservative and the like. The concentration of these may be appropriately selected from the concentration range generally used in the field.

The present invention is explained in more detail in the following by referring to Examples, which are not to be construed as limitative.

EXAMPLES (Material and an Apparatus)

Various oligonucleotides used in the Examples are shown in Tables 1-1 and 1-2. Synthesis of these oligonucleotides was committed to GeneDesign Inc., Greiner-Japan Co., Ltd., Biologica Co. and the like. The BNA used has the above-mentioned nucleoside analog of the formula (I) wherein $R_1$ is a methyl group, m is 0, and n1 is 1 as a unit structure.

TABLE 1-1 various oligonucleotides for KRAS gene mutation test

| oligo kind | oligo name | sequence (5'→3') and chemical modification | length (mer) | SEQ ID NO: |
|---|---|---|---|---|
| Forward primer | Oligo 1 | actgaatataaacttgtggtag | 22 | 3 |
| Reverse primer | Oligo 2 | attgttggatcatattcgtc | 20 | 4 |
| nucleic acid amplification probe | Oligo 3 | F-cttgacgatacagctaattcagaatcat-R | 28 | 5 |
| nucleic acid amplification probe | Oligo 3-2 | J-cttgacgatacagctaattcagaatcat-R | 28 | 6 |
| 10 mer BNA clamp | Oligo 4 | CgCCACCAgC-P | 10 | 7 |
| 10 mer BNA clamp | Oligo 4-2 | CGCCACCAGC-P | 10 | 19 |
| 13 mer BNA clamp | Oligo 5 | taCgCCACCAgCt-P | 13 | 8 |
| 18 mer BNA clamp | Oligo 6 | gccTaCgCCaCCagCtcc-P | 18 | 9 |
| 10 mer LNA clamp | Oligo 7 | CgCCACCAgC-P | 10 | 10 |
| 13 mer DNA clamp | Oligo 8 | tacgccaccagct-P | 13 | 11 |
| 13 mer LNA clamp | Oligo 9 | taCgCCACCAgCt-P | 13 | 12 |
| 13 mer PNA clamp | Oligo 10 | tacgccaccagct | 13 | 13 |
| 18 mer DNA clamp | Oligo 11 | gcctacgccaccagctcc-P | 18 | 14 |
| 18 mer LNA clamp | Oligo 12 | gccTaCgCCaCCagCtcc-P | 18 | 15 |
| 18 mer PNA clamp | Oligo 13 | gcctacgccaccagctcc | 18 | 16 |
| G12V detection DNA probe | Oligo 14 | F-tacgccaacagctcc-R | 15 | 17 |
| G12V detection DNA probe | Oligo 14-2 | F-caacagctcc-R | 10 | 20 |
| G12V detection BNA probe | Oligo 15 | F-tacgccaAcagctcc-R | 15 | 18 |
| G12V detection BNA probe | Oligo 15-2 | F-caAcAgCtCc-R | 10 | 21 |
| G12D detection DNA probe | Oligo 16 | F-tacgccatcagctcc-R | 15 | 22 |
| G13D detection DNA probe | Oligo 17 | F-tacgtcaccagctcc-R | 15 | 23 |
| G12A detection DNA probe | Oligo 18 | F-tacgccagcagctcc-R | 15 | 24 |
| G12C detection DNA probe | Oligo 19 | F-tacgccacaagctcc-R | 15 | 25 |
| G12S detection DNA probe | Oligo 20 | F-tacgccactagctcc-R | 15 | 26 |
| G12R detection DNA probe | Oligo 21 | F-tacgccacgagctcc-R | 15 | 27 | a, c, g, t = DNA-A, -C, -G, -T
A, C, G, T = LNA-A, -$^m$C, -G, -T; t, c, g = 2'-OMe-RNA-U, -C, -G
A, C, G, T = 2',4'-BNA$^{NC}$ (N—Me) -A, -$^m$C, -G, -T; a, c, g, t = PNA-A, -C, -G, -T
F = FAM; J = JOE; R = TAMRA; P = monophosphorylation

TABLE 1-2

Various oligonucleotides for EGFR gene mutation test

| oligo kind | oligo name | sequence (5'→3') and chemical modification | length (mer) | SEQ ID NO: |
|---|---|---|---|---|
| Forward primer | Oligo 22 | tggcaccatctcacaattgc | 20 | 28 |
| Reverse primer | Oligo 23 | acacagcaaagcagaaactc | 20 | 29 |
| nucleic acid amplification probe | Oligo 24 | J-ccgaaagccaacaaggaaatcctcga-R | 26 | 30 |
| BNA clamp | Oligo 25 | g*TT*gc*TTCTCT*taat*T*c*C*-P | 18 | 31 |
| DNA probe for E746-A750 del (Type 1) detection | Oligo 26 | F-tcccgtcgctatcaaaacatct-R | 22 | 32 |
| LNA clamp | Oligo 27 | gTTgcTTCTCTtaatTcC-P | 18 | 33 |
| PNA clamp | Oligo 28 | gttgcttctcttaattcc | 18 | 34 |
| DNA clamp | Oligo 29 | gttgcttctcttaattcc-P | 18 | 35 | a, c, g, t = DNA-A, -C, -G, -T; *C*, *T* = 2',4'-BNA$^{NC}$(N-H)-$^m$C, -T
C, T = LNA-$^m$C, -T; *g* = 2'-OMe-RNA-G; a, c, g, t = PNA-A, -C, -G, -T
F = FAM; J = JOE; R = TAMRA; P = monophosphorylation

[Example 1] Detection Experiment 1 of KRAS Gene G12V Mutation in Model Test Sample (Clamp Effect of Various BNA Oligonucleotides)

(1) Test Sample

Commercially available human genomic DNA was used as a wild-type gene sample of KRAS gene and a DNA extracted from SW480-cultured cells was used as a G12V mutated gene sample. The amount of each DNA was determined from the UV spectrum of each sample and Ct value obtained by real-time PCR using oligo 1, 2 and 3 as forward primer, reverse primer and nucleic acid amplification probe. Based on the DNA amount thereof, model test samples having a mutation type of 100%, 10%, 1.0%, 0.1%, 0.01% or 0% were produced, and the respective model test samples were used in an amount of 50 ng per each experiment.

(2) Nucleic Acid Amplification Apparatus and Reagent for Nucleic Acid Amplification StepOnePlus (manufactured by ABI) was used as a real-time PCR apparatus and TaqMan™ Fast Advanced Master Mix (manufactured by ABI) was used as the reagents for nucleic acid amplification. The amount of the reagent to be used was in accordance with the attached manual.

(3) Primer, Nucleic Acid Amplification Probe, and Clamp Nucleic Acid

Oligo 1 and oligo 2 (each 10 pmol) were used per experiment as forward and reverse primers, and oligo 3 (2.5 pmol) was used per experiment as a nucleic acid amplification probe. As clamp nucleic acid, oligo 4-6 (BNA oligonucleotides) were each used at 10 pmol per experiment.

(4) Operation and Results of Nucleic Acid Amplification

Figure 2:
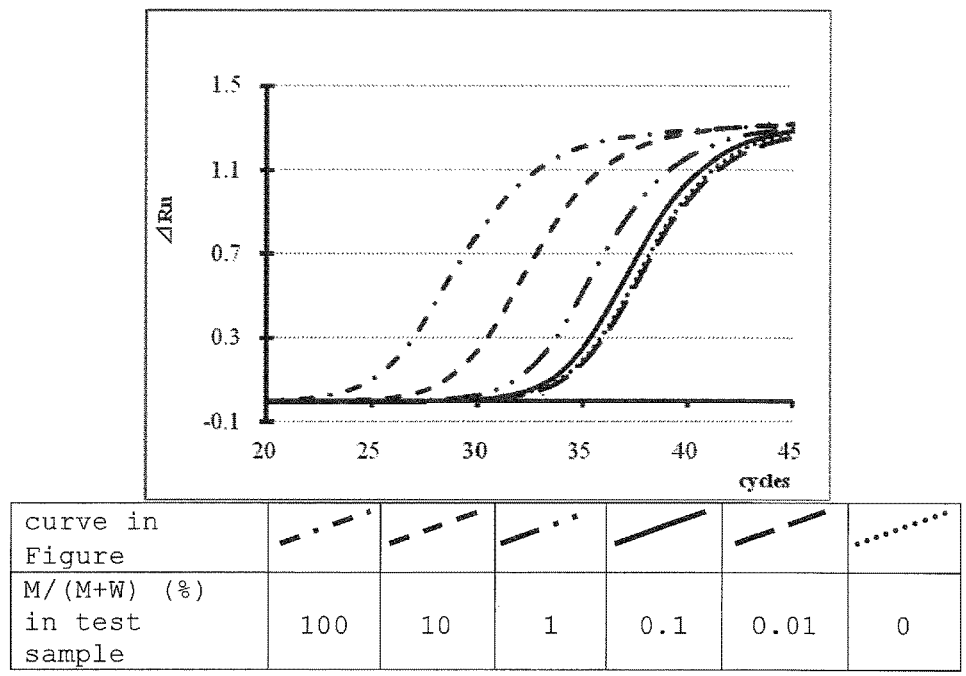
FIG. 2 shows a nucleic acid amplification curve by all nucleic acids amplification continuation probe (hereinafter to be referred to as "a nucleic acid amplification probe") (oligo 3) for real-time PCR of each test sample (mixed sample of mutated/(mutated+wild-type) (100%-0%) genes) by a BNA clamp method using oligo 4 and targeting KRAS gene G12V mutation, which is obtained in Example 1.
Figure 3:
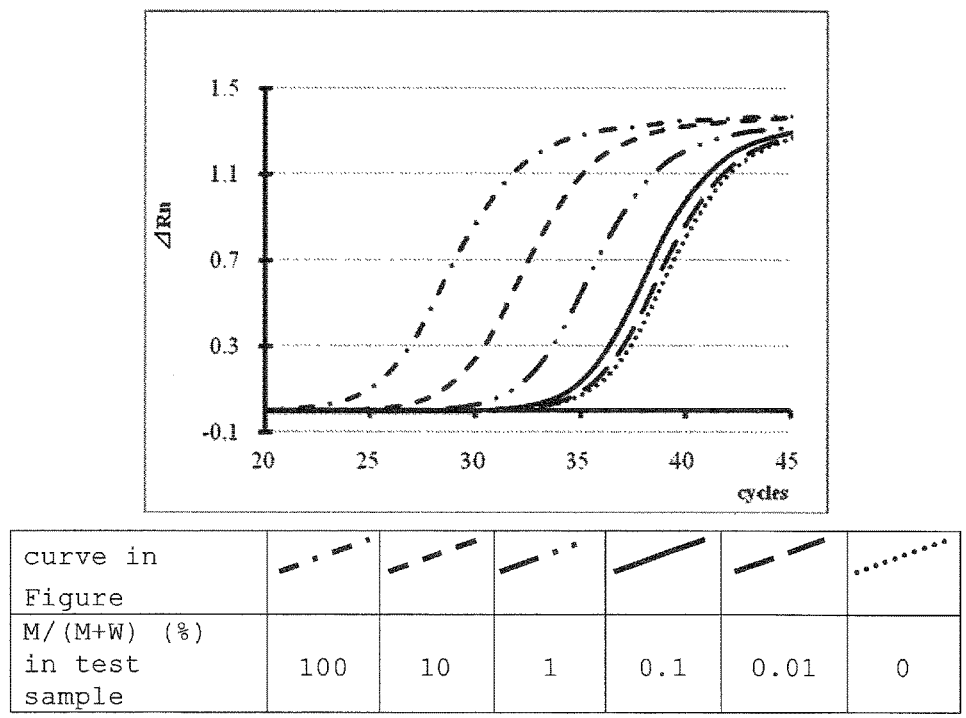
FIG. 3 shows a nucleic acid amplification curve by a nucleic acid amplification probe (oligo 3) for real-time PCR of each test sample (mixed sample of mutated/(mutated+ wild-type) (100%-0%) genes) by a BNA clamp method using oligo 5 and targeting KRAS gene G12V mutation, which is obtained in Example 1.
Figure 4:
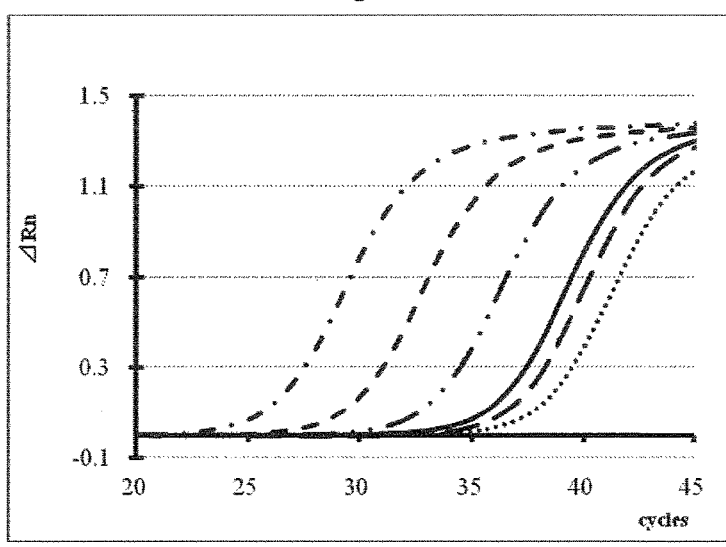
FIG. 4 shows a nucleic acid amplification curve by a nucleic acid amplification probe (oligo 3) for real-time PCR of each test sample (mixed sample of mutated/(mutated+ wild-type) (100%-0%) genes) by a BNA clamp method using oligo 6 and targeting KRAS gene G12V mutation, which is obtained in Example 1.

A mixture of the above-mentioned (1)-(3) of the test samples, reagent for nucleic acid amplification, primer, nucleic acid amplification probe, and clamp nucleic acid was subjected to (i) 50° C. for 2 min, (ii) 95° C. for 20 sec, (iii) 95° C. for 10 sec, (iv) 57° C. for 60 sec, after which (v) operations of (iii)-(iv) were repeated 55 times in a nucleic acid amplification apparatus. Nucleic acid amplification curves monitoring the nucleic acid amplification processes (up to 45 cycles) using a nucleic acid amplification probe, each test sample and each clamp nucleic acid are shown in FIGS. 2-4, and the Ct value data are shown in Table 2. In the Table, M is a mutation-type, and W is a wild-type. The Ct value means the number of cycles when a PCR amplification product has reached a given level, and the ΔCt value means a difference in Ct values between 0% mutated sample and each test sample.

TABLE 2

Ct value data in real-time PCR utilizing each BNA oligonucleotide (oligo 4-6) for clamp nucleic acid in Example 1

| M/(M + W) | 100% | 10% | 1% | 0.1% | 0.01% | 0% |
|---|---|---|---|---|---|---|
| Oligo 4 | | | | | | |
| Ct value | 23.44 | 26.89 | 30.23 | 32.94 | 33.93 | 34.13 |
| ΔCt (0% − X %) | 10.69 | 7.24 | 3.90 | 1.19 | 0.20 | |
| Oligo 5 | | | | | | |
| Ct value | 23.58 | 26.93 | 30.09 | 33.23 | 34.67 | 34.87 |
| ΔCt (0% − X %) | 11.29 | 7.94 | 4.78 | 1.64 | 0.20 | |
| Oligo 6 | | | | | | |
| Ct value | 24.51 | 27.96 | 31.61 | 34.66 | 36.09 | 36.23 |
| ΔCt (0% − X %) | 11.72 | 8.27 | 4.62 | 1.57 | 0.15 | |

In any of 10-18 mer BNA oligonucleotides (oligo 4-6), a large difference was found in the nucleic acid amplification curve and Ct value between 1% and 0% of the ratio of the mutated gene in the test sample (M/(M+W)), and it was clarified that the both can be distinguished.

Figure 5:
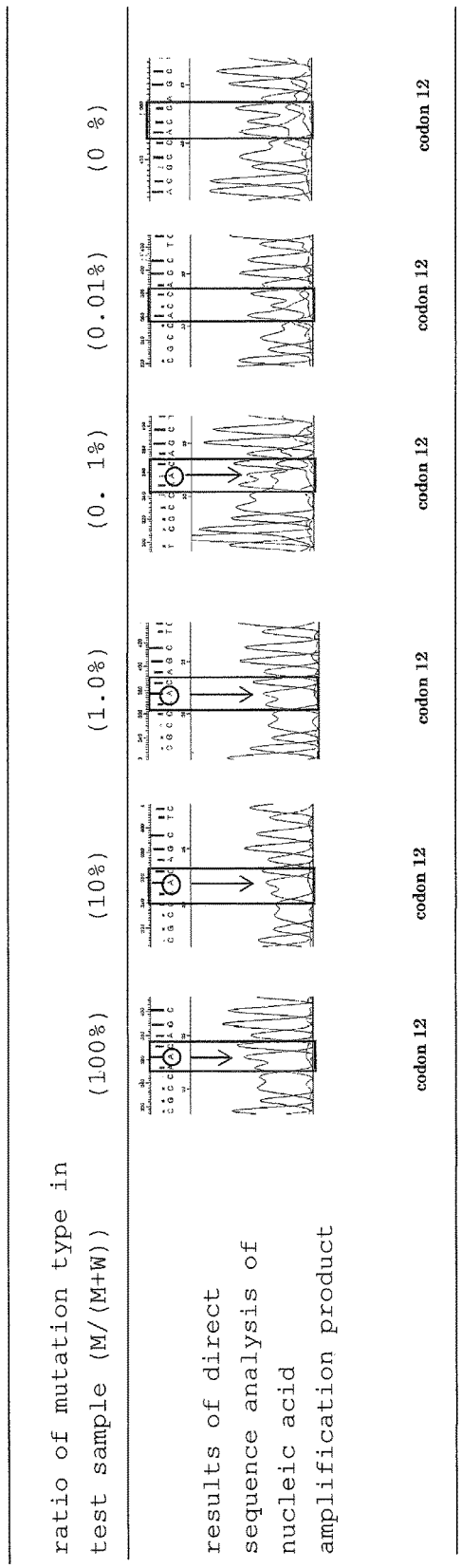
FIG. 5 shows a base sequence analysis chart near codon 12 of an amplification product after 55 cycles of nucleic acid amplification by real-time PCR of each test sample (mixed sample of mutated/(mutated+wild-type)(100%-0%) genes) by a BNA clamp method using oligo 6 and targeting KRAS gene G12V mutation, which is obtained in Example 1.
Figure 6:
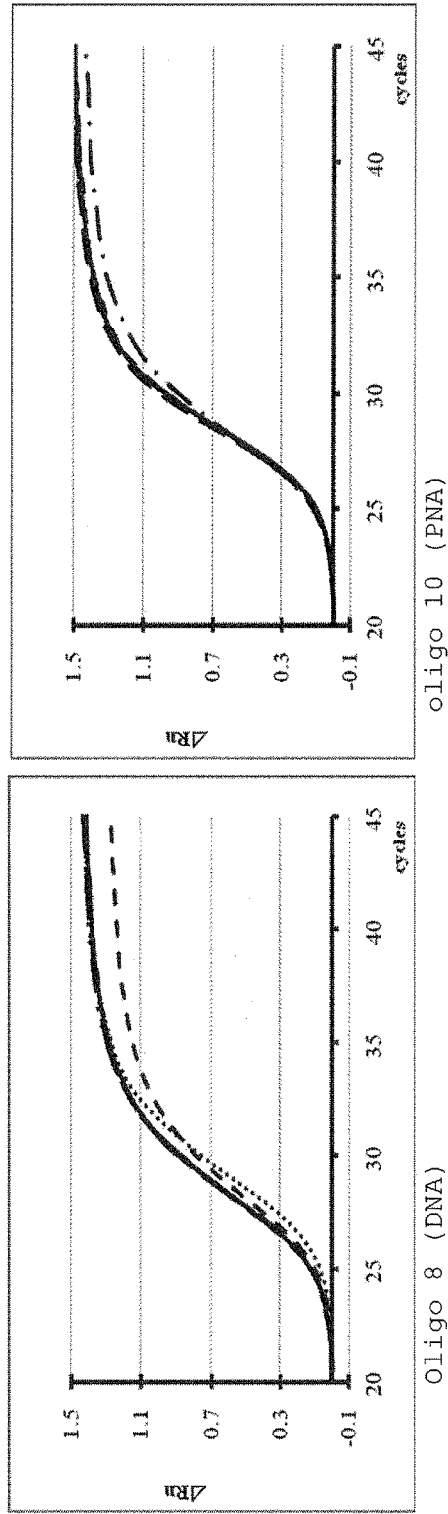
FIG. 6 shows a nucleic acid amplification curve by a nucleic acid amplification probe (oligo 3), which compares the clamp effect of oligo 5 (BNA) with that of oligo 8 (DNA), oligo 9 (LNA) and oligo 10 (PNA) by real-time PCR of each test sample (mixed sample of mutated/(mutated+wild-type)(100%-0%) genes) targeting KRAS gene G12V mutation, which is obtained in Example 2.
Figure 6:
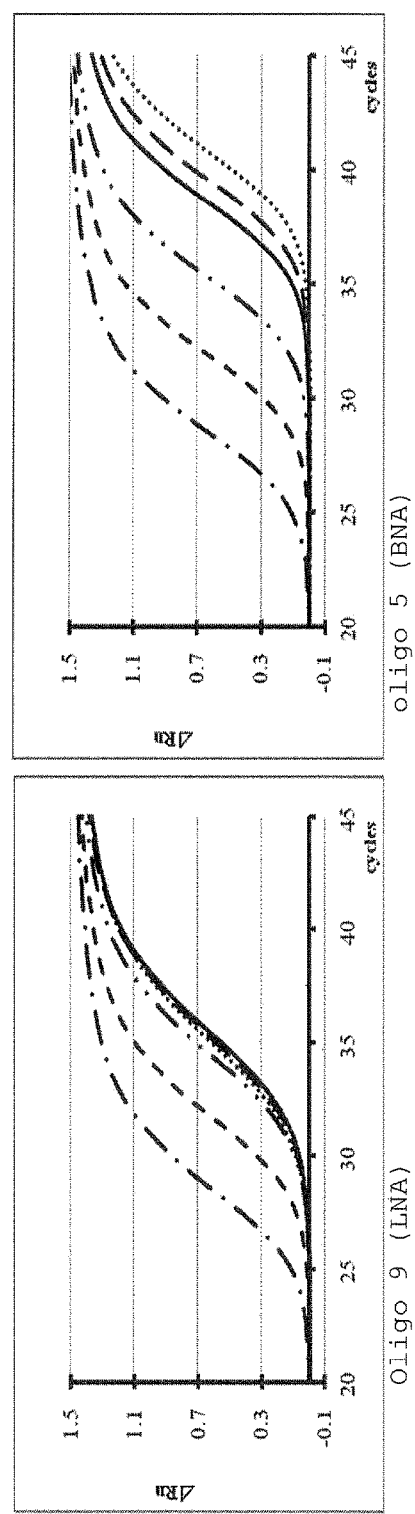
Figure 7:
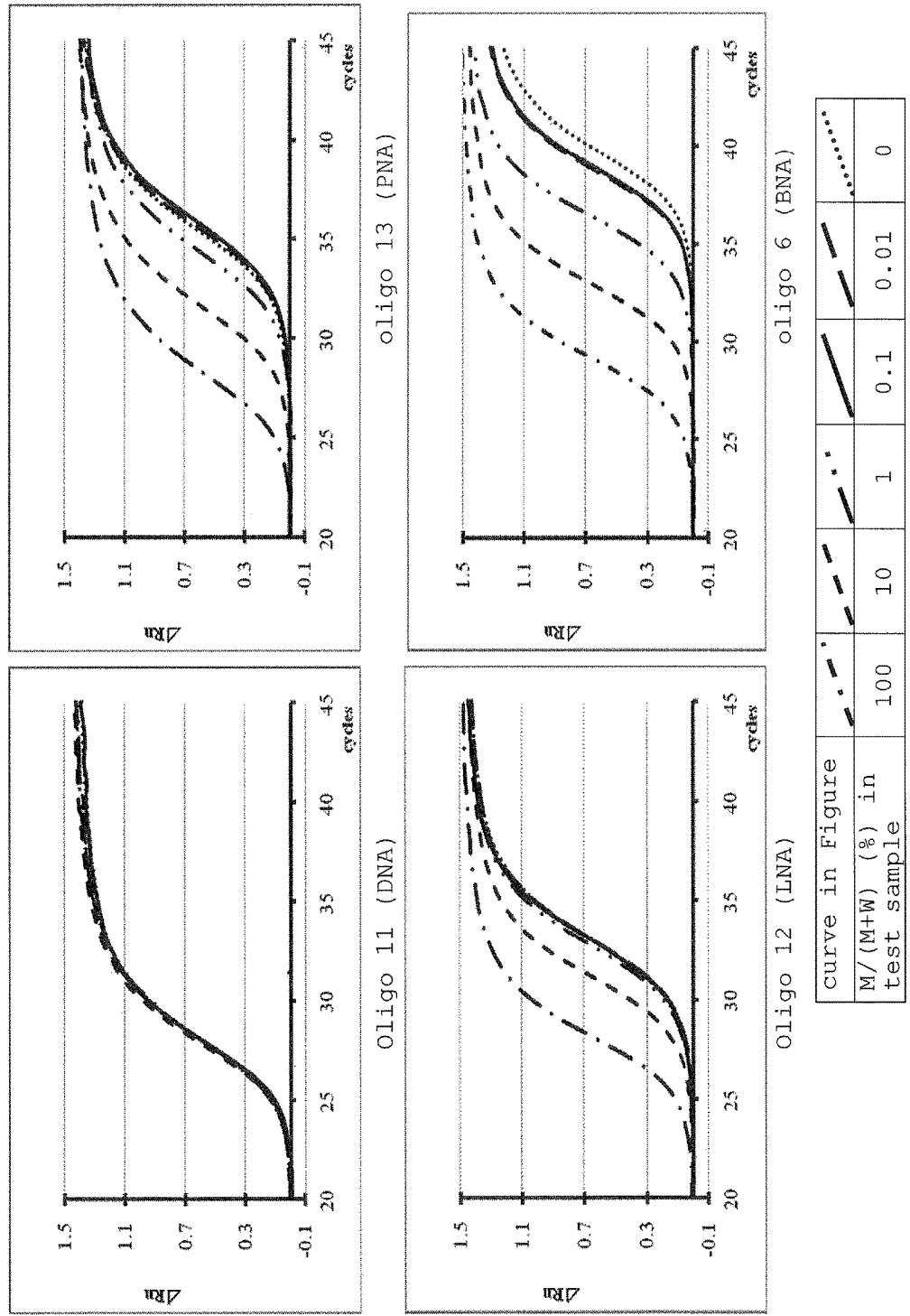
FIG. 7 shows a nucleic acid amplification curve by a nucleic acid amplification probe (oligo 3), which compares the clamp effect of oligo 6 (BNA) with that of oligo 11 (DNA), oligo 12 (LNA) and oligo 13 (PNA) by real-time PCR of each test sample (mixed sample of mutated/(mutated+wild-type) (100%-0%) genes) targeting KRAS gene G12V mutation, which is obtained in Example 2.

(5) Results of Direct Sequence Analysis After Nucleic Acid Amplification Operation A base sequence analysis chart of the vicinity of codon12, which was obtained by direct sequence analysis of an amplification product after 55 cycles of nucleic acid amplification of each test sample (100%-0% gene mixed sample of (M/(M+W)) by real-time PCR by the above-mentioned BNA clamp to method using oligo 6 is shown in FIG. 5. From the Figure, the presence of a mutated gene can be confirmed even in a test sample with M/(M+W)=0.1%, according to direct sequence analysis of the nucleic acid amplification by the BNA clamp method. That is, it has been clarified that the detection sensitivity of mutation-type is not more than 0.1%.

[Example 2] Detection Experiment 2 of KRAS Gene G12V Mutation in Model Test Sample (Comparison of Clamp Effect of BNA and DNA, LNA, and PNA)

(1) Test Sample

Commercially available human genomic DNA was used as a wild-type gene sample of KRAS gene and a DNA extracted from SW480-cultured cells was used as a G12V mutated gene sample. The amount of each DNA was determined from the UV spectrum of each sample and Ct value obtained by real-time PCR using oligo 1, 2 and 3 as forward primer, reverse primer and nucleic acid amplification probe. Based on the DNA amount thereof, model test samples having a mutation type of 100%, 10%, 1.0%, 0.1%, 0.01% or 0% were produced, and the respective model test samples were used in an amount of 50 ng per each experiment.

(2) Nucleic Acid Amplification Apparatus and Reagent for Nucleic Acid Amplification StepOnePlus (manufactured by ABI) was used as a real-time PCR apparatus and TaqMan™ Fast Advanced Master Mix (manufactured by ABI) was used as the reagents for nucleic acid amplification. The amount of the reagent to be used was in accordance with the attached manual.

(3) Primer, Nucleic Acid Amplification Probe, and Clamp Nucleic Acid

Oligo 1 and oligo 2 (each 10 pmol) were used per experiment as forward and reverse primers, and oligo 3 (2.5 pmol) was used per experiment as a nucleic acid amplification probe. For comparison evaluation of the clamp effect, oligo 5, 6 (BNA), oligo 8, 11 (DNA), oligo 9, 12 (LNA) and oligo 10, 13 (PNA) were each used at 10 pmol per experiment.

(4) Operation and Results of Nucleic Acid Amplification

Figure 8:
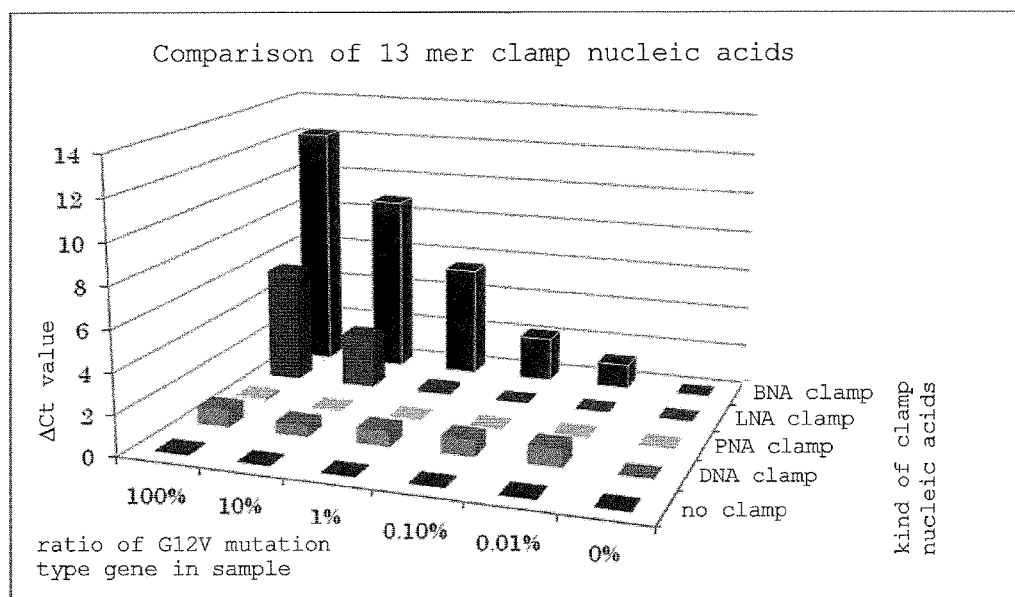
FIG. 8 shows a graph of ΔCt value calculated from a nucleic acid amplification curve by a nucleic acid amplification probe (oligo 3), which compares the clamp effect of oligo 5 (BNA) with that of oligo 8 (DNA), oligo 9 (LNA) and oligo 10 (PNA) by real-time PCR of each test sample (mixed sample of mutated/(mutated+wild-type) (100%-0%) genes) targeting KRAS gene G12V mutation, which is obtained in Example 2.
Figure 9:
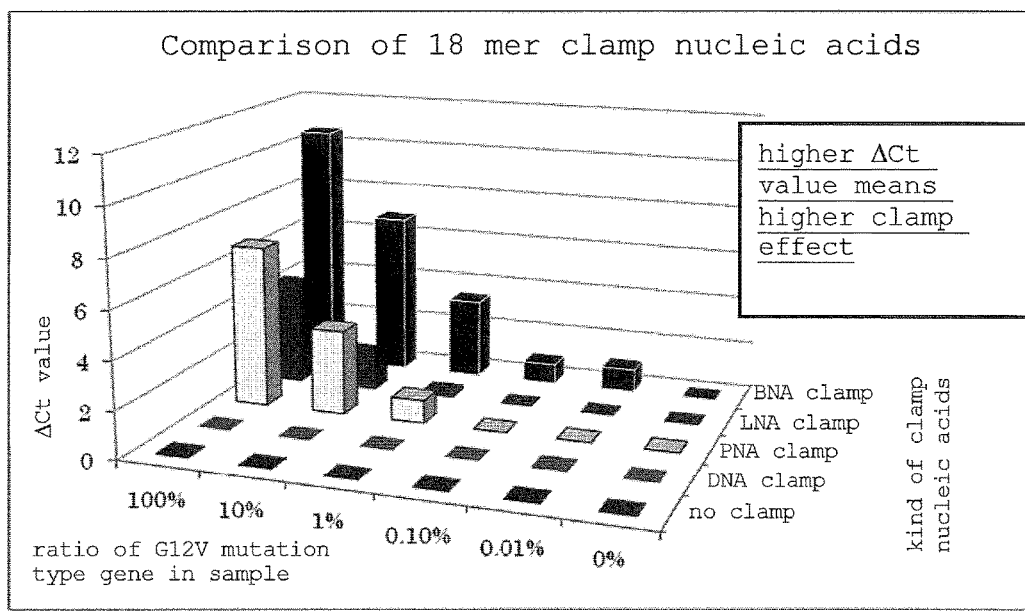
FIG. 9 shows a graph of ΔCt value calculated from a nucleic acid amplification curve by a nucleic acid amplification probe (oligo 3), which compares the clamp effect of oligo 6 (BNA) with that of oligo 11 (DNA), oligo 12 (LNA) and oligo 13 (PNA) by real-time PCR of each test sample (mixed sample of mutated/(mutated+wild-type)(100%-0%) genes) targeting KRAS gene G12V mutation, which is obtained in Example 2.

A mixture of the above-mentioned (1)-(3) of the test samples, reagent for nucleic acid amplification, primer, nucleic acid amplification probe, and clamp nucleic acid was subjected to (i) 50° C. for 2 min, (ii) 95° C. for 20 sec, (iii) 95° C. for 10 sec, (iv) 57° C. for 60 sec, after which (v) operations of (iii)-(iv) were repeated 55 times in a nucleic acid amplification apparatus. Gene amplification curves monitoring the nucleic acid amplification processes (up to 45 cycles) using a nucleic acid amplification probe, each test sample and each clamp nucleic acid are shown in Tables 6 and 7, Ct value data are shown in Tables 3-4, and the comparison figures of the respective Ct values are shown in FIGS. 8 and 9.

TABLE 3

Ct value data in real-time PCR utilizing each 13 mer clamp nucleic acid (oligo 5, 8, 9, 10) in Example 2

| M/(M + W) | 100% | 10% | 1% | 0.1% | 0.01% | 0% |
|---|---|---|---|---|---|---|
| Oligo 5 (BNA) | | | | | | |
| Ct value | 24.25 | 27.65 | 31.00 | 34.30 | 35.28 | 36.48 |
| ΔCt (0% − X %) | 12.23 | 8.83 | 5.48 | 2.18 | 1.20 | |
| Oligo 8 (DNA) | | | | | | |
| Ct value | 24.55 | 24.85 | 24.66 | 24.58 | 24.51 | 25.43 |
| ΔCt (0% − X %) | 0.88 | 0.58 | 0.77 | 0.85 | 0.92 | |

TABLE 3-continued

Ct value data in real-time PCR utilizing each 13 mer clamp nucleic acid (oligo 5, 8, 9, 10) in Example 2

| M/(M + W) | 100% | 10% | 1% | 0.1% | 0.01% | 0% |
|---|---|---|---|---|---|---|
| Oligo 9 (LNA) | | | | | | |
| Ct value | 24.24 | 27.25 | 29.71 | 30.40 | 30.20 | 29.90 |
| ΔCt (0% − X %) | 5.66 | 2.65 | 0.19 | −0.50 | −0.30 | |
| Oligo 10 (PNA) | | | | | | |
| Ct value | 24.56 | 24.78 | 24.77 | 24.78 | 24.64 | 24.72 |
| ΔCt (0% − X %) | 0.16 | −0.06 | −0.05 | −0.06 | 0.08 | |

TABLE 4

Ct value data in real-time PCR utilizing each 18 mer clamp nucleic acid (oligo 6, 11, 12, 13) in Example 2

| M/(M + W) | 100% | 10% | 1% | 0.1% | 0.01% | 0% |
|---|---|---|---|---|---|---|
| Oligo 6 (BNA) | | | | | | |
| Ct value | 25.55 | 29.28 | 32.76 | 35.28 | 35.16 | 36.12 |
| ΔCt (0% − X %) | 10.57 | 6.84 | 3.36 | 0.84 | 0.94 | |
| Oligo 11 (DNA) | | | | | | |
| Ct value | 24.45 | 24.54 | 24.54 | 24.62 | 24.39 | 24.44 |
| ΔCt (0% − X %) | −0.01 | −0.10 | −0.10 | −0.18 | 0.05 | |
| Oligo 12 (LNA) | | | | | | |
| Ct value | 24.59 | 27.39 | 28.78 | 29.03 | 29.11 | 28.92 |
| ΔCt (0% − X %) | 4.33 | 1.53 | 0.14 | −0.12 | −0.19 | |
| Oligo 13 (PNA) | | | | | | |
| Ct value | 24.74 | 28.00 | 30.59 | 31.88 | 31.69 | 31.55 |
| ΔCt (0% − X %) | 6.81 | 3.55 | 0.96 | −0.33 | −0.14 | |

From these results, it was demonstrated that BNA oligonucleotide is superior to other oligonucleotides in clamp effect.

[Example 3] Detection Experiment 3 of KRAS Gene G12V Mutation in Model Test Sample (Detection Effect of BNA Clamp Nucleic Acid+Mutation Detection Probe)

(1) Test Sample

Commercially available human genomic DNA was used as a wild-type gene sample of KRAS gene and a DNA extracted from SW480-cultured cells was used as a G12V mutated gene sample. The amount of each DNA was determined from the UV spectrum of each sample and Ct value obtained by real-time PCR using oligo 1, 2 and 3 as forward primer, reverse primer and nucleic acid amplification probe. Based on the DNA amount thereof, model test samples having a mutation type of 100%, 10%, 1.0%, 0.1%, 0.01% or 0% were produced. The respective model test samples were used in an amount of 50 ng per each experiment.

(2) Nucleic Acid Amplification Apparatus and Reagent for Nucleic Acid Amplification StepOnePlus (manufactured by ABI) was used as a real-time PCR apparatus and TaqMan™ Fast Advanced Master Mix (manufactured by ABI) was used as the reagents for nucleic acid amplification. The amount of the reagent to be used was in accordance with the attached manual.

(3) Primer, Nucleic Acid Amplification Probe, Clamp Nucleic Acid, and Mutation Detection Probe Oligo 1 and oligo 2 (each 10 pmol) were used per experiment as forward and reverse primers, and oligo 3-2 (2.5 pmol) was used per experiment as a nucleic acid amplification probe. Oligo 6 (BNA) (10-1 pmol) was used per experiment as a clamp nucleic acid, and oligo 14, oligo 14-2, oligo 15 and oligo 15-2 (5 pmol) were used per experiment as mutation detection probe.

(4) Operation and Results of Nucleic Acid Amplification

Figure 10:
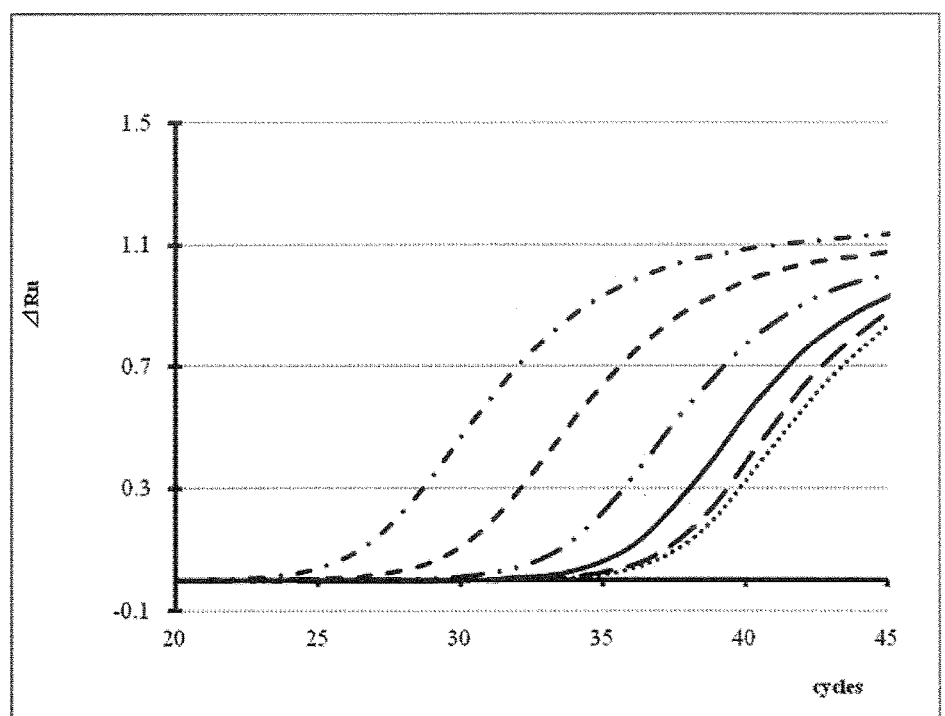
FIG. 10 shows a nucleic acid amplification curve and Ct value by a nucleic acid amplification probe (oligo 3-2) for real-time PCR of each test sample (mixed sample of mutated/(mutated+wild-type)(100% 0%) genes) by a BNA clamp method using oligo 6 and targeting KRAS gene G12V mutation, which is obtained in Example 3.
Figure 11:
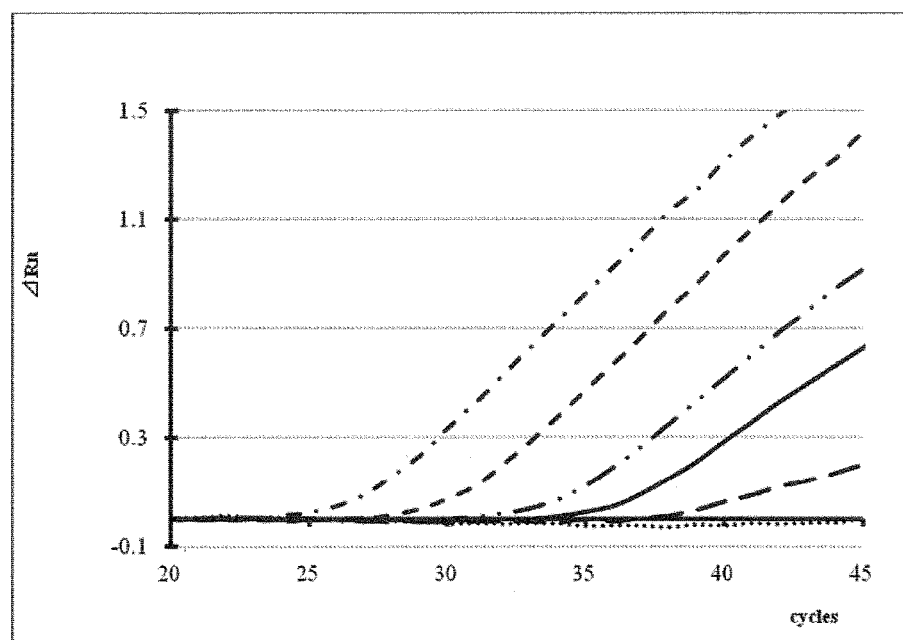
FIG. 11 shows a nucleic acid amplification curve and Ct value by a probe for detecting mutation of oligo 15 for real-time PCR of each test sample (mixed sample of mutated/(mutated+wild-type)(100%-0%) genes) by a DNA clamp method using oligo 6 and targeting KRAS gene G12V mutation, which is obtained in Example 3.

A mixture of the above-mentioned (1)-(3) of the test samples, reagent for nucleic acid amplification, primer, nucleic acid amplification probe, clamp nucleic acid and probe for mutation detection was subjected to (i) 50° C. for 2 min, (ii) 95° C. for 20 sec, (iii) 95° C. for 10 sec, (iv) 57° C. for 60 sec, after which (v) operations of (iii)-(iv) were repeated 55 times in a nucleic acid amplification apparatus. Nucleic acid amplification curves monitoring the nucleic acid amplification processes (up to 45 cycles) using 10 pmol of clamp nucleic acid (oligo 6), and a nucleic acid amplification probe and a probe for mutation detection (oligo 15) in each test sample, and the Ct value are shown in FIG. 10 and FIG. 11.

Figure 12:
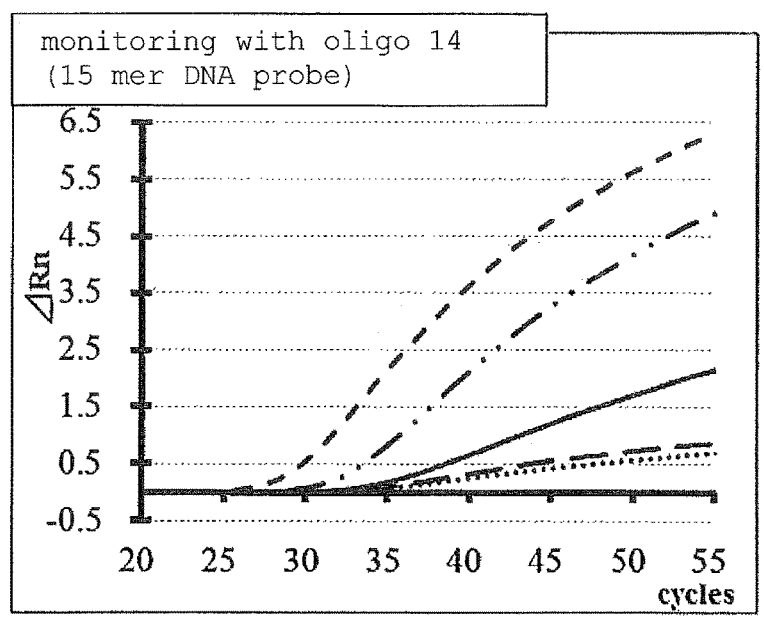
FIG. 12 shows a nucleic acid amplification curve and Ct value by 15 mer mutated detection DNA and BNA probes when 1 pmol of clamp nucleic acid (oligo 6) was used targeting KRAS gene G12V mutation, which is obtained in Example 3. a) monitoring of oligo 14, b) monitoring of oligo 15.
Figure 12:
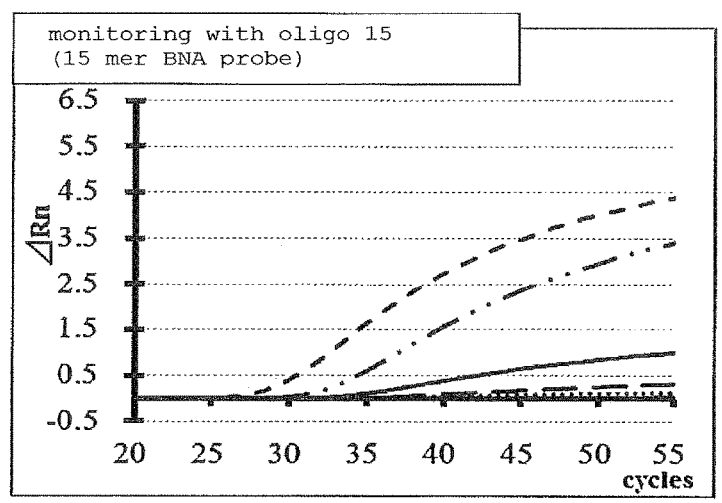
Figure 13:
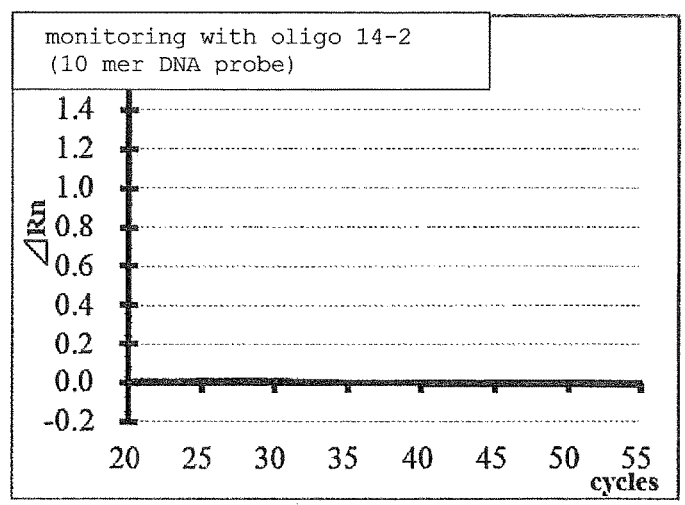
FIG. 13 shows a nucleic acid amplification curve and Ct value by 10 mer mutated detection DNA and BNA probes when 1 pmol of clamp nucleic acid (oligo 6) was used targeting KRAS gene G12V mutation, which is obtained in Example 3. a) monitoring of oligo 14-2, b) monitoring of oligo 15-2.
Figure 13:
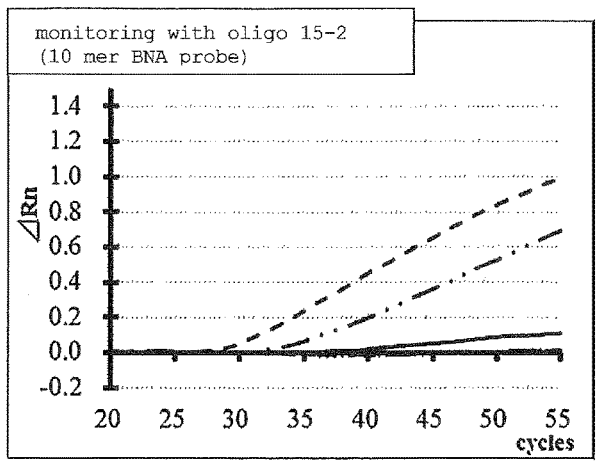
Figure 14:
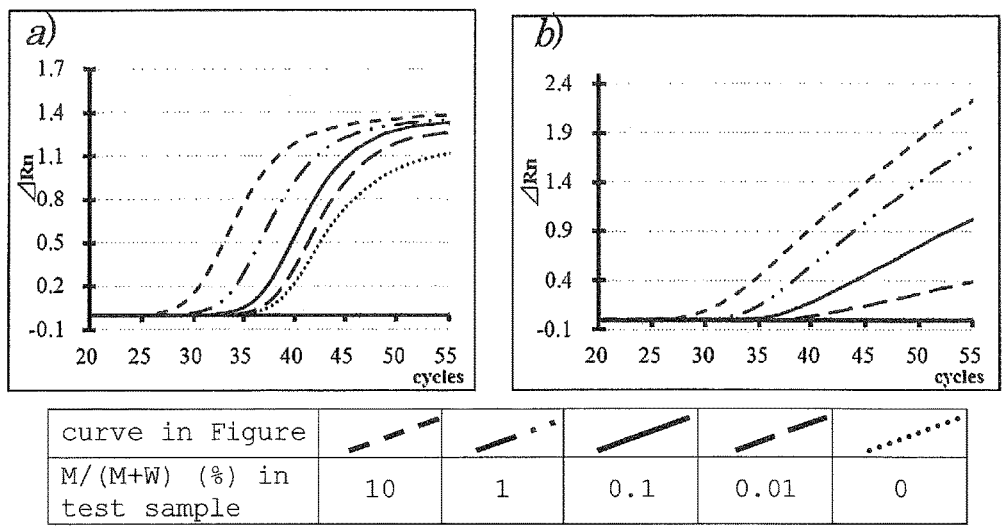
FIG. 14 shows a nucleic acid amplification curve by each probe (a: oligo 3-2 and b: oligo 14) for real-time PCR of each test sample (mixed sample of mutated/(mutated+wild-type)(10%-0%) genes) by a DNA clamp method using oligo 6 and targeting KRAS gene G12V mutation, which is obtained in Example 4.
Figure 15:
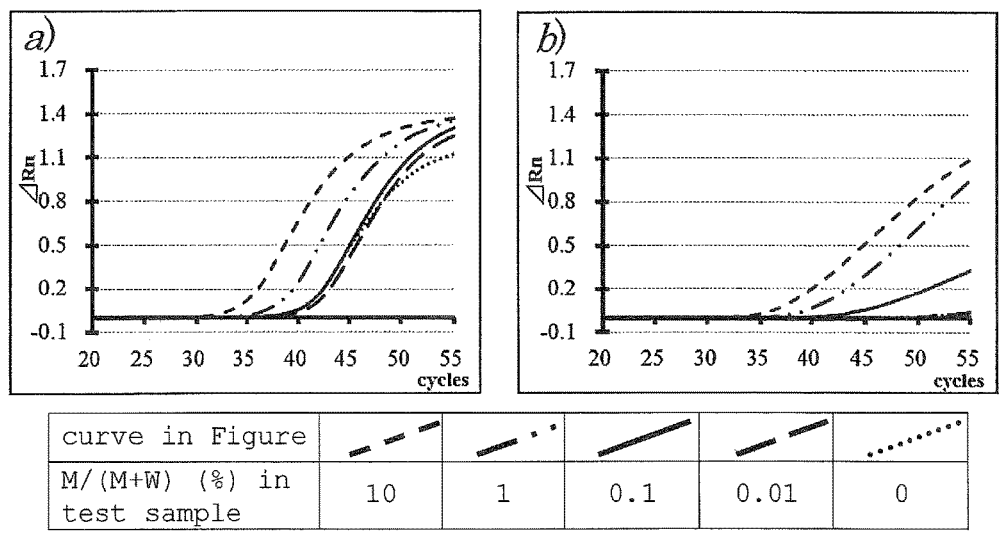
FIG. 15 shows a nucleic acid amplification curve by each probe (a: oligo 3-2 and b: oligo 16) for real-time PCR of each test sample (mixed sample of mutated/(mutated+wild-type)(10%-0%) genes) by a BNA clamp method using oligo 6 and targeting KRAS gene G12D mutation, which is obtained in Example 4.
Figure 16:
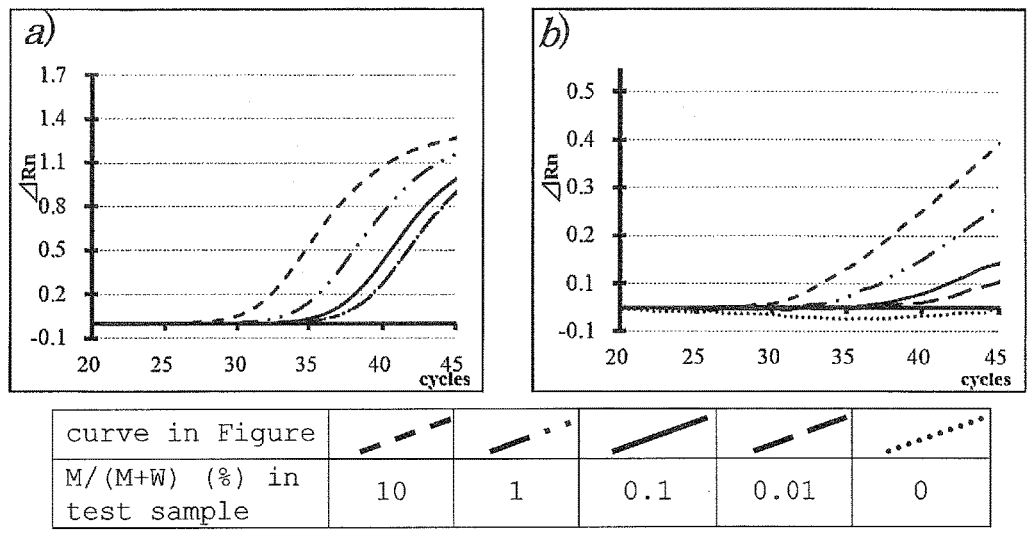
FIG. 16 shows a nucleic acid amplification curve by each probe (a: oligo 3-2 and b: oligo 17) for real-time PCR of each test sample (mixed sample of mutated/(mutated+wild-type)(10%-0%) genes) by a BNA clamp method using oligo 6 and targeting KRAS gene C13D mutation, which is obtained in Example 4.
Figure 17:
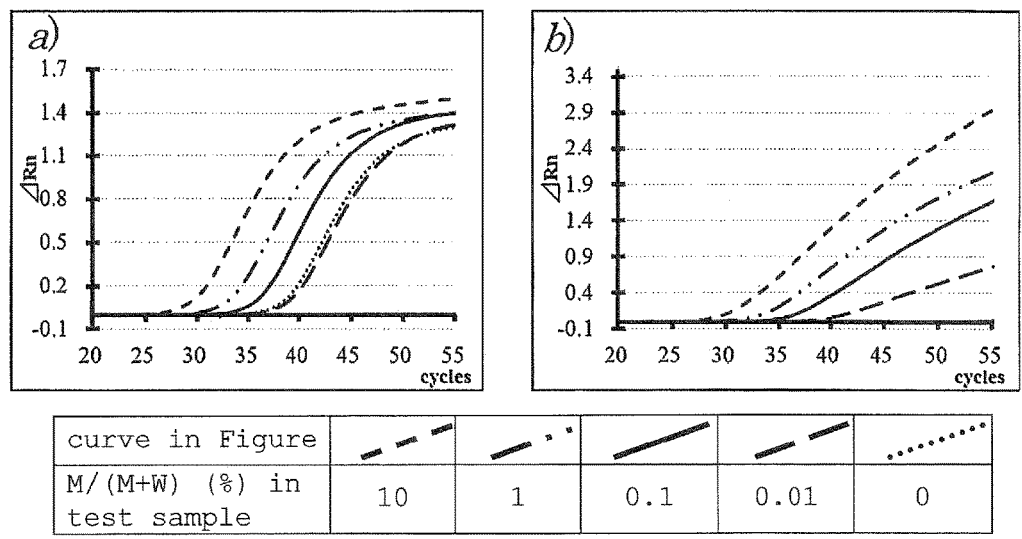
FIG. 17 shows a nucleic acid amplification curve by each probe (a: oligo 3-2 and b: oligo 18) for real-time PCR of each test sample (mixed sample of mutated/(mutated+wild-type)(10%-0% genes) by a BNA clamp method using oligo 6 and targeting KRAS gene G12A mutation, which is obtained in Example 4.
Figure 18:
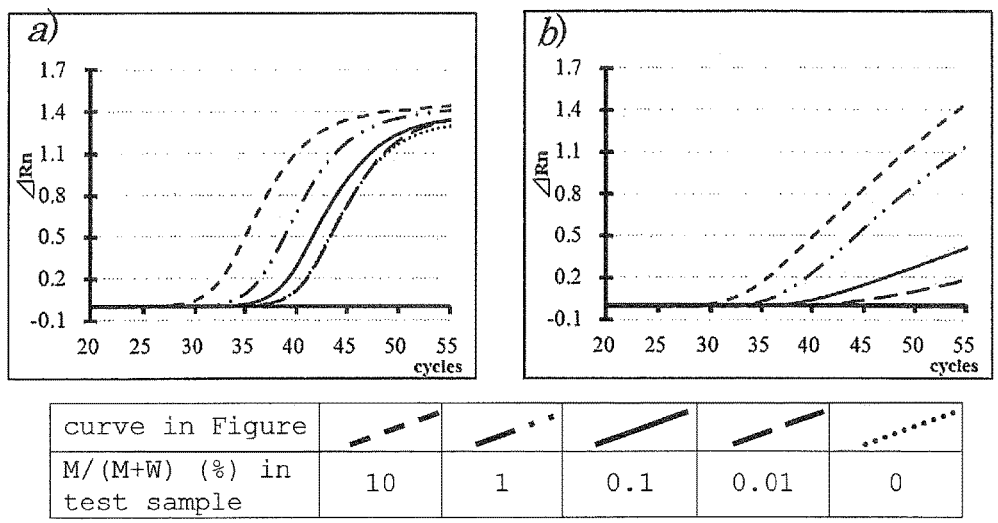
FIG. 18 shows a nucleic acid amplification curve by each probe (a: oligo 3-2 and b: oligo 19) for real-time PCR of each test sample (mixed sample of mutated/(mutated+wild-type)(10%-0%) genes) by a BNA clamp method using oligo 6 and targeting KRAS gene G12C mutation, which is obtained in Example 4.
Figure 19:
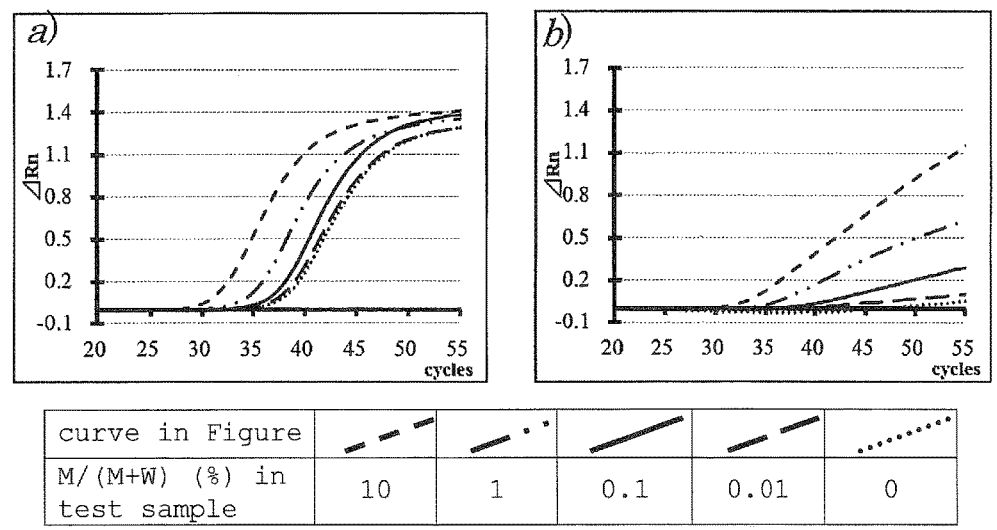
FIG. 19 shows a nucleic acid amplification curve by each probe (a: oligo 3-2 and b: oligo 20) for real-time PCR of each test sample (mixed sample of mutated/(mutated+wild-type)(10%-0%) genes) by a BNA clamp method using oligo 6 and targeting KRAS gene G12S mutation, which is obtained in Example 4.
Figure 20:
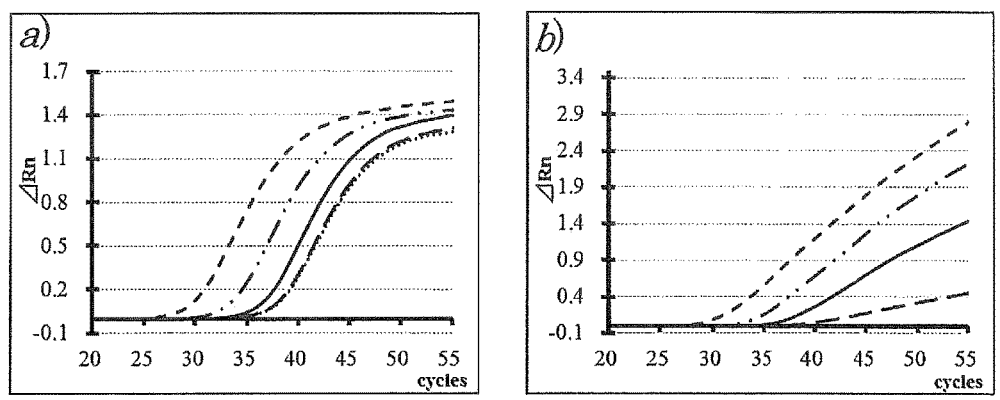
FIG. 20 shows a nucleic acid amplification curve by each probe (a: oligo 3-2 and b: oligo 21) for real-time PCR of each test sample (mixed sample of mutated/(mutated+wild-type)(10%-0%) genes) by a BNA clamp method using oligo 6 and targeting KRAS gene G12R mutation, which is obtained in Example 4.

In addition, nucleic acid amplification curves monitoring the nucleic acid amplification processes (up to 55 cycles) using 1 pmol of clamp nucleic acid (oligo 6), and the above-mentioned each four kinds of probes for mutation detection in each test sample, and the Ct value are shown in FIG. 12 and FIG. 13. As is clear from these Figures and Ct value data, it was demonstrated that the combined use of the BNA clamp technique and mutation detection probe can clearly detect the presence of a mutated type in a DNA test sample containing 0.01% KRAS gene G12V mutated wild-type gene, since the ΔCt value (0%-X %) becomes a high number even between test samples with a presence ratio of KRAS gene G12V mutated type M/(M+W) of 0.01% and 0%.

Also, from ΔCt value comparison from FIG. 12 and FIG. 13, it was clarified that BNA oligonucleotide also has superior function as a mutation detection probe. That is, ΔCt value of 15 mer, 10 mer BNA mutation detection probes at each sample concentration is greater than the ΔCt value of the corresponding DNA probe. Particularly, in the case of a single strand (10 mer) probe, the difference in the ΔCt value is markedly large.

[Example 4] Experiment for Detection of 7 Major Mutations (G12V, G12D, G13D, G12C, G12A, G12S, G12R) of KRAS Gene in Model Test Sample (BNA Clamp Method+Mutation Detection Probe)

(1) Test Sample

As wild-type and each mutation type gene samples of KRAS gene, commercially available human genomic DNAs corresponding thereto were used. The amount of each DNA was determined from the UV spectrum of each sample and Ct value obtained by real-time PCR using oligo 1, 2 and 3 as forward primer, reverse primer and nucleic acid amplification probe. Based on the DNA amount thereof, model test samples having each mutation type of 10%, 1.0%, 0.1%, 0.01% or 0% were produced, and the respective model test samples were used in an amount of 50 ng per each experiment.

(2) Nucleic Acid Amplification Apparatus and Reagent for Nucleic Acid Amplification StepOnePlus (manufactured by ABI) was used as a real-time PCR apparatus and TagMan™ Fast Advanced Master Mix (manufactured by ABI) was used as the reagents for nucleic acid amplification. The amount of the reagent to be used was in accordance with the attached manual.

(3) Primer, Nucleic Acid Amplification Probe, and Clamp Nucleic Acid

Oligo 1 and oligo 2 (each 10 pmol) were used per experiment as forward and reverse primers, and oligo 3-2 (2.5 pmol) was used per experiment as a nucleic acid amplification probe. As clamp nucleic acid, oligo 6 (BNA oligonucleotides) was used at 10 pmol per experiment.

In addition, as a probe for selectively recognizing and detecting each mutation-type, mutation detection probes corresponding to respective mutation-types (oligo 14 [for G12V], oligo 16 [for G12D], oligo 17 [for G13D], oligo18 [for G12A], oligo 19 [for G12C], oligo 20 [for G12S] and oligo 21 [for G12R]) were used at 5 pmol per experiment.

(4) Operation and Results of Nucleic Acid Amplification

A mixture of the above-mentioned (1)-(3) of the test samples, reagent for nucleic acid amplification, primer, each probe, and clamp nucleic acid was subjected to (i) 50° C. for 2 min, (ii) 95° C. for 20 sec, (iii) 95° C. for 10 sec, (iv) 57° C. (54° C. when the target was G12D) for 60 sec, after which (v) operations of (iii)-(iv) were repeated 55 times in a nucleic acid amplification apparatus.

Nucleic acid amplification curves monitoring the nucleic acid amplification, using a nucleic acid amplification probe and each mutation detection probe, in the nucleic acid amplification processes (up to 45-55 cycles) of each mutation test sample of KRAS gene are shown in FIGS. 14-20, and the Ct value data is shown in Table 5 and Table 6. These data have clarified that, in any of the 7 major mutations of KRAS gene, this BNA clamp method is a technique capable of detecting the presence or absence of each mutation with high sensitivity (to nearly about 0.1%) in the evaluation using only a nucleic acid amplification probe for monitoring all nucleic acid amplification, and capable of detecting the presence or absence of each mutation and mutation mode with higher sensitivity (<0.1%) in the evaluation using each probe for mutation detection.

TABLE 5

Nucleic acid amplification probe targeting 7 mutations of KRAS gene in Example 4
Ct value data of (oligo 3-2)

| | M/(M + W) (%) | | | | |
|---|---|---|---|---|---|
| | 10% | 1% | 0.1% | 0.01% | 0% |
| target: G12V, clamp oligo: oligo 6, amplification monitor: oligo 3-2 | | | | | |
| Ct value | 28.72 | 32.31 | 35.51 | 37.09 | 37.97 |
| ΔCt value (0%-X %) | 9.25 | 5.66 | 2.46 | 0.88 | |
| target: G12D, clamp oligo: oligo 6, amplification monitor: oligo 3-2 | | | | | |
| Ct value | 34.11 | 37.58 | 40.57 | 41.21 | 40.52 |
| ΔCt value (0%-X %) | 6.41 | 2.94 | −0.05 | −0.69 | |
| target: G13D, clamp oligo: oligo 6, amplification monitor: oligo 3-2 | | | | | |
| Ct value | 30.15 | 33.42 | 35.93 | 37.10 | 37.07 |
| ΔCt value (0%-X %) | 6.92 | 3.65 | 1.14 | −0.03 | |
| target: G12A, clamp oligo: oligo 6, amplification monitor: oligo 3-2 | | | | | |
| Ct value | 28.76 | 32.15 | 34.95 | 38.17 | 37.71 |
| ΔCt value (0%-X %) | 8.95 | 5.56 | 2.77 | −0.46 | |
| target: G12C, clamp oligo: oligo 6, amplification monitor: oligo 3-2 | | | | | |
| Ct value | 30.23 | 34.04 | 36.75 | 38.67 | 38.55 |
| ΔCt value (0%-X %) | 8.32 | 4.51 | 1.80 | −0.12 | |

TABLE 5-continued

Nucleic acid amplification probe targeting 7 mutations of KRAS gene in Example 4
Ct value data of (oligo 3-2)

| | M/(M + W) (%) | | | | |
|---|---|---|---|---|---|
| | 10% | 1% | 0.1% | 0.01% | 0% |
| target: G12S, clamp oligo: oligo 6, amplification, monitor: oligo 3-2 | | | | | |
| Ct value | 30.19 | 33.53 | 35.76 | 36.61 | 37.04 |
| ΔCt value (0%-X %) | 6.85 | 3.51 | 1.28 | 0.43 | |
| target: G12R, clamp oligo: oligo 6, amplification monitor: oligo 3-2 | | | | | |
| Ct value | 28.78 | 32.44 | 35.52 | 36.98 | 37.11 |
| ΔCt value (0%-X %) | 8.32 | 4.66 | 1.58 | 0.13 | |

TABLE 6

Nucleic acid amplification probe targeting 7 mutations of KRAS gene in Example 4
Ct value data

| | M/(M + W) (%) | | | | |
|---|---|---|---|---|---|
| | 10% | 1% | 0.1% | 0.01% | 0% |
| target: G12V, clamp oligo: oligo 6, amplification monitor: oligo 14 | | | | | |
| Ct value | 26.50 | 30.68 | 34.37 | 38.04 | >55 |
| ΔCt value (0%-X %) | >28.50 | >24.32 | >20.63 | >16.96 | |
| target: G12D, clamp oligo: oligo 6, amplification monitor: oligo 16 | | | | | |
| Ct value | 34.11 | 37.51 | 42.32 | >55 | >55 |
| ΔCt value (0%-X %) | >20.89 | >17.49 | >12.68 | — | |
| target: G13D, clamp oligo: oligo 6, amplification monitor: oligo 17 | | | | | |
| Ct value | 30.76 | 34.26 | 38.51 | 40.87 | >55 |
| ΔCt value (0%-X %) | >24.24 | >20.74 | >16.49 | >14.13 | |
| target: G12A, clamp oligoi oligo 6, amplification monitor: oligo 18 | | | | | |
| Ct value | 27.91 | 31.31 | 34.44 | 38.92 | >55 |
| ΔCt value (0%-X %) | >27.09 | >23.69 | >20.56 | >16.08 | |
| target: G12C, clamp oligo: oligo 6, amplification monitor: oligo 19 | | | | | |
| Ct value | 30.69 | 34.51 | 39.01 | 44.04 | >55 |
| ΔCt value (0%-X %) | >24.31 | >20.49 | >15.99 | >10.96 | |
| target: G12S, clamp oligo: oligo 6, amplification monitor: oligo 20 | | | | | |
| Ct value | 29.59 | 32.63 | 36.41 | 38.95 | >55 |
| ΔCt value (0%-X %) | >25.41 | >22.37 | >18.59 | >16.05 | |
| target: G12R, clamp oligo: oligo 6, amplification monitor: oligo 21 | | | | | |
| Ct value | 28.05 | 31.95 | 35.30 | 38.97 | >55 |
| ΔCt value (0%-X %) | >26.95 | >23.05 | >19.70 | >16.03 | |

[Example 5] Detection of KRAS Gene G12V Mutation by BNA Clamp Method Using DNA Derived from Tissue FFPE of Cancer Patients as Sample (1) Test Sample To Genomic DNA and KRAS gene G12V mutated genomic DNA extracted from commercially available FFPE clinical tissue sample (KRAS wild-type) were used. The amount of each DNA was determined from the UV spedtrum of each sample and Ct value obtained by real-time PCR using oligo 1, 2 and 3 as forward primer, reverse primer and nucleic acid amplification probe. Based on the DNA amount thereof, mixed test samples having G12V mutation type of 1.0%, 0.5%, 0.1%, 0.05% or 0% were produced, and the respective test samples were used in an amount of 20 ng per each experiment.

(2) Nucleic Acid Amplification Apparatus and Reagent for Nucleic Acid Amplification An apparatus and reagents similar to those in Example 4 were used.

(3) Primer, Nucleic Acid Amplification Probe, Clamp Nucleic Acid, and Mutation Detection Probe Oligo 1 and oligo 2 (each 20 pmol) were used per experiment as forward and reverse primers, and oligo 3-2 (5 pmol) was used per experiment as a nucleic acid amplification probe. As BNA clamp nucleic acid, oligo 4-2, oligo 5 and oligo 6 (BNA oligonucleotides) were each used at 20 pmol per experiment.

As a mutation detection probe to selectively detect G12V mutation type, oligo 14 was used at 10 pmol per experiment.

(4) Operation and Results of Nucleic Acid Amplification

Figure 21:
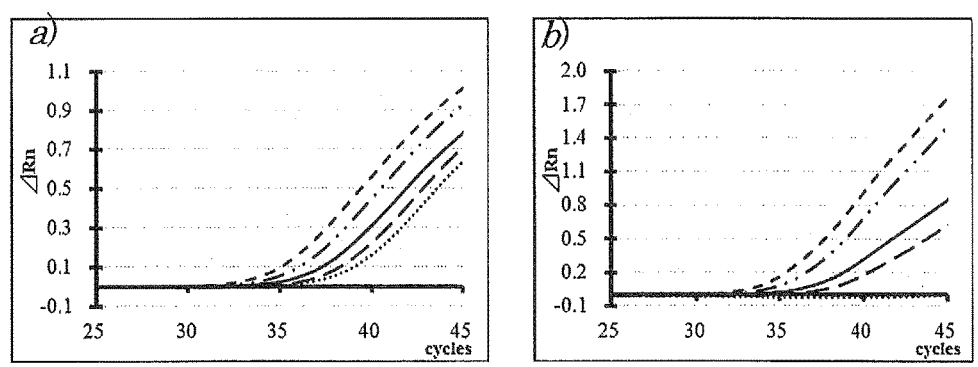
FIG. 21 shows a nucleic acid amplification curve by each probe (a: oligo 3-2 and b: oligo 14) for real-time PCR of each test sample (mixed sample of mutated/(mutated+wild-type)(1%-0%) genes) by a BNA clamp method using oligo 4-2 and targeting KRAS gene G12V mutation, which is obtained in Example 5.
Figure 22:
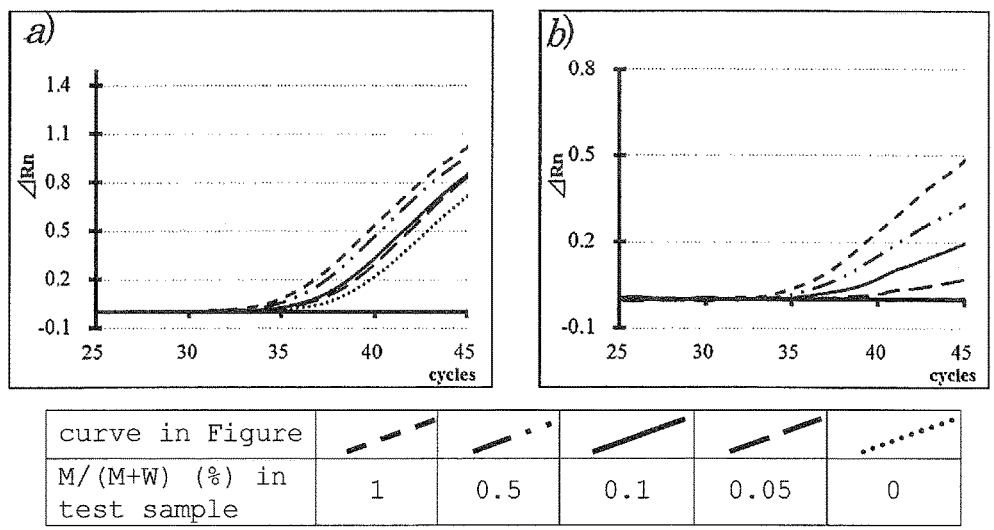
FIG. 22 shows a nucleic acid amplification curve by each probe (a: oligo 3-2 and b: oligo 14) for real-time PCR of each test sample (mixed sample of mutated/(mutated+wild-type)(1%-0%) genes) by a BNA clamp method using oligo 5 and targeting KRAS gene G12V mutation, which is obtained in Example 5.
Figure 23:
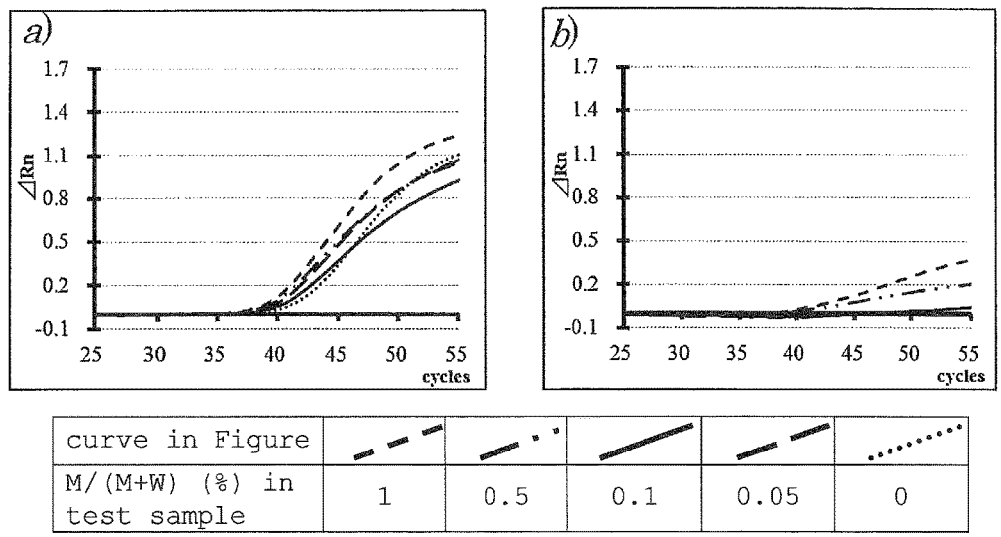
FIG. 23 shows a nucleic acid amplification curve by each probe (a: oligo 3-2 and b: oligo 14) for real-time PCR of each test sample (mixed sample of mutated/(mutated+wild-type) (1%-0%) genes) by a BNA clamp method using oligo 6 and targeting KRAS gene G12V mutation, which is obtained in Example 5.

A mixture of the above-mentioned (1)-(3) of the test samples, reagent for nucleic acid amplification, primer, probe for nucleic acid amplification, clamp nucleic acid and probe for mutation detection was subjected to (i) 50° C. for 2 min, (ii) 95° C. for 20 sec, (iii) 95° C., for 10 sec, (iv) 57° C. for 60 sec, after which (v) operations of (iii)-(iv) were repeated 45-55 times in a nucleic acid amplification apparatus. Nucleic acid amplification curves monitoring the nucleic acid amplification processes (up to 45 cycles) using a nucleic acid amplification probe and each probe for mutation detection in each test sample are shown in FIGS. 21-23. In addition, the Ct value data in this experiment are collectively shown in Table 7.

These data has clarified that, even when a DNA derived from patients tissue FFPE is used as a test sample, a nucleic acid amplification method using the present BNA clamp method and a mutation detection probe in combination can detect and analyze a point mutation of KRAS gene, as to the presence or absence of the mutation and the mutation mode, with high sensitivity (nearly about 0.1%).

TABLE 7

Ct value data targeting KRAS gene G12V mutation in Example 5

| | M/(M + W) (%) | | | | |
|---|---|---|---|---|---|
| | 1% | 0.5% | 0.1% | 0.05% | 0% |
| clamp oligo: oligo 4-2, amplification monitor: oligo 3-2 | | | | | |
| Ct value | 34.47 | 35.48 | 36.75 | 37.72 | 38.48 |
| ΔCt value (0%-X %) | 4.00 | 2.99 | 1.73 | 0.75 | |
| clamp oligo: oligo 4-2, amplification monitor: oligo 14 | | | | | |
| Ct value | 30.63 | 31.77 | 33.62 | 35.35 | >55 |
| ΔCt value (0%-X %) | >24.37 | >23.23 | >21.38 | >19.65 | |
| clamp oligo: oligo 5, amplification monitor: oligo 3-2 | | | | | |
| Ct value | 34.30 | 34.94 | 36.09 | 36.45 | 37.26 |
| ΔCt value (0%-X %) | 2.96 | 2.32 | 1.17 | 0.81 | |
| clamp oligo: oligo 5, amplification monitor: oligo 14 | | | | | |
| Ct value | 33.64 | 34.80 | 36.63 | 39.97 | >55 |
| ΔCt value (0%-X %) | >21.36 | >20.20 | >18.37 | >15.03 | |
| clamp oligo: oligo 6, amplification monitor: oligo 3-2 | | | | | |
| Ct value | 39.09 | 39.51 | 40.65 | 39.94 | 41.42 |
| ΔCt value (0%-X %) | 2.33 | 1.91 | 0.77 | 1.48 | |

TABLE 7-continued

Ct value data targeting KRAS gene G12V mutation in Example 5

| | M/(M + W) (%) | | | | |
|---|---|---|---|---|---|
| | 1% | 0.5% | 0.1% | 0.05% | 0% |
| clamp oligo: oligo 6, amplification monitor: oligo 14 | | | | | |
| Ct value | 38.21 | 39.10 | >55 | >55 | >55 |
| ΔCt value (0%-X %) | >16.79 | >15.90 | — | — | |

[Example 6] Detection of EGFR Gene Exon19 Deletion Mutation by BNA Clamp Method (1) Test Sample As gene samples of wild-type and E746-A750 del (Type 1) deletion mutation type of EGFR gene, the corresponding commercially available human genomic DNAs were used. The amount of each DNA was determined from the UV spectrum of each sample and Ct value obtained by real-time PCR using oligo 22, 23 and 24 as forward primer, reverse primer and nucleic acid amplification probe. Based on the DNA amount thereof, model test samples having a deletion mutation type of 100%, 10%, 1.0%, 0.1%, 0.01% or 0% were produced, and the respective model test samples were used in an amount of 50 ng per each experiment.

(2) Nucleic Acid Amplification Apparatus and Reagent for Nucleic Acid Amplification StepOnePlus (manufactured by ABI) was used as a real-time PCR apparatus and TagMan™ Fast Advanced Master Mix (manufactured by ABI) was used as the reagents for nucleic acid amplification. The amount of the reagent to be used was in accordance with the attached manual.

(3) Primer, Nucleic Acid Amplification Probe, Clamp Nucleic Acid, and Mutation Detection Probe Oligo 22 and oligo 23 (each 10 pmol) were used per experiment as forward and reverse primers, and oligo 24 (2.5 pmol) was used per experiment as a nucleic acid amplification probe. As BNA clamp nucleic acid, oligo 25 was used at 10 pmol per experiment, and oligo 26 was used at 5 pmol per experiment as a mutation detection probe to selectively recognize and detect deletion mutation type.

(4) Operation and Results of Nucleic Acid Amplification

Figure 24:
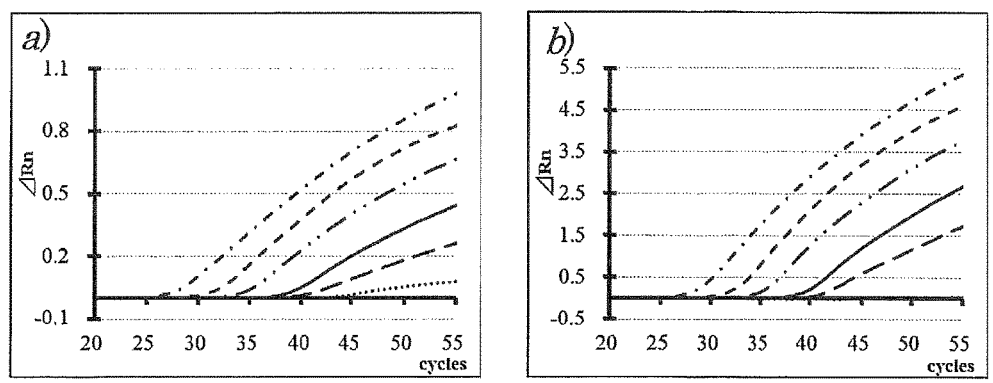
FIG. 24 shows a nucleic acid amplification curve by each probe (a: oligo 24 and b: oligo 26) for real-time PCR of each test sample (mixed sample of mutated/(mutated+wild-type) (100%-0%) genes) by a BNA clamp method using oligo 25 and targeting EGFR gene E746-A750 del (Type 1) mutation, which is obtained in Example 6.

A mixture of the above-mentioned (1)-(3) of the test samples, reagent for nucleic acid amplification, primer, probe for nucleic acid amplification, clamp nucleic acid and probe for mutation detection was subjected to (i) 50° C. for 2 min, (ii) 95° C. for 20 sec, (iii) 95° C. for 10 sec, (iv) 53° C. for 60 sec, after which (v) operations of (iii)-(iv) were repeated 45-55 times in a nucleic acid amplification apparatus. Nucleic acid amplification curves monitoring the nucleic acid amplification processes (up to 55 cycles) using a nucleic acid amplification probe (oligo 24) and each probe (oligo 26) for mutation detection in each test sample are shown in FIG. 24. In addition, the Ct value data in this experiment are collectively shown in Table 8.

To compare the effect of BNA clamp oligo, moreover, oligo 27 (LNA), oligo 28 (PNA) and oligo 29 (DNA) were used for each clamp oligo instead of oligo 25 and the test was performed under the same conditions (oligo 26 as a mutation detection probe was not used), and the process of nucleic acid amplification was monitored by oligo 24 (FIG. 25 and Table 9).

These data has clarified that, even when deletion mutation of EGFR gene is the target, a nucleic acid amplification method using the present RNA clamp method and a mutation detection probe in combination can detect and analyze the presence or absence of the mutation and the mutation mode with high sensitivity (not less than 0.1%). In addition, BNA oligo as a clamp oligo was clarified to be more highly functional than other oligo materials (LNA, PNA etc.).

TABLE 8

Ct value data (1) targeting EGFR gene E746-A750 del (Type 1) mutation in Example 6

| | M/(M + W) (%) | | | | | |
|---|---|---|---|---|---|---|
| | 100% | 10% | 1% | 0.1% | 0.01% | 0% |
| clamp oligo: oligo 25 + mutation detection probe: oligo 26, amplification monitor: oligo 24 | | | | | | |
| Ct value | 26.17 | 29.92 | 33.05 | 37.66 | 39.96 | 44.81 |
| ΔCt value (0% − X %) | 18.63 | 14.89 | 11.76 | 7.15 | 4.85 | |
| clamp oligo: oligo 25 + mutation detection probe: oligo 26, amplification monitor: oligo 26 | | | | | | |
| Ct value | 25.27 | 29.09 | 32.33 | 36.79 | 39.14 | >55 |
| ΔCt value (0% − X %) | >29.73 | >25.91 | >22.67 | >18.21 | >15.86 | |

TABLE 9

Ct value data (2) targeting EGFR gene E746-A750 del (Type 1) mutation in Example 6

| | M/(M + W) (%) | | | | | |
|---|---|---|---|---|---|---|
| | 100% | 10% | 1% | 0.1% | 0.01% | 0% |
| clamp oligo (BNA): oligo 25, amplification monitor: oligo 24 | | | | | | |
| Ct value | 25.33 | 28.77 | 32.35 | 34.82 | >55 | >55 |
| ΔCt value (0% − X %) | >29.67 | >26.23 | >22.65 | >20.18 | — | |
| clamp oligo (LNA): oligo 27, amplification monitor: oligo 24 | | | | | | |
| Ct value | 25.34 | 28.79 | 32.09 | 34.84 | 36.15 | 35.86 |
| ΔCt value (0% − X %) | 10.52 | 7.08 | 3.77 | 1.02 | −0.29 | |
| clamp oligo (PNA): oligo 28, amplification monitor: oligo 24 | | | | | | |
| Ct value | 25.04 | 24.91 | 24.75 | 25.04 | 24.69 | 24.77 |
| ΔCt value (0% − X %) | −0.27 | −0.14 | 0.02 | −0.27 | 0.08 | |
| clamp oligo (DNA): oligo 29, amplification monitor: oligo 24 | | | | | | |
| Ct value | 24.98 | 24.56 | 24.49 | 24.25 | 24.41 | 24.25 |
| ΔCt value (0% − X %) | −0.73 | −0.31 | −0.24 | 0.00 | −0.16 | |

INDUSTRIAL APPLICABILITY

The present invention relating to a BNA clamp technique provides a test method which is not limited to a technique for detecting a "specific mutation of particular gene" in a "model test sample" having a clarified presence ratio of mutation type gene with high sensitivity and high accuracy, but capable of (1) using various gene DNA samples obtained from various test sample forms (biological tissue, formalin-fixed paraffin embedded tissue section, body fluid etc.) by an appropriate isolation operation as test sample, and (2) detecting the presence or absence of various mutation type genes contained in a trace amount in a wild-type gene with high sensitivity and high accuracy and convenience.

Moreover, use of a BNA clamp technique and a mutation the detection probe in combination enables further improvement of the detection sensitivity accuracy, which in turn provides a basic technique capable of specifying and analyzing not only the presence or absence of a mutation type gene, but also specifying and analyzing the form of the mutation type, and meeting various industrial needs.

This application is based on a patent application No. 2012-217657 filed in Japan on Sep. 28, 2012, the contents of which are incorporated in full herein.

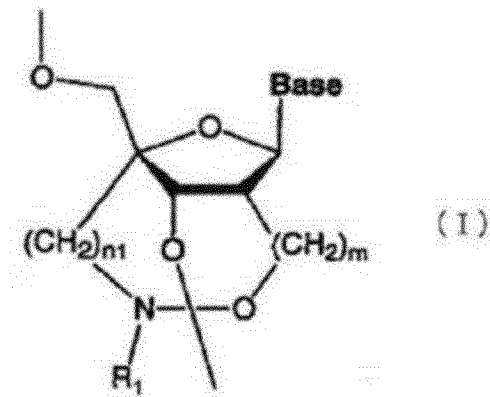

The invention claimed is:

1. A method of detecting a target nucleic acid having a difference in a base sequence in a detection target site in the target nucleic acid in a test sample, wherein the target nucleic acid comprises at least one difference in the base sequence from a detection non-target nucleic acid, comprising a step of selectively amplifying a region containing at least a part of the detection target site of the detection target nucleic acid in the test sample by a nucleic acid amplification method using a clamp nucleic acid having a base sequence complementary to the base sequence of the detection target site in the detection non-target nucleic acid, and a step of detecting the amplified nucleic acid, wherein the clamp nucleic acid is an oligonucleotide analog containing one or more of a unit structure of nucleoside analog represented by the following formula (I):

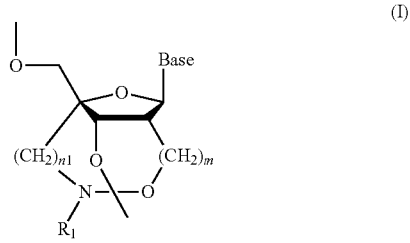

wherein

Base is a pyrimidine or purine nucleic acid base optionally having one or more substituents, $R_1$ is a hydrogen atom, an alkyl group, an alkenyl group, a cycloalkyl group, an aryl group, an aralkyl group, an acyl group, a sulfonyl group, a silyl group, or a functional molecule unit substituent, m is an integer of 0-2, and n1 is an integer of 1-3, provided a binding form between respective nucleoside analogs in the oligonucleotide analogs optionally contains one or more phosphorothioate bonds in addition to a phosphodiester bond and, when two or more of the aforementioned unit structures are contained, Base may be the same or different between the structures, or a salt thereof.

2. The method according to claim 1, wherein the clamp nucleic acid is an oligonucleotide analog containing one or more of the unit structure of nucleoside analog of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a hydrogen atom, an alkyl group having 1 to 5 carbon atoms, a benzyl group, an acetyl group, a benzoyl group, a methanesulfonyl group, or a p-toluenesulfonyl group, m is an integer of 0-2, and n1 is an integer of 1-3, or a salt thereof.

3. The method according to claim 1, wherein the clamp nucleic acid is an oligonucleotide analog containing one or more of the unit structure of nucleoside analog of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a methyl group, m is 0, and n1 is 1, or a salt thereof.

4. The method according to claim 1, wherein the clamp nucleic acid has a length of 5-30 mer.

5. The method according to claim 1, wherein the nucleic acid amplification method is a polymerase chain reaction (PCR) method.

6. The method according to claim 5, wherein the PCR method is a real-time PCR method.

7. The method according to claim 6, wherein the real-time PCR method is performed using a detection probe, and the detection probe is a single strand nucleic acid having a base sequence complementary to the base sequence of the region to be detected for a difference in a base sequence in a detection target site, wherein one terminal is substituted by a fluorescence group, the other terminal is substituted by a quenching group.

8. The method according to claim 7, wherein the detection probe is an oligonucleotide analog containing one or more of the unit structure of nucleoside analog of the above-mentioned formula (I), or a salt thereof.

9. The method according to claim 1, wherein the difference in the base sequence between the detection non-target nucleic acid and the detection target nucleic acid is caused by one or more mutations selected from the group consisting of substitution, insertion, deletion, inversion, overlap and translocation or a combination thereof.

10. The method according to claim 1, wherein the step of detecting the amplified nucleic acid comprises sequencing of an amplification product.

11. The method according to claim 1, wherein the target nucleic acid is a gene, and the difference in the base sequence of the gene to be the detection target relates to the onset and/or treatment sensitivity of a particular disease.

12. A kit for detection of a target nucleic acid having a difference in a base sequence in a detection target site in the target nucleic acid in a test sample, wherein the target nucleic acid is a detection target nucleic acid having at least one difference in a base sequence from a detection non-target nucleic acid, the kit comprising (a) a clamp nucleic acid having a base sequence complementary to the base sequence of the detection target site of a detection non-target nucleic acid, and (b) a reagent for selectively amplifying a region containing at least a part of the detection target site of the detection target nucleic acid in the test sample, wherein the clamp nucleic acid is an oligonucleotide analog containing one or more of a unit structure of nucleoside analog represented by the following formula (I):

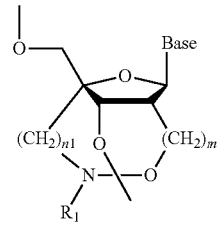

wherein

Base is a pyrimidine or purine nucleic acid base optionally having one or more substituents, $R_1$ is a hydrogen atom, an alkyl group, an alkenyl group, a cycloalkyl group, an aryl group, an aralkyl group, an acyl group, a sulfonyl group, a silyl group, or a functional molecule unit substituent, m is an integer of 0-2, and n1 is an integer of 1-3, provided a binding form between respective nucleoside analogs in the oligonucleotide analogs optionally contains one or more phosphorothioate bonds in addition to a phosphodiester bond and, when two or more of the aforementioned unit structures are contained, Base may be the same or different between the structures, or a salt thereof.

13. The kit according to claim 12, wherein the clamp nucleic acid is an oligonucleotide analog containing one or more of the unit structure of nucleoside analog of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, $R_1$ is a hydrogen atom, an alkyl group having 1 to 5 carbon atoms, a benzyl group, an acetyl group, a benzoyl group, a methanesulfonyl group, or a p-toluenesulfonyl group, m is an integer of 0-2, and n1 is an integer of 1-3, or a salt thereof.

14. The kit according to claim 12, wherein the clamp nucleic acid is an oligonucleotide analog containing one or more of the unit structure of nucleoside analog of the above-mentioned formula (I), wherein Base is a pyrimidine or purine nucleic acid base optionally having one or more substituents selected from the group consisting of a hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom, R₁ is a methyl group,
m is 0, and
n1 is 1,
or a salt thereof.

15. The kit according to claim 12, wherein the clamp nucleic acid has a length of 5-30 mer.

16. The kit according to claim 12, wherein the reagent of the aforementioned (b) comprises an amplification primer for polymerase chain reaction (PCR).

17. The kit according to claim 16, wherein the reagent of the aforementioned (b) further comprises a reagent for real-time PCR.

18. The kit according to claim 17, wherein the real-time PCR method is performed using a detection probe, and the detection probe is a single strand nucleic acid having a base sequence complementary to the base sequence of the region to be detected for a difference in a base sequence in a detection target nucleic acid, wherein one terminal is substituted by a fluorescence group, the other terminal is substituted by a quenching group.

19. The kit according to claim 18, wherein the detection probe is an oligonucleotide analog containing one or more of the unit structure of nucleoside analog of the above-mentioned formula (I), or a salt thereof.

20. The kit according to claim 12, wherein the difference in the base sequence between the detection non-target nucleic acid and the detection target nucleic acid is caused by one or more mutations selected from the group consisting of substitution, insertion, deletion, inversion, overlap and translocation or a combination thereof.

21. The kit according to claim 12, wherein the target nucleic acid is a gene, and the difference in the base sequence of the gene to be the detection target relates to the onset and/or treatment sensitivity of a particular disease.

* * * * *

UNITED STATES PATENT AND TRADEMARK OFFICE
CERTIFICATE OF CORRECTION

PATENT NO. : 10,253,360 B2
APPLICATION NO. : 14/431380
DATED : April 9, 2019
INVENTOR(S) : Imanishi et al.

It is certified that error appears in the above-identified patent and that said Letters Patent is hereby corrected as shown below:

On the Title Page

(57) ABSTRACT, formula (I) should read:

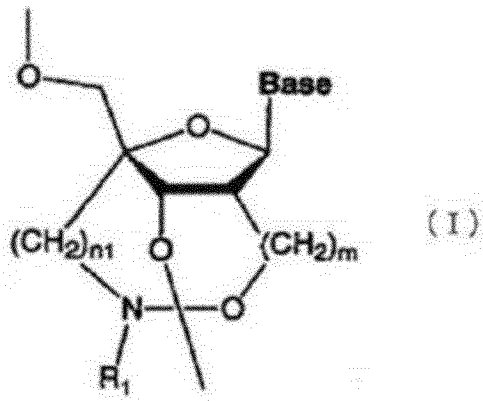

In the Specification

Column 5, Lines 1-12, formula (I) should read:

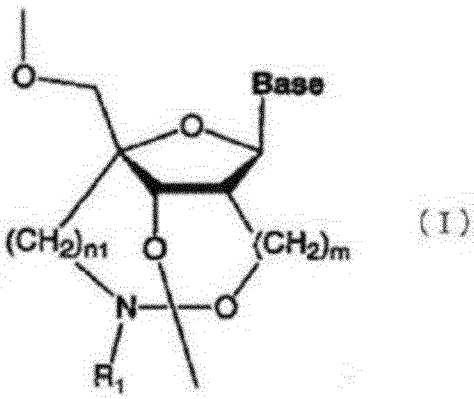

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,253,360 B2

Column 8, Lines 1-12, formula (I) should read:

SEQUENCE LISTING

```
<160> NUMBER OF SEQ ID NOS: 35

<210> SEQ ID NO 1
<211> LENGTH: 134
<212> TYPE: DNA
<213> ORGANISM: Homo sapiens
<220> FEATURE:
<221> NAME/KEY: CDS
<222> LOCATION: (18)..(128)

<400> SEQUENCE: 1
tataaggcct gctgaaa atg act gaa tat aaa ctt gtg gta gtt gga gct        50
                   Met Thr Glu Tyr Lys Leu Val Val Val Gly Ala
                    1               5                  10 ggt ggc gta ggc aag agt gcc ttg acg ata cag cta att cag aat cat        98
Gly Gly Val Gly Lys Ser Ala Leu Thr Ile Gln Leu Ile Gln Asn His
         15                  20                  25 ttt gtg gac gaa tat gat cca aca ata gag gtaaat                        134
Phe Val Asp Glu Tyr Asp Pro Thr Ile Glu
         30                  35

<210> SEQ ID NO 2
<211> LENGTH: 37
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
             20                  25                  30

Asp Pro Thr Ile Glu
         35

<210> SEQ ID NO 3
<211> LENGTH: 22
<212> TYPE: DNA
<213> ORGANISM: Artificial Sequence
<220> FEATURE:
<223> OTHER INFORMATION: Forward primer

<400> SEQUENCE: 3
actgaatata aacttgtggt ag                                               22

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
attgttggat catattcgtc                                                  20

<210> SEQ ID NO 5
<211> LENGTH: 28
<212> TYPE: DNA
<213> ORGANISM: Artificial Sequence
<220> FEATURE:
```

```
<223> OTHER INFORMATION: Probe
<220> FEATURE:
<221> NAME/KEY: misc_feature
<222> LOCATION: (1)..(1)
<223> OTHER INFORMATION: FAM-modified cytosine
<220> FEATURE:
<221> NAME/KEY: misc_feature
<222> LOCATION: (28)..(28)
<223> OTHER INFORMATION: TAMRA-modified thymine

<400> SEQUENCE: 5
nttgacgata cagctaattc agaatcan                                              28

<210> SEQ ID NO 6
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: JOE-modified cytosine
<220> FEATURE:
<221> NAME/KEY: misc_feature
<222> LOCATION: (28)..(28)
<223> OTHER INFORMATION: TAMRA-modified thymine

<400> SEQUENCE: 6
nttgacgata cagctaattc agaatcan                                              28

<210> SEQ ID NO 7
<211> LENGTH: 10
<212> TYPE: DNA
<213> ORGANISM: Artificial Sequence
<220> FEATURE:
<223> OTHER INFORMATION: BNA clamp
<220> FEATURE:
<221> NAME/KEY: misc_feature
<222> LOCATION: (1)..(1)
<223> OTHER INFORMATION: 2',4'-BNANC(N-Me)-methylcytosine
<220> FEATURE:
<221> NAME/KEY: misc_feature
<222> LOCATION: (3)..(4)
<223> OTHER INFORMATION: 2',4'-BNANC(N-Me)-methylcytosine
<220> FEATURE:
<221> NAME/KEY: misc_feature
<222> LOCATION: (5)..(5)
<223> OTHER INFORMATION: 2',4'-BNANC(N-Me)-adenine
<220> FEATURE:
<221> NAME/KEY: misc_feature
<222> LOCATION: (6)..(7)
<223> OTHER INFORMATION: 2',4'-BNANC(N-Me)-methylcytosine
<220> FEATURE:
<221> NAME/KEY: misc_feature
<222> LOCATION: (8)..(8)
<223> OTHER INFORMATION: 2',4'-BNANC(N-Me)-adenine
<220> FEATURE:
<221> NAME/KEY: misc_feature
<222> LOCATION: (10)..(10)
<223> OTHER INFORMATION: monophosphorylated 2',4'-BNANC(N-Me)-
      methylcytosine

<400> SEQUENCE: 7 ngnnnnnngn                                                                  10

<210> SEQ ID NO 8
<211> LENGTH: 13
<212> TYPE: DNA
<213> ORGANISM: Artificial Sequence
<220> FEATURE:
<223> OTHER INFORMATION: BNA clamp
<220> FEATURE:
```

<220> FEATURE:
<221> NAME/KEY: misc_feature
<222> LOCATION: (1)..(1)
<223> OTHER INFORMATION: 2'-OMe-RNA-uracil
<220> FEATURE:
<221> NAME/KEY: misc_feature
<222> LOCATION: (1)..(13)
<223> OTHER INFORMATION: DNA/RNA hybrid
<220> FEATURE:
<221> NAME/KEY: misc_feature
<222> LOCATION: (3)..(3)
<223> OTHER INFORMATION: 2',4'-BNANC(N-Me)-methylcytosine
<220> FEATURE:
<221> NAME/KEY: misc_feature
<222> LOCATION: (5)..(6)
<223> OTHER INFORMATION: 2',4'-BNANC(N-Me)-methylcytosine
<220> FEATURE:
<221> NAME/KEY: misc_feature
<222> LOCATION: (7)..(7)
<223> OTHER INFORMATION: 2',4'-BNANC(N-Me)-adenine
<220> FEATURE:
<221> NAME/KEY: misc_feature
<222> LOCATION: (8)..(9)
<223> OTHER INFORMATION: 2',4'-BNANC(N-Me)-methylcytosine
<220> FEATURE:
<221> NAME/KEY: misc_feature
<222> LOCATION: (10)..(10)
<223> OTHER INFORMATION: 2',4'-BNANC(N-Me)-adenine
<220> FEATURE:
<221> NAME/KEY: misc_feature
<222> LOCATION: (12)..(12)
<223> OTHER INFORMATION: 2',4'-BNANC(N-Me)-methylcytosine
<220> FEATURE:
<221> NAME/KEY: misc_feature
<222> LOCATION: (13)..(13)
<223> OTHER INFORMATION: monophosphorylated thymine

<400> SEQUENCE: 8
nangnnnnnn gnn                                                13

<210> SEQ ID NO 9
<211> LENGTH: 18
<212> TYPE: DNA
<213> ORGANISM: Artificial Sequence
<220> FEATURE:
<223> OTHER INFORMATION: Synthetic BNA clamp
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (4)..(4)
<223> OTHER INFORMATION: 2',4'-BNANC(N-Me)-thymine
<220> FEATURE:
<221> NAME/KEY: misc_feature
<222> LOCATION: (6)..(6)
<223> OTHER INFORMATION: 2',4'-BNANC(N-Me)-methylcytosine
<220> FEATURE:
<221> NAME/KEY: misc_feature
<222> LOCATION: (8)..(9)
<223> OTHER INFORMATION: 2',4'-BNANC(N-Me)-methylcytosine
<220> FEATURE:
<221> NAME/KEY: misc_feature
<222> LOCATION: (11)..(12)
<223> OTHER INFORMATION: 2',4'-BNANC(N-Me)-methylcytosine
<220> FEATURE:
<221> NAME/KEY: misc_feature
<222> LOCATION: (15)..(15)
<223> OTHER INFORMATION: 2',4'-BNANC(N-Me)-methylcytosine
<220> FEATURE:
<221> NAME/KEY: misc_feature
<222> LOCATION: (18)..(18)
<223> OTHER INFORMATION: monophosphorylated cytosine -continued

<400> SEQUENCE: 9
nccnangnna nnagntcn                                                    18

<210> SEQ ID NO 10
<211> LENGTH: 10
<212> TYPE: DNA
<213> ORGANISM: Artificial Sequence
<220> FEATURE:
<223> OTHER INFORMATION: Synthetic LNA clamp
<220> FEATURE:
<221> NAME/KEY: misc_feature
<222> LOCATION: (1)..(1)
<223> OTHER INFORMATION: LNA-methylcytosine
<220> FEATURE:
<221> NAME/KEY: misc_feature
<222> LOCATION: (3)..(4)
<223> OTHER INFORMATION: LNA-methylcytosine
<220> FEATURE:
<221> NAME/KEY: misc_feature
<222> LOCATION: (5)..(5)
<223> OTHER INFORMATION: LNA-adenine
<220> FEATURE:
<221> NAME/KEY: misc_feature
<222> LOCATION: (6)..(7)
<223> OTHER INFORMATION: LNA-methylcytosine
<220> FEATURE:
<221> NAME/KEY: misc_feature
<222> LOCATION: (8)..(8)
<223> OTHER INFORMATION: LNA-adenine
<220> FEATURE:
<221> NAME/KEY: misc_feature
<222> LOCATION: (10)..(10)
<223> OTHER INFORMATION: monophosphorylated LNA-methylcytosine

<400> SEQUENCE: 10 ngnnnnnngn                                                             10

<210> SEQ ID NO 11
<211> LENGTH: 13
<212> TYPE: DNA
<213> ORGANISM: Artificial Sequence
<220> FEATURE:
<223> OTHER INFORMATION: Synthetic DNA clamp
<220> FEATURE:
<221> NAME/KEY: misc_feature
<222> LOCATION: (1)..(1)
<223> OTHER INFORMATION: 2'-OMe-RNA-uracil
<220> FEATURE:
<221> NAME/KEY: misc_feature
<222> LOCATION: (1)..(13)
<223> OTHER INFORMATION: DNA/RNA hybrid
<220> FEATURE:
<221> NAME/KEY: misc_feature
<222> LOCATION: (13)..(13)
<223> OTHER INFORMATION: monophosphorylated thymine

<400> SEQUENCE: 11
nacgccacca gcn                                                         13

<210> SEQ ID NO 12
<211> LENGTH: 13
<212> TYPE: DNA
<213> ORGANISM: Artificial Sequence
<220> FEATURE:
<223> OTHER INFORMATION: Synthetic LNA clamp
<220> FEATURE:
<221> NAME/KEY: misc_feature
<222> LOCATION: (1)..(1)
<223> OTHER INFORMATION: 2'-OMe-RNA-uracil
<220> FEATURE:
<221> NAME/KEY: misc_feature
<222> LOCATION: (1)..(13)

```
<223> OTHER INFORMATION: DNA/RNA hybrid
<220> FEATURE:
<221> NAME/KEY: misc_feature
<222> LOCATION: (3)..(3)
<223> OTHER INFORMATION: LNA-methylcytosine
<220> FEATURE:
<221> NAME/KEY: misc_feature
<222> LOCATION: (5)..(6)
<223> OTHER INFORMATION: LNA-methylcytosine
<220> FEATURE:
<221> NAME/KEY: misc_feature
<222> LOCATION: (7)..(7)
<223> OTHER INFORMATION: LNA-adenine
<220> FEATURE:
<221> NAME/KEY: misc_feature
<222> LOCATION: (8)..(9)
<223> OTHER INFORMATION: LNA-methylcytosine
<220> FEATURE:
<221> NAME/KEY: misc_feature
<222> LOCATION: (10)..(10)
<223> OTHER INFORMATION: LNA-adenine
<220> FEATURE:
<221> NAME/KEY: misc_feature
<222> LOCATION: (12)..(12)
<223> OTHER INFORMATION: LNA-methylcytosine
<220> FEATURE:
<221> NAME/KEY: misc_feature
<222> LOCATION: (13)..(13)
<223> OTHER INFORMATION: monophosphorylated thymine

<400> SEQUENCE: 12
nangnnnnnn gnn                                                        13

<210> SEQ ID NO 13
<211> LENGTH: 13
<212> TYPE: DNA
<213> ORGANISM: Artificial Sequence
<220> FEATURE:
<223> OTHER INFORMATION: Synthetic PNA clamp
<220> FEATURE:
<221> NAME/KEY: misc_feature
<222> LOCATION: (1)..(1)
<223> OTHER INFORMATION: PNA-thymine
<220> FEATURE:
<221> NAME/KEY: misc_feature
<222> LOCATION: (2)..(2)
<223> OTHER INFORMATION: PNA-adenine
<220> FEATURE:
<221> NAME/KEY: misc_feature
<222> LOCATION: (3)..(3)
<223> OTHER INFORMATION: PNA-cytosine
<220> FEATURE:
<221> NAME/KEY: misc_feature
<222> LOCATION: (4)..(4)
<223> OTHER INFORMATION: PNA-guanine
<220> FEATURE:
<221> NAME/KEY: misc_feature
<222> LOCATION: (5)..(6)
<223> OTHER INFORMATION: PNA-cytosine
<220> FEATURE:
<221> NAME/KEY: misc_feature
<222> LOCATION: (7)..(7)
<223> OTHER INFORMATION: PNA-adenine
<220> FEATURE:
<221> NAME/KEY: misc_feature
<222> LOCATION: (8)..(9)
<223> OTHER INFORMATION: PNA-cytosine
<220> FEATURE:
<221> NAME/KEY: misc_feature
<222> LOCATION: (10)..(10)
<223> OTHER INFORMATION: PNA-adenine
<220> FEATURE:
<221> NAME/KEY: misc_feature
<222> LOCATION: (11)..(11)
<223> OTHER INFORMATION: PNA-guanine
<220> FEATURE:
<221> NAME/KEY: misc_feature
```

```
<222> LOCATION: (12)..(12)
<223> OTHER INFORMATION: PNA-cytosine
<220> FEATURE:
<221> NAME/KEY: misc_feature
<222> LOCATION: (13)..(13)
<223> OTHER INFORMATION: PNA-thymine

<400> SEQUENCE: 13
nnnnnnnnnn nnn                                                    13

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA clamp
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (18)..(18)
<223> OTHER INFORMATION: monophosphorylated cytosine

<400> SEQUENCE: 14
ncctacgcca ccagctcn                                               18

<210> SEQ ID NO 15
<211> LENGTH: 18
<212> TYPE: DNA
<213> ORGANISM: Artificial Sequence
<220> FEATURE:
<223> OTHER INFORMATION: Synthetic LNA clamp
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (4)..(4)
<223> OTHER INFORMATION: LNA-thymine
<220> FEATURE:
<221> NAME/KEY: misc_feature
<222> LOCATION: (6)..(6)
<223> OTHER INFORMATION: LNA-cytosine
<220> FEATURE:
<221> NAME/KEY: misc_feature
<222> LOCATION: (8)..(9)
<223> OTHER INFORMATION: LNA-cytosine
<220> FEATURE:
<221> NAME/KEY: misc_feature
<222> LOCATION: (11)..(12)
<223> OTHER INFORMATION: LNA-cytosine
<220> FEATURE:
<221> NAME/KEY: misc_feature
<222> LOCATION: (15)..(15)
<223> OTHER INFORMATION: LNA-cytosine
<220> FEATURE:
<221> NAME/KEY: misc_feature
<222> LOCATION: (18)..(18)
<223> OTHER INFORMATION: monophosphorylated cytosine

<400> SEQUENCE: 15
nccnangnna nnagntcn                                               18
```

```
<210> SEQ ID NO 16
<211> LENGTH: 18
<212> TYPE: DNA
<213> ORGANISM: Artificial Sequence
<220> FEATURE:
<223> OTHER INFORMATION: Synthetic PNA clamp
<220> FEATURE:
<221> NAME/KEY: misc_feature
<222> LOCATION: (1)..(1)
<223> OTHER INFORMATION: PNA-guanine
<220> FEATURE:
<221> NAME/KEY: misc_feature
<222> LOCATION: (2)..(3)
<223> OTHER INFORMATION: PNA-cytosine
<220> FEATURE:
<221> NAME/KEY: misc_feature
<222> LOCATION: (4)..(4)
<223> OTHER INFORMATION: PNA-thymine
<220> FEATURE:
<221> NAME/KEY: misc_feature
<222> LOCATION: (5)..(5)
<223> OTHER INFORMATION: PNA-adenine
<220> FEATURE:
<221> NAME/KEY: misc_feature
<222> LOCATION: (6)..(6)
<223> OTHER INFORMATION: PNA-cytosine
<220> FEATURE:
<221> NAME/KEY: misc_feature
<222> LOCATION: (7)..(7)
<223> OTHER INFORMATION: PNA-guanine
<220> FEATURE:
<221> NAME/KEY: misc_feature
<222> LOCATION: (8)..(9)
<223> OTHER INFORMATION: PNA-cytosine
<220> FEATURE:
<221> NAME/KEY: misc_feature
<222> LOCATION: (10)..(10)
<223> OTHER INFORMATION: PNA-adenine
<220> FEATURE:
<221> NAME/KEY: misc_feature
<222> LOCATION: (11)..(12)
<223> OTHER INFORMATION: PNA-cytosine
<220> FEATURE:
<221> NAME/KEY: misc_feature
<222> LOCATION: (13)..(13)
<223> OTHER INFORMATION: PNA-adenine
<220> FEATURE:
<221> NAME/KEY: misc_feature
<222> LOCATION: (14)..(14)
<223> OTHER INFORMATION: PNA-guanine
<220> FEATURE:
<221> NAME/KEY: misc_feature
<222> LOCATION: (15)..(15)
<223> OTHER INFORMATION: PNA-cytosine
<220> FEATURE:
<221> NAME/KEY: misc_feature
<222> LOCATION: (16)..(16)
<223> OTHER INFORMATION: PNA-thymine
<220> FEATURE:
<221> NAME/KEY: misc_feature
<222> LOCATION: (17)..(18)
<223> OTHER INFORMATION: PNA-cytosine

<400> SEQUENCE: 16 nnnnnnnnn nnnnnnnn                                              18

<210> SEQ ID NO 17
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
```

```
<220> FEATURE:
<221> NAME/KEY: misc_feature
<222> LOCATION: (15)..(15)
<223> OTHER INFORMATION: TAMRA-modified cytosine

<400> SEQUENCE: 17
nacgccaaca gctcn                                                          15

<210> SEQ ID NO 18
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (8)..(8)
<223> OTHER INFORMATION: 2',4'-BNANC(N-Me)-adenine
<220> FEATURE:
<221> NAME/KEY: misc_feature
<222> LOCATION: (15)..(15)
<223> OTHER INFORMATION: TAMRA-modified cytosine

<400> SEQUENCE: 18
nacgccanca gctcn                                                          15

<210> SEQ ID NO 19
<211> LENGTH: 10
<212> TYPE: DNA
<213> ORGANISM: Artificial Sequence
<220> FEATURE:
<223> OTHER INFORMATION: Synthetic BNA clamp
<220> FEATURE:
<221> NAME/KEY: misc_feature
<222> LOCATION: (1)..(1)
<223> OTHER INFORMATION: 2',4'-BNANC(N-Me)-methylcytosine
<220> FEATURE:
<221> NAME/KEY: misc_feature
<222> LOCATION: (2)..(2)
<223> OTHER INFORMATION: 2',4'-BNANC(N-Me)-guanine
<220> FEATURE:
<221> NAME/KEY: misc_feature
<222> LOCATION: (3)..(4)
<223> OTHER INFORMATION: 2',4'-BNANC(N-Me)-methylcytosine
<220> FEATURE:
<221> NAME/KEY: misc_feature
<222> LOCATION: (5)..(5)
<223> OTHER INFORMATION: 2',4'-BNANC(N-Me)-adenine
<220> FEATURE:
<221> NAME/KEY: misc_feature
<222> LOCATION: (6)..(7)
<223> OTHER INFORMATION: 2',4'-BNANC(N-Me)-methylcytosine
<220> FEATURE:
<221> NAME/KEY: misc_feature
<222> LOCATION: (8)..(8)
<223> OTHER INFORMATION: 2',4'-BNANC(N-Me)-adenine
<220> FEATURE:
<221> NAME/KEY: misc_feature
<222> LOCATION: (9)..(9)
<223> OTHER INFORMATION: 2',4'-BNANC(N-Me)-guanine
<220> FEATURE:
<221> NAME/KEY: misc_feature
<222> LOCATION: (10)..(10)
<223> OTHER INFORMATION: monophosphorylated 2',4'-BNANC(N-Me)-
      methylcytosine

<400> SEQUENCE: 19 nnnnnnnnnn                                                                10
```

```
<210> SEQ ID NO 20
<211> LENGTH: 10
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified cytosine
<220> FEATURE:
<221> NAME/KEY: misc_feature
<222> LOCATION: (10)..(10)
<223> OTHER INFORMATION: TAMRA-modified cytosine

<400> SEQUENCE: 20 naacagctcn                                                                  10

<210> SEQ ID NO 21
<211> LENGTH: 10
<212> TYPE: DNA
<213> ORGANISM: Artificial Sequence
<220> FEATURE:
<223> OTHER INFORMATION: Detection BNA probe
<220> FEATURE:
<221> NAME/KEY: misc_feature
<222> LOCATION: (1)..(1)
<223> OTHER INFORMATION: FAM-modified cytosine
<220> FEATURE:
<221> NAME/KEY: misc_feature
<222> LOCATION: (3)..(3)
<223> OTHER INFORMATION: 2',4'-BNANC(N-Me)-adenine
<220> FEATURE:
<221> NAME/KEY: misc_feature
<222> LOCATION: (5)..(5)
<223> OTHER INFORMATION: 2',4'-BNANC(N-Me)-adenine
<220> FEATURE:
<221> NAME/KEY: misc_feature
<222> LOCATION: (7)..(7)
<223> OTHER INFORMATION: 2',4'-BNANC(N-Me)-methylcytosine
<220> FEATURE:
<221> NAME/KEY: misc_feature
<222> LOCATION: (9)..(9)
<223> OTHER INFORMATION: 2',4'-BNANC(N-Me)-methylcytosine
<220> FEATURE:
<221> NAME/KEY: misc_feature
<222> LOCATION: (10)..(10)
<223> OTHER INFORMATION: TAMRA-modified cytosine

<400> SEQUENCE: 21 nancngntnn                                                                  10

<210> SEQ ID NO 22
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 22
nacgccatca gctcn                                                            15

<210> SEQ ID NO 23
<211> LENGTH: 15
<212> TYPE: DNA
```

```
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 23
nacgtcacca gctcn                                                    15

<210> SEQ ID NO 24
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 24
nacgccagca gctcn                                                    15

<210> SEQ ID NO 25
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 25
nacgccacaa gctcn                                                    15

<210> SEQ ID NO 26
<211> LENGTH: 15
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 26
nacgccacta gctcn                                                    15

<210> SEQ ID NO 27
<211> LENGTH: 15
```

```
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (15)..(15)
<223> OTHER INFORMATION: TAMRA-modified cytosine

<400> SEQUENCE: 27
nacgccacga gctcn                                                          15

<210> SEQ ID NO 28
<211> LENGTH: 20
<212> TYPE: DNA
<213> ORGANISM: Artificial Sequence
<220> FEATURE:
<223> OTHER INFORMATION: Forward primer

<400> SEQUENCE: 28
tggcaccatc tcacaattgc                                                     20

<210> SEQ ID NO 29
<211> LENGTH: 20
<212> TYPE: DNA
<213> ORGANISM: Artificial Sequence
<220> FEATURE:
<223> OTHER INFORMATION: Reverse primer

<400> SEQUENCE: 29
acacagcaaa gcagaaactc                                                     20

<210> SEQ ID NO 30
<211> LENGTH: 26
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: JOE-modified cytosine
<220> FEATURE:
<221> NAME/KEY: misc_feature
<222> LOCATION: (26)..(26)
<223> OTHER INFORMATION: TAMRA-modified adenine

<400> SEQUENCE: 30
ncgaaagcca acaaggaaat cctcgn                                              26

<210> SEQ ID NO 31
<211> LENGTH: 18
<212> TYPE: DNA
<213> ORGANISM: Artificial Sequence
<220> FEATURE:
<223> OTHER INFORMATION: BNA clamp
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (2)..(3)
```

```
<223> OTHER INFORMATION: 2',4'-BNANC(N-H)-thymine
<220> FEATURE:
<221> NAME/KEY: misc_feature
<222> LOCATION: (6)..(7)
<223> OTHER INFORMATION: 2',4'-BNANC(N-H)-thymine
<220> FEATURE:
<221> NAME/KEY: misc_feature
<222> LOCATION: (8)..(8)
<223> OTHER INFORMATION: 2',4'-BNANC(N-H)-methylcytosine
<220> FEATURE:
<221> NAME/KEY: misc_feature
<222> LOCATION: (9)..(9)
<223> OTHER INFORMATION: 2',4'-BNANC(N-H)-thymine
<220> FEATURE:
<221> NAME/KEY: misc_feature
<222> LOCATION: (10)..(10)
<223> OTHER INFORMATION: 2',4'-BNANC(N-H)-methylcytosine
<220> FEATURE:
<221> NAME/KEY: misc_feature
<222> LOCATION: (11)..(11)
<223> OTHER INFORMATION: 2',4'-BNANC(N-H)-thymine
<220> FEATURE:
<221> NAME/KEY: misc_feature
<222> LOCATION: (16)..(16)
<223> OTHER INFORMATION: 2',4'-BNANC(N-H)-thymine
<220> FEATURE:
<221> NAME/KEY: misc_feature
<222> LOCATION: (18)..(18)
<223> OTHER INFORMATION: monophosphorylated 2',4'-BNANC(N-H)-
      methylcytosine

<400> SEQUENCE: 31
nnngcnnnnn ntaatncn                                                   18

<210> SEQ ID NO 32
<211> LENGTH: 22
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: FAM-modified thymine
<220> FEATURE:
<221> NAME/KEY: misc_feature
<222> LOCATION: (22)..(22)
<223> OTHER INFORMATION: TAMRA-modified thymine

<400> SEQUENCE: 32
ncccgtcgct atcaaaacat cn                                              22

<210> SEQ ID NO 33
<211> LENGTH: 18
<212> TYPE: DNA
<213> ORGANISM: Artificial Sequence
<220> FEATURE:
<223> OTHER INFORMATION: LNA clamp
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (2)..(3)
<223> OTHER INFORMATION: LNA-thymine
<220> FEATURE:
<221> NAME/KEY: misc_feature
<222> LOCATION: (6)..(7)
<223> OTHER INFORMATION: LNA-thymine
<220> FEATURE:
```

<221> NAME/KEY: misc_feature
<222> LOCATION: (8)..(8)
<223> OTHER INFORMATION: LNA-methylcytosine
<220> FEATURE:
<221> NAME/KEY: misc_feature
<222> LOCATION: (9)..(9)
<223> OTHER INFORMATION: LNA-thymine
<220> FEATURE:
<221> NAME/KEY: misc_feature
<222> LOCATION: (10)..(10)
<223> OTHER INFORMATION: LNA-methylcytosine
<220> FEATURE:
<221> NAME/KEY: misc_feature
<222> LOCATION: (11)..(11)
<223> OTHER INFORMATION: LNA-thymine
<220> FEATURE:
<221> NAME/KEY: misc_feature
<222> LOCATION: (16)..(16)
<223> OTHER INFORMATION: LNA-thymine
<220> FEATURE:
<221> NAME/KEY: misc_feature
<222> LOCATION: (18)..(18)
<223> OTHER INFORMATION: monophosphorylated LNA-methylcytosine

<400> SEQUENCE: 33
nnngcnnnnn ntaatncn                                                    18

<210> SEQ ID NO 34
<211> LENGTH: 18
<212> TYPE: DNA
<213> ORGANISM: Artificial Sequence
<220> FEATURE:
<223> OTHER INFORMATION: PNA clamp
<220> FEATURE:
<221> NAME/KEY: misc_feature
<222> LOCATION: (1)..(1)
<223> OTHER INFORMATION: PNA-guanine
<220> FEATURE:
<221> NAME/KEY: misc_feature
<222> LOCATION: (2)..(3)
<223> OTHER INFORMATION: PNA-thymine
<220> FEATURE:
<221> NAME/KEY: misc_feature
<222> LOCATION: (4)..(4)
<223> OTHER INFORMATION: PNA-guanine
<220> FEATURE:
<221> NAME/KEY: misc_feature
<222> LOCATION: (5)..(5)
<223> OTHER INFORMATION: PNA-cytosine
<220> FEATURE:
<221> NAME/KEY: misc_feature
<222> LOCATION: (6)..(7)
<223> OTHER INFORMATION: PNA-thymine
<220> FEATURE:
<221> NAME/KEY: misc_feature
<222> LOCATION: (8)..(8)
<223> OTHER INFORMATION: PNA-cytosine
<220> FEATURE:
<221> NAME/KEY: misc_feature
<222> LOCATION: (9)..(9)
<223> OTHER INFORMATION: PNA-thymine
<220> FEATURE:
<221> NAME/KEY: misc_feature
<222> LOCATION: (10)..(10)
<223> OTHER INFORMATION: PNA-cytosine
<220> FEATURE:
<221> NAME/KEY: misc_feature
<222> LOCATION: (11)..(12)
<223> OTHER INFORMATION: PNA-thymine
<220> FEATURE:
<221> NAME/KEY: misc_feature
<222> LOCATION: (13)..(14)
<223> OTHER INFORMATION: PNA-adenine
<220> FEATURE:
<221> NAME/KEY: misc_feature
<222> LOCATION: (15)..(16)
<223> OTHER INFORMATION: PNA-thymine

```
<220> FEATURE:
<221> NAME/KEY: misc_feature
<222> LOCATION: (17)..(18)
<223> OTHER INFORMATION: PNA-cytosine

<400> SEQUENCE: 34
nnnnnnnnnn nnnnnnnn                                          18

<210> SEQ ID NO 35
<211> LENGTH: 18
<212> TYPE: DNA
<213> ORGANISM: Artificial Sequence
<220> FEATURE:
<223> OTHER INFORMATION: DNA clampmagda
<220> FEATURE:
<221> NAME/KEY: misc_feature
<222> LOCATION: (1)..(1)
<223> OTHER INFORMATION: 2'-OMe-RNA-guanine
<220> FEATURE:
<221> NAME/KEY: misc_feature
<222> LOCATION: (1)..(18)
<223> OTHER INFORMATION: DNA/RNA hybrid
<220> FEATURE:
<221> NAME/KEY: misc_feature
<222> LOCATION: (18)..(18)
<223> OTHER INFORMATION: monophosphorylated cytosine

<400> SEQUENCE: 35
nttgcttctc ttaattcn                                          18
```